United States Patent
Malone et al.

(10) Patent No.: US 8,969,583 B2
(45) Date of Patent: Mar. 3, 2015

(54) 3-PHENYL-5-UREIDOISOTHIAZOLE-4-CARBOXIMIDE AND 3-AMINO-5-PHENYLISOTHIAZOLE DERIVATIVES AS KINASE INHIBITORS

(71) Applicant: Allergan, Inc., Irvine, CA (US)

(72) Inventors: Thomas C. Malone, Irvine, CA (US); C. Eugene Hull, Aliso Viejo, CA (US); Sougato Boral, Santa Ana, CA (US); Julie A. Wurster, Irvine, CA (US); Michael R. Robinson, Irvine, CA (US); Jeffrey L. Edelman, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/728,502

(22) Filed: Dec. 27, 2012

(65) Prior Publication Data

US 2013/0172353 A1 Jul. 4, 2013

Related U.S. Application Data

(60) Provisional application No. 61/581,031, filed on Dec. 28, 2011.

(51) Int. Cl.
*C07D 275/03* (2006.01)
*C07D 417/12* (2006.01)
*A61K 31/5377* (2006.01)
*A61K 31/425* (2006.01)
*A61K 31/427* (2006.01)
*C07D 295/13* (2006.01)

(52) U.S. Cl.
CPC ............ *C07D 417/12* (2013.01); *C07D 275/03* (2013.01); *C07D 295/13* (2013.01)
USPC .......................................... 548/214; 544/133

(58) Field of Classification Search
USPC ........................................................ 548/214
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,630,200 | A | 12/1971 | Higuchi |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,366,738 | A | 11/1994 | Rork et al. |
| 5,538,939 | A * | 7/1996 | Muenster et al. ............. 504/269 |

FOREIGN PATENT DOCUMENTS

| | | |
|---|---|---|
| EP | 0640597 | 8/1994 |
| EP | 0995751 | 4/2000 |
| WO | 97-40019 | 10/1997 |
| WO | 99-62890 | 12/1999 |
| WO | 03-072541 | 9/2003 |
| WO | 2005-081997 | 9/2005 |
| WO | 2005-082001 | 9/2005 |
| WO | 2006-026034 | 3/2006 |

OTHER PUBLICATIONS

Chemical Abstracts Registry No. 1171922-04-5, indexed in the Registry file on STN CAS Online Aug. 3, 2009.*
Kappe et al., CA 121:205299, 1994.*
Banerjee et al., Bioorganic & Medicinal Chemistry Letters, (Mar. 23, 2012), 22(9), pp. 3223-3228.*
Goerdeler et al., CA 59:28526, 1963.*
Anderson et al, The Practice of Medicinal Chemistry, 1996, 32 Pages, 3rd Edition, Index only.
Arora, Amit et al, Role of Tyrosine Kinase Inhibitors in Cancer Therapy, Journal of Pharmacology and Experimental Therapeutics, 2005, 971-979, 315(3).
Benerjee, Abhisek et al, Isothiazole and Isoxazole Fused Pyrimidones as PDE7 Inhibitors: SAR and Pharmacokinetic Evaluation, Bioorganic & Medicinal Chemistry Letters, 2012, 3223-3228, 22.
Berge, Stephen M., Pharmaceutical Salts, Journal of Pharmaceutical Sciences, Jan. 1977, 1-19, 66 (1), US.
Bergers, Gabriele et al, Benefits of Targeting Both Pericytes and Endothelial Cells in the Tumor Vasculature With Kinase Inhibitors, J. Clin. Invest., 2003, 1287-1295, 111.
Bingham, Ann et al, Over One Hundred Solvates of Sulfathiazole, Chem. Commun., 2001, 603-604.
Caira, Mino et al, Preparation and Crystal Characterization of a Polymorph, a Monohydrate, and an Ethyl Acetate Solvate of the Antifungal Fluconazole, Journal of Pharmaceutical Sciences, Mar. 2004, 601-611, 93(3).
Chappelow, Aimee et al, Neovascular Age-Related Macular Degeneration, Drugs, 2008, 1029-1036, 68(8).
Cowan-Jacob, S.W., Structural Biology of Protein Tyrosine Kinases, Cell. Mol. Life Sci., 2006, 2608-2625, 63.
Edward B. Roche, Bioreversible Carriers in Drug Design, Theory and Application, 1987, Chapter 4, p. 121-163., American Pharmaceutical Association and Pergamon Press.
Gould, Philip, Salt Selection for Basic Drugs, International Journal of Pharmaceutics, 1986, 201-217, 33.

(Continued)

*Primary Examiner* — Laura L. Stockton
(74) *Attorney, Agent, or Firm* — Mark D. Kafka

(57) ABSTRACT

This invention is directed to a compound of Formula I

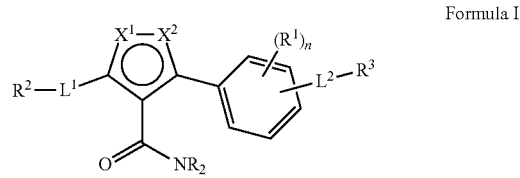

Formula I or a pharmaceutically acceptable salt thereof, wherein R, $R^1$, $R^2$, $R^3$, n, $X^1$, $X^2$, $L^1$, and $L^2$ are as defined herein. The compounds of Formula I are useful as receptor tyrosine kinase (RTK) inhibitors and can be used to treat such diseases as cancer, blood vessel proliferative disorders, fibrotic disorders, mesangial cell proliferative disorders and metabolic diseases.

16 Claims, No Drawings

(56) References Cited

OTHER PUBLICATIONS

Greene, Theodora, Protective Groups in Organic Synthesis, 1991, 52 Pages, 3rd Edition, Index only.

Heidenreich, Regina et al, Angiogenesis: The New Potential Target For The Therapy of Psoriasis?, Drug News Perspect, Mar. 2008, 97-105, 21(2).

Kappe, Oliver et al, Synthesis and Flash Vacuum Pyrolysis of Isoxazolo-and Isothiazolo[5,4-d]pyrimidines, Heterocycles, 1994, 1615-1622, 37.

Kobayashi, Shigeru et al, The Synthesis and Xanthine Oxidase Inhibitory Activity of Pyrazolo[3,4-d]Pyrimidines, Chem. Phaim. Bull., 1973, 941-951, 21(5).

Ni, Zhang et al, Emerging Pharmacologic Therapies for Wet Age-Related Macular Degeneration, Ophthalmologica, 2009, 401-410, 223.

Remington's, Emulsifying and Suspending Agents, Remington's Pharmaceutical Sciences, 1990, 1304-1308, 18 Edition.

Stahl, Heinrich et al, Handbook of Pharmaceutical Salts: Properties, Selection, and Use, 2002, 324-325, International Union of Pure and Applied Chemistry.

Stommel, Jayne et al, Coactivation of Receptor Tyrosine Kinases Affects the Response of Tumor Cells to Targeted Therapies, Science, 2007, 287-290, 318.

T. Higuchi and V. Stella, Pro-drugs as Novel Delivery System, ACS Symposium Series; American Chemical Society, Jun. 1, 1975, the A.C.S. Symposium Series, p. 9 and p. 66 to 73., vol. 14, Washington, DC.

Van Tonder, Elsa et al, Preparation and Physicochemical Characterization of 5 Niclosamide Solvates and 1 Hemisolvate, AAPS PharmSciTech, 2004, 1-10, 5(1).

Zhang, Xinyuan et al, Vascular Endothelial Growth Factor-A: A Multifunctional Molecular Player in Diabetic Retinopathy, The International Journal of Biochemistry & Cell Biology, 2009, 2368-2371, 41.

* cited by examiner

3-PHENYL-5-UREIDOISOTHIAZOLE-4-CARBOXIMIDE AND 3-AMINO-5-PHENYLISOTHIAZOLE DERIVATIVES AS KINASE INHIBITORS

CROSS REFERENCE TO RELATED APPLICATIONS

This application claims the benefit of U.S. Provisional Application Ser. No. 61/581,031 filed Dec. 28, 2011, which is incorporated by reference herein in its entirety.

FIELD OF THE INVENTION

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

DESCRIPTION OF THE RELATED ART

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life. Sci., 2996, 63, 2608-2625 which is incorporated herein by reference.

There are a number of examples where RTK kinases, have been found to be involved in cellular signaling pathways leading to pathological conditions, including wet age-related macular degeneration (Ni et al. Opthalmologica 2009 223 401-410; Chappelow et al. Drugs 2008 68 1029-1036), diabetic retinopathy (Zhang et al Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105) and hyper immune response. In ophthalmic diseases such as neovascular age-related macular degeneration and diabetic retinopathy aberrant activation of VEGF receptors can lead to abnormal blood vessel growth. The importance of VEGFR signaling in the neovascular age-related macular degeneration disease process is evident by the clinical success of multiple anti-VEGF targeting agents including Lucentis®, Avastin®, and EYLEA™ (Barakat et al. Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as neovascular age-related macular degeneration and diabetic retinopathy the inhibition of both VEGFR and PDGFRβ may provide a greater therapeutic effect in by causing regression of existing neovascular blood vessels present in the disease (Adamis et al. Am. J. Pathol. 2006 168 2036-2053). In cancer inhibition of multiple RTK signaling pathways has been suggested to have a greater effect than inhibiting a single RTK pathway (DePinho et al. Science 2007 318 287-290; Bergers et al. J. Clin Invest. 2003 111 1287-1295).

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Certain small compounds are disclosed in PCT publication No. WO/1999/062890, PCT publication No. WO/2005/082001 and PCT publication No. WO/2006/026034 as useful for the treatment of diseases related to unregulated TKS transduction. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer; vascular (blood vessel) proliferative disorders such as diabetic retinopathy, age-related macular degeneration, retinopathy of prematurity, pterigium, arthritis and restenosis; fibrotic disorders such as hepatic cirrhosis and atherosclerosis; mesangial cell proliferative disorder such as glomerulonephritis, diabetic nephropathy, malignant nephrosclerosis, thrombotic microangiopathy syndromes, transplant rejection and glomerulopathies; metabolic disorders such as psoriasis, diabetes mellitus, wound healing, inflammation and neurodegenerative diseases.

In one illustrative embodiment, the compounds of the present invention are of Formula I:

Formula I $$R^2-L^1 \underset{O}{\overset{X^1-X^2}{\diagdown}}\phantom{xx}\text{(R}^1\text{)}_n \phantom{xx} L^2-R^3$$
$$\phantom{xxxxxx}NR_2$$

or a pharmaceutically acceptable salt thereof, wherein:

each of $X^1$ and $X^2$ is independently N or S, with the proviso that $X^1$ and $X^2$ are not simultaneously S;

$L^1$ is selected from the group consisting of —N(R)—, —N(R)—C(=O)—N(R)—, —O—C(=O)—N(R)—, —N(R)—C(=O)— and —C(=O)—N(R)—;

$L^2$ is selected from the group consisting of a covalent bond, —N(R)—, —N(R)—C(=O)—, —C(=O)—N(R)— and —N(R)—C(=O)—N(R)—;

each R independently is H or $C_{1-6}$ alkyl;

each $R^1$ independently is selected from the group consisting of $C_{1-6}$ alkyl, $C_{1-6}$ haloalkyl, halogen, and OR; or wherein two adjacent $R^1$ groups taken together with the carbon atoms to which they are attached form a six-membered aryl or a five- or six-membered heteroaryl;

n is 0, 1, or 2;

$R^2$ is selected from the group consisting of: a) H; b) $C_{1-6}$ alkyl that is unsubstituted or substituted with one or two substituents selected from the group consisting of heterocyclyl, —C(=O)OR, hydroxy, $C_{1-6}$ alkoxy, and aryl; and c)

$$\underset{O}{\diagup}\!\!\!\diagdown\!\!\!\underset{}{N}\text{—}\xi\text{—};$$

and $R^3$ is selected from the group consisting of H, hydroxy, —NO$_2$, aryl, and heteroaryl, wherein said aryl or heteroaryl is unsubstituted or substituted with one to three substituents selected from the group consisting of halo, $C_{1-6}$ haloalkyl, and $C_{1-6}$ alkyl.

In another embodiment, in formula I:

each of $X^1$ and $X^2$ is independently N or S;

$L^1$ is selected from the group consisting of —N(R)—C(=O)—N(R)—, —O—C(=O)—N(R)—, —N(R)—C(=O)— and —C(=O)—N(R)—;

$L^2$ is selected from the group consisting of a covalent bond, —N(R)—, —N(R)—C(=O)—, —C(=O)—N(R)— and —N(R)—C(=O)—N(R)—;

each R independently is H or $C_{1-6}$ alkyl;

each $R^1$ independently is selected from the group consisting of $C_{1-6}$ alkyl, $C_{1-6}$ haloalkyl, halogen, and OR; or wherein two adjacent $R^1$ groups taken together with the carbon atoms to which they are attached form a six-membered aryl or a five- or six-membered heteroaryl;

n is 0, 1, or 2;

$R^2$ is $C_{1-6}$ alkyl that is unsubstituted or substituted with one or two substituents selected from the group consisting of heterocyclyl, —C(=O)OR, hydroxy-$C_{1-6}$ alkyl-, and $C_{1-6}$ alkoxy; and $R^3$ is selected from the group consisting of H, —NO$_2$, aryl, and heteroaryl, wherein said aryl or heteroaryl is unsubstituted or substituted with one to three substituents selected from the group consisting of halo, $C_{1-6}$ haloalkyl, and $C_{1-6}$ alkyl.

In another embodiment, in Formula I, $X^1$ is N and $X^2$ is S.

In another embodiment, in Formula I, $X^1$ is S and $X^2$ is N.

In another embodiment, in Formula I, L' is selected from the group consisting of —N(H)—, —N(H)—C(=O)—, —N(H)—C(=O)—N(H)—, —O—C(=O)—N(H)—, —N(R)—C(=O)—, and —C(=O)—N(R)—.

In another embodiment, in Formula I, L' is selected from the group consisting of —N(H)—C(=O)—N(H)—, —O—C(=O)—N(H)—, —N(R)—C(=O)—, and —C(=O)—N(R)—.

In another embodiment, in Formula I, $L^2$ is selected from the group consisting of a covalent bond, —N(H)—, —N(H)—C(=O)—, —C(=O)—N(H)—, and —N(H)—C(=O)—N(H)—.

In another embodiment, in Formula I, n is 0 or 1.

In another embodiment, in Formula I, $R^2$ is selected from the group consisting of H, 2,4-dimethoxybenzyl, morpholinyl-(CH$_2$)$_3$—, HO—C(=O)—(CH$_2$)$_2$—, HO—C(=O)—(CH$_2$)$_3$—, CH$_3$O—C(=O)—(CH$_2$)$_2$—, CH$_3$O—C(=O)—(CH$_2$)$_3$—, HO—(CH$_2$)$_3$—, CH$_3$O—(CH$_2$)$_3$—, and ethyl.

In another embodiment, in Formula I, $R^2$ is selected from the group consisting of morpholinyl-(CH$_2$)$_3$—, HO—C(=O)—(CH$_2$)$_2$—, CH$_3$O—(CH$_2$)$_3$—, and ethyl.

In another embodiment, in Formula I, $R^3$ is selected from the group consisting of H, —NO$_2$, hydroxy, and aryl that is unsubstituted or substituted with one to two substituents selected from the group consisting of methyl, fluoro, and trifluoromethyl.

In another embodiment, in Formula I, $R^3$ is selected from the group consisting of H, —NO$_2$, and aryl that is unsubstituted or substituted with one to two substituents selected from the group consisting of methyl, fluoro, and trifluoromethyl.

In another embodiment, the compound of Formula I is represented by Formula IA:

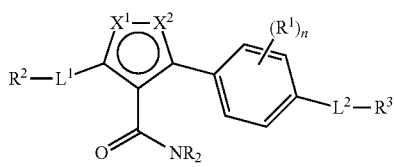

Formula IA wherein n, R¹, R², R³, L¹ and L² are as set forth for Formula I.

In another embodiment, the compound of Formula I is represented by Formula IB:

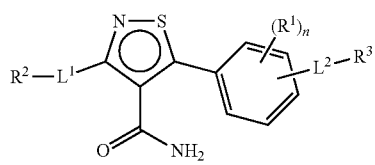

Formula IB wherein n is 0 or 1; and R¹, R², R³, L¹ and L² are as set forth for Formula I.

In another embodiment, the compound of Formula I is represented by Formula IC:

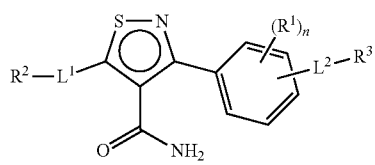

Formula IC wherein n is 0 or 1; and R¹, R², R³, L¹ and L² are as set forth for Formula I.

In another embodiment, in Formula IB:
L¹ is selected from the group consisting of —N(H)—, —N(H)—C(=O)—N(H)— and —O—C(=O)—N(H)—;
L² is selected from the group consisting of a covalent bond, —N(H)—, —N(H)—C(=O)— and —N(H)—C(=O)—N(H)—;
R¹ is methyl;
R² is selected from the group consisting of H, morpholinyl-(CH₂)₃—, HO—C(=O)—(CH₂)₂—, CH₃O—(CH₂)₃—, and ethyl; and
R³ is selected from the group consisting of H, —NO₂, and aryl that is unsubstituted or substituted with one to two substituents selected from the group consisting of methyl, fluoro, and trifluoromethyl.

In another embodiment, in Formula IB:
L¹ is selected from the group consisting of —N(H)—C(=O)—N(H)— and —O—C(=O)—N(H)—;
L² is selected from the group consisting of a covalent bond, —N(H)—, —N(H)—C(=O)— and —N(H)—C(=O)—N(H)—;
R¹ is methyl;
R² is selected from the group consisting of morpholinyl-(CH₂)₃—, HO—C(=O)—(CH₂)₂—, CH₃O—(CH₂)₃—, and ethyl; and
R³ is selected from the group consisting of H, —NO₂, and aryl that is unsubstituted or substituted with one to two substituents selected from the group consisting of methyl, fluoro, and trifluoromethyl.

In another embodiment, in Formula IC:
L¹ is selected from the group consisting of —N(H)—, —N(H)—C(=O)—, —N(H)—C(=O)—N(H)— and —O—C(=O)—N(H)—;
L² is selected from the group consisting of a covalent bond, —N(H)—, —N(H)—C(=O)— and —N(H)—C(=O)—N(H)—;
R¹ is methyl;
R² is selected from the group consisting of H,

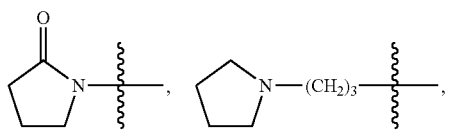

morpholinyl-(CH₂)₃—, HO—C(=O)—(CH₂)₂—, HO—C(=O)—(CH₂)₃—, CH₃O—C(=O)—(CH₂)₂—, CH₃O—C(=O)—(CH₂)₃—, HO—(CH₂)₃—, CH₃O—(CH₂)₃—, and ethyl; and
R³ is selected from the group consisting of H, hydroxy, —NO₂, and aryl that is unsubstituted or substituted with one to two substituents selected from the group consisting of methyl, fluoro, and trifluoromethyl.

In another embodiment, in Formula IC:
L¹ is selected from the group consisting of —N(H)—C(=O)—N(H)— and —O—C(=O)—N(H)—;
L² is selected from the group consisting of a covalent bond, —N(H)—, —N(H)—C(=O)— and —N(H)—C(=O)—N(H)—;
R¹ is methyl;
R² is selected from the group consisting of morpholinyl-(CH₂)₃—, HO—C(=O)—(CH₂)₂—, CH₃O—(CH₂)₃—, and ethyl; and
R³ is selected from the group consisting of H, —NO₂, and aryl that is unsubstituted or substituted with one to two substituents selected from the group consisting of methyl, fluoro, and trifluoromethyl.

In another embodiment, the compound of Formula IB is selected from the group consisting of:
5-{4-[3-(2-Fluoro-5-methyl-phenyl)-ureido]-phenyl}-3-[3-(3-morpholin-4-yl-propyl)-ureido]-isothiazole-4-carboxylic acid amide;
5-{4-[3-(2-Fluoro-5-methyl-phenyl)-ureido]-2-methyl-phenyl}-3-[3-(3-morpholin-4-yl-propyl)-ureido]-isothiazole-4-carboxylic acid amide;
3-[3-(4-Carbamoyl-5-{4-[3-(2-fluoro-5-methyl-phenyl)-ureido]-phenyl}-isothiazol-3-yl)-ureido]-propionic acid;
3-[3-(4-Carbamoyl-5-{4-[3-(2-fluoro-5-methyl-phenyl)-ureido]-2-methyl-phenyl}-isothiazol-3-yl)-ureido]-propionic acid;
3-[3-(3-Morpholin-4-yl-propyl)-ureido]-5-[4-(3-m-tolyl-ureido)-phenyl]-isothiazole-4-carboxylic acid amide;
5-[2-Methyl-4-(3-m-tolyl-ureido)-phenyl]-3-[3-(3-morpholin-4-yl-propyl)-ureido]-isothiazole-4-carboxylic acid amide;
3-(3-{4-Carbamoyl-5-[4-(3-m-tolyl-ureido)-phenyl]-isothiazol-3-yl}-ureido)-propionic acid;
3-(3-{4-Carbamoyl-5-[2-methyl-4-(3-m-tolyl-ureido)-phenyl]-isothiazol-3-yl}-ureido)-propionic acid;
5-{4-[3-(2-Fluoro-5-trifluoromethyl-phenyl)-ureido]-phenyl}-3-[3-(3-morpholin-4-yl-propyl)-ureido]-isothiazole-4-carboxylic acid amide;
5-{4-[3-(2-Fluoro-5-trifluoromethyl-phenyl)-ureido]-2-methyl-phenyl}-3-[3-(3-morpholin-4-yl-propyl)-ureido]-isothiazole-4-carboxylic acid amide;

3-[3-(4-Carbamoyl-5-{4-[3-(2-fluoro-5-trifluoromethyl-phenyl)-ureido]-phenyl}-isothiazol-3-yl)-ureido]-propionic acid;

3-[3-(4-Carbamoyl-5-{4-[3-(2-fluoro-5-trifluoromethyl-phenyl)-ureido]-2-methyl-phenyl}-isothiazol-3-yl)-ureido]-propionic acid;

3-(3-(3-Morpholin-4-yl-propyl)-ureido]-5-[4-(3-phenyl-ureido)-phenyl]-isothiazole-4-carboxylic acid amide;

3-(3-{4-Carbamoyl-5-[4-(3-phenyl-ureido)-phenyl]-isothiazol-3-yl}-ureido)-propionic acid;

3-(3-{4-Carbamoyl-5-[2-methyl-4-(3-phenyl-ureido)-phenyl]-isothiazol-3-yl}-ureido)-propionic acid;

3-(3-(3-Morpholin-4-yl-propyl)-ureido]-5-[4-(3-p-tolyl-ureido)-phenyl]-isothiazole-4-carboxylic acid amide;

5-[2-Methyl-4-(3-p-tolyl)-ureido)-phenyl]-3-[3-(3-morpholin-4-yl-propyl)-ureido]-isothiazole-4-carboxylic acid amide;

3-(3-{4-Carbamoyl-5-[2-methyl-4-(3-p-tolyl-ureido)-phenyl]-isothiazol-3-yl}-ureido)-propionic acid;

3-(3-{4-Carbamoyl-5-[4-(3-p-tolyl-ureido)-phenyl]-isothiazol-3-yl}-ureido)-propionic acid;

3-amino-5-[4-({[(2-fluoro-5-methylphenyl)amino]carbonyl}amino)phenyl]isothiazole-4-carboxamide;

5-[4-({[(2-fluoro-5-methylphenyl)amino]carbonyl}amino)phenyl]-3-[(3-morpholin-4-ylpropyl)amino]isothiazole-4-carboxamide; and 3-[(2,4-dimethoxybenzyl)amino]-5-[4-({[(2-fluoro-5-methylphenyl)amino]carbonyl}amino)phenyl]isothiazole-4-carboxamide; or a pharmaceutically acceptable salt thereof. The structures of these above compounds are set forth in Tables 2 and 3 below.

In another embodiment, the compound of Formula IC is selected from the group consisting of:

5-({[(3-morpholin-4-ylpropyl)amino]carbonyl}amino)-3-(4-nitrophenyl)isothiazole-4-carboxamide;

3-(4-aminophenyl)-5-({[(3-methoxypropyl)amino]carbonyl}amino)isothiazole-4-carboxamide;

5-({[(3-methoxypropyl)amino]carbonyl}amino)-3-(4-nitrophenyl)isothiazole-4-carboxamide;

3-[4-({[(2-fluoro-5-methylphenyl)amino]carbonyl}amino)phenyl]-5-({[(3-methoxypropyl)amino]carbonyl}amino)isothiazole-4-carboxamide;

ethyl {4-(aminocarbonyl)-3-[4-({[(2-fluoro-5-methylphenyl)amino]carbonyl}amino)phenyl]isothiazol-5-yl}carbamate;

3-[4-({[(2-fluoro-5-methylphenyl)amino]carbonyl}amino)phenyl]-5-({[(3-morpholin-4-ylpropyl)amino]carbonyl}amino)isothiazole-4-carboxamide;

3-{4-[3-(2-Fluoro-5-methyl-phenyl)-ureido]-2-methyl-phenyl}-5-[3-(3-morpholin-4-yl-propyl)-ureido]-isothiazole-4-carboxylic acid amide;

3-[3-(4-Carbamoyl-3-{4-[3-(2-fluoro-5-methyl-phenyl)-ureido]-phenyl}-isothiazol-5-yl)-ureido]-propionic acid;

3-[3-(4-Carbamoyl-3-{4-[3-(2-fluoro-5-methyl-phenyl)-ureido]-2-methyl-phenyl}-isothiazol-5-yl)-ureido]-propionic acid;

3-[4-({[(3-methylphenyl)amino]carbonyl}amino)phenyl]-5-({[(3-morpholin-4-ylpropyl)amino]carbonyl}amino)isothiazole-4-carboxamide;

3-[2-Methyl-4-(3-m-tolyl-ureido)-phenyl]-5-[3-(3-morpholin-4-yl-propyl)-ureido]-isothiazole-4-carboxylic acid amide;

3-(3-{4-Carbamoyl-3-[4-(3-m-tolyl-ureido)-phenyl]-isothiazol-5-yl}-ureido)-propionic acid;

3-(3-{4-Carbamoyl-3-[2-methyl-4-(3-m-tolyl-ureido)-phenyl]-isothiazol-5-yl}-ureido)-propionic acid;

3-{4-[({[2-fluoro-5-(trifluoromethyl)phenyl]amino}carbonyl)amino]phenyl}-5-({[(3-morpholin-4-ylpropyl)amino]carbonyl}amino)isothiazole-4-carboxamide;

3-{4-[3-(2-Fluoro-5-trifluoromethyl-phenyl)-ureido]-2-methyl-phenyl}-5-[3-(3-morpholin-4-yl-propyl)-ureido]-isothiazole-4-carboxylic acid amide;

3-[3-(4-Carbamoyl-3-{4-[3-(2-fluoro-5-trifluoromethyl-phenyl)-ureido]-phenyl}-isothiazol-5-yl)-ureido]-propionic acid;

3-[3-(4-Carbamoyl-3-{4-[3-(2-fluoro-5-trifluoromethyl-phenyl)-ureido]-2-methyl-phenyl}-isothiazol-5-yl)-ureido]-propionic acid;

3-{4-[(anilinocarbonyl)amino]phenyl}-5-({[(3-morpholin-4-ylpropyl)amino]carbonyl}amino)isothiazole-4-carboxamide;

3-[2-Methyl-4-(3-phenyl-ureido)-phenyl]-5-[3-(3-morpholin-4-yl-propyl)-ureido]-isothiazole-4-carboxylic acid amide;

3-(3-{4-Carbamoyl-3-[4-(3-phenyl-ureido)-phenyl]-isothiazol-5-yl}-ureido)-propionic acid;

3-(3-{4-Carbamoyl-3-[2-methyl-4-(3-phenyl-ureido)-phenyl]-isothiazol-5-yl}-ureido)-propionic acid;

3-(4-aminophenyl)-5-({[(3-morpholin-4-ylpropyl)amino]carbonyl}amino)isothiazole-4-carboxamide;

3-[4-({[(4-methylphenyl)amino]carbonyl}amino)phenyl]-5-({[(3-morpholin-4-ylpropyl)amino]carbonyl}amino)isothiazole-4-carboxamide;

3-[2-Methyl-4-(3-p-tolyl-ureido)-phenyl]-5-[3-(3-morpholin-4-yl-propyl)-ureido]-isothiazole-4-carboxylic acid amide;

3-(3-{4-Carbamoyl-3-[2-methyl-4-(3-p-tolyl-ureido)-phenyl]-isothiazol-5-yl}-ureido)-propionic acid;

3-(3-{4-Carbamoyl-3-[4-(3-p-tolyl-ureido)-phenyl]-isothiazol-5-yl}-ureido)-propionic acid;

5-({[(3-morpholin-4-ylpropyl)amino]carbonyl}amino)-3-(4-{[3-(trifluoromethyl)benzoyl]amino}phenyl)isothiazole-4-carboxamide;

3-(4-Nitro-phenyl)-5-[(2-oxo-pyrrolidine-1-carbonyl)-amino]-isothiazole-4-carboxylic acid amide;

3-(4-aminophenyl)-5-{[(2-oxopyrrolidin-1-yl)carbonyl]amino}isothiazole-4-carboxamide;

3-[4-({[(4-methylphenyl)amino]carbonyl}amino)phenyl]-5-{[(2-oxopyrrolidin-1-yl)carbonyl]amino}isothiazole-4-carboxamide;

4-{[({4-(aminocarbonyl)-3-[4-({[(4-methylphenyl)amino]carbonyl}amino)phenyl]isothiazol-5-yl}amino)carbonyl]amino}butanoic acid;

methyl 4-{[({4-(aminocarbonyl)-3-[4-({[(4-methylphenyl)amino]carbonyl}amino)phenyl]isothiazol-5-yl}amino)carbonyl]amino}butanoate;

4-[({[4-(aminocarbonyl)-3-(4-nitrophenyl)isothiazol-5-yl]amino}carbonyl)amino]butanoic acid;

methyl 4-[({[4-(aminocarbonyl)-3-(4-aminophenyl)isothiazol-5-yl]amino}carbonyl)amino]butanoate;

methyl 3-[({[4-(aminocarbonyl)-3-(4-nitrophenyl)isothiazol-5-yl]amino}carbonyl)amino]propanoate;

5-({[(3-hydroxypropyl)amino]carbonyl}amino)-3-(4-nitrophenyl)isothiazole-4-carboxamide;

3-[({[4-(aminocarbonyl)-3-(4-nitrophenyl)isothiazol-5-yl]amino}carbonyl)amino]propyl acetate;

3-[({[4-(aminocarbonyl)-3-(4-aminophenyl)isothiazol-5-yl]amino}carbonyl)amino]propyl acetate;

5-({[(3-hydroxypropyl)amino]carbonyl}amino)-3-[4-({[(4-methylphenyl)amino]carbonyl}amino)phenyl]isothiazole-4-carboxamide;

3-(4-aminophenyl)-5-({[(3-hydroxypropyl)amino]carbonyl}amino)isothiazole-4-carboxamide;
5-amino-3-(4-aminophenyl)isothiazole-4-carboxamide;
5-amino-3-[4-({[(4-methylphenyl)amino]carbonyl}amino)phenyl]isothiazole-4-carboxamide;
5-amino-3-[4-({[(2-fluoro-5-methylphenyl)amino]carbonyl}amino)phenyl]isothiazole-4-carboxamide;
5-amino-3-(3-nitrophenyl)isothiazole-4-carboxamide;
5-amino-3-(3-aminophenyl)isothiazole-4-carboxamide;
5-amino-3-[3-(hydroxyamino)phenyl]isothiazole-4-carboxamide;
5-amino-3-(3-{[3-(trifluoromethyl)benzoyl]amino}phenyl)isothiazole-4-carboxamide;
5-amino-3-{3-[(anilinocarbonyl)amino]phenyl}isothiazole-4-carboxamide;
3-(4-nitrophenyl)-5-({[(3-pyrrolidin-1-ylpropyl)amino]carbonyl}amino)isothiazole-4-carboxamide;
3-(4-aminophenyl)-5-({[(3-pyrrolidin-1-ylpropyl)amino]carbonyl}amino)isothiazole-4-carboxamide;
3-[4-({[(4-methylphenyl)amino]carbonyl}amino)phenyl]-5-({[(3-pyrrolidin-1-ylpropyl)amino]carbonyl}amino)isothiazole-4-carboxamide;
3-amino-5-[4-({[(2-fluoro-5-methylphenyl)amino]carbonyl}amino)phenyl]isothiazole-4-carboxamide;
5-[4-({[(2-fluoro-5-methylphenyl)amino]carbonyl}amino)phenyl]-3-[(3-morpholin-4-ylpropyl)amino]isothiazole-4-carboxamide; and
3-[(2,4-dimethoxybenzyl)amino]-5-[4-({[(2-fluoro-5-methylphenyl)amino]carbonyl}amino)phenyl]isothiazole-4-carboxamide;

or a pharmaceutically acceptable salt thereof. The structures of these above compounds are set forth in Tables 1 and 3 below.

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

Accordingly, the present invention also provides a method of inhibiting a receptor tyrosine kinase in a subject in need thereof, comprising administering to said subject a therapeutically effective amount of at least one compound of Formula I, or a pharmaceutically acceptable salt thereof.

In one embodiment, the receptor kinase is a VEGFR kinase.

In another embodiment, the VEGFR kinase VEGFR1 or VEGFR2 kinase.

In another embodiment, the receptor tyrosine kinase is a PDGFR kinase.

In another embodiment, the PDGFR kinase is a beta-type PDGFR (PDGFRb) kinase.

In another embodiment, the present invention provides a method for treating a disease related to unregulated tyrosine kinase signal transduction, comprising administering to a subject in need thereof a therapeutically effective amount of at least one compound of Formula I or a pharmaceutically acceptable salt thereof.

In another embodiment, the above disease is disease is selected from the group consisting of cancer, blood vessel proliferative disorders, fibrotic disorders, mesangial cell proliferative disorders and metabolic diseases.

In another embodiment, the blood vessel proliferative disorder is selected from the group consisting of diabetic retinopathy, age-related macular degeneration, retinopathy, of prematurity, pterigium, arthritis and restenosis.

In another embodiment, the fibrotic disorder is selected from the group consisting of hepatic cirrhosis and atherosclerosis.

In another embodiment, mesangial cell proliferative disorder is selected from the group consisting of glomerulonephritis, diabetic nephropathy, malignant nephrosclerosis, thrombotic microangiopathy syndromes, transplant rejection and glomerulopathies.

In another embodiment, the metabolic diseases is selected from the group consisting of psoriasis, diabetes mellitus, wound healing, inflammation and neurodegenerative diseases.

DETAILED DESCRIPTION OF THE INVENTION

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

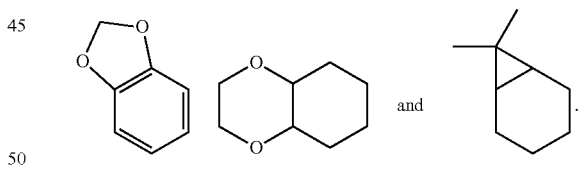

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. Example of such moiety is pyrrolidone:

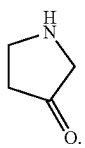

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. Example of such moiety is pyrrolidinone:

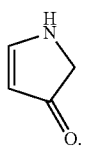

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

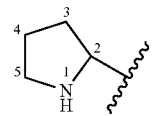

there is no —OH attached directly to carbons marked 2 and 5.

It should also be noted that tautomeric forms such as, for example, the moieties:

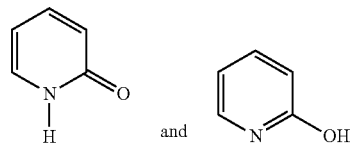 [SMILES: O=c1cccc[nH]1 ; Oc1ccccn1]

are considered equivalent in certain embodiments of this invention.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

The present invention further includes the compound of formula I in all its isolated forms. Thus, for example, the compound of Formula I is intended to encompass all forms of the compound such as, for example, any solvates, hydrates, stereoisomers, tautomers etc.

The present invention further includes the compound of formula I in its purified form.

It should also be noted that any carbon as well as heteroatom with unsatisfied valences in the text, schemes, examples and Tables herein is assumed to have the sufficient number of hydrogen atom(s) to satisfy the valences. And any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)$OY^1$ wherein $Y^1$ is H, $(C_1-C_6)$alkyl or benzyl, —C($OY^2$)$Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —C($Y^4$)$Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974. Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl and $^{123}$I, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. E.g., those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts, solvates, esters and prodrugs of the compounds of Formula I, are intended to be included in the present invention.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Scheme 1

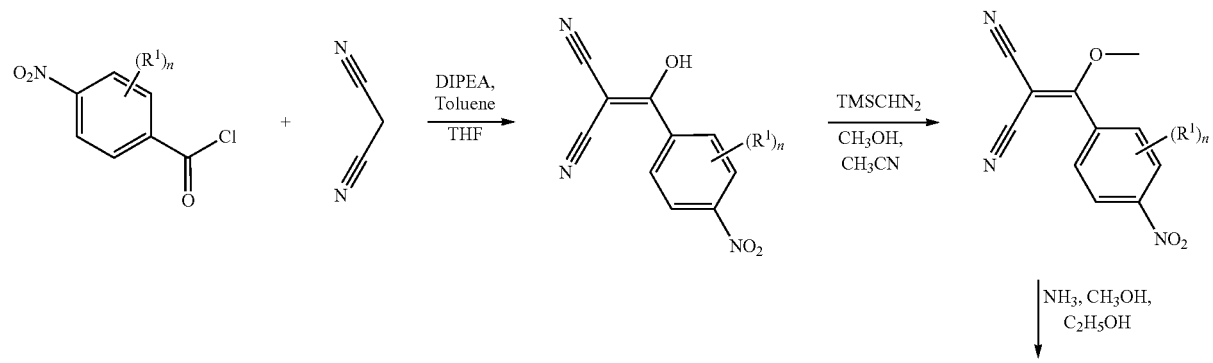

21
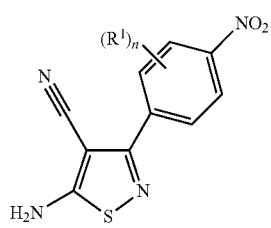
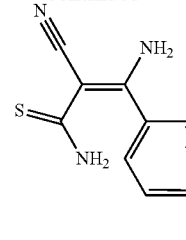
-continued
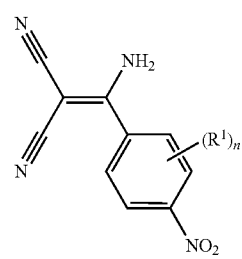
22
Scheme 2
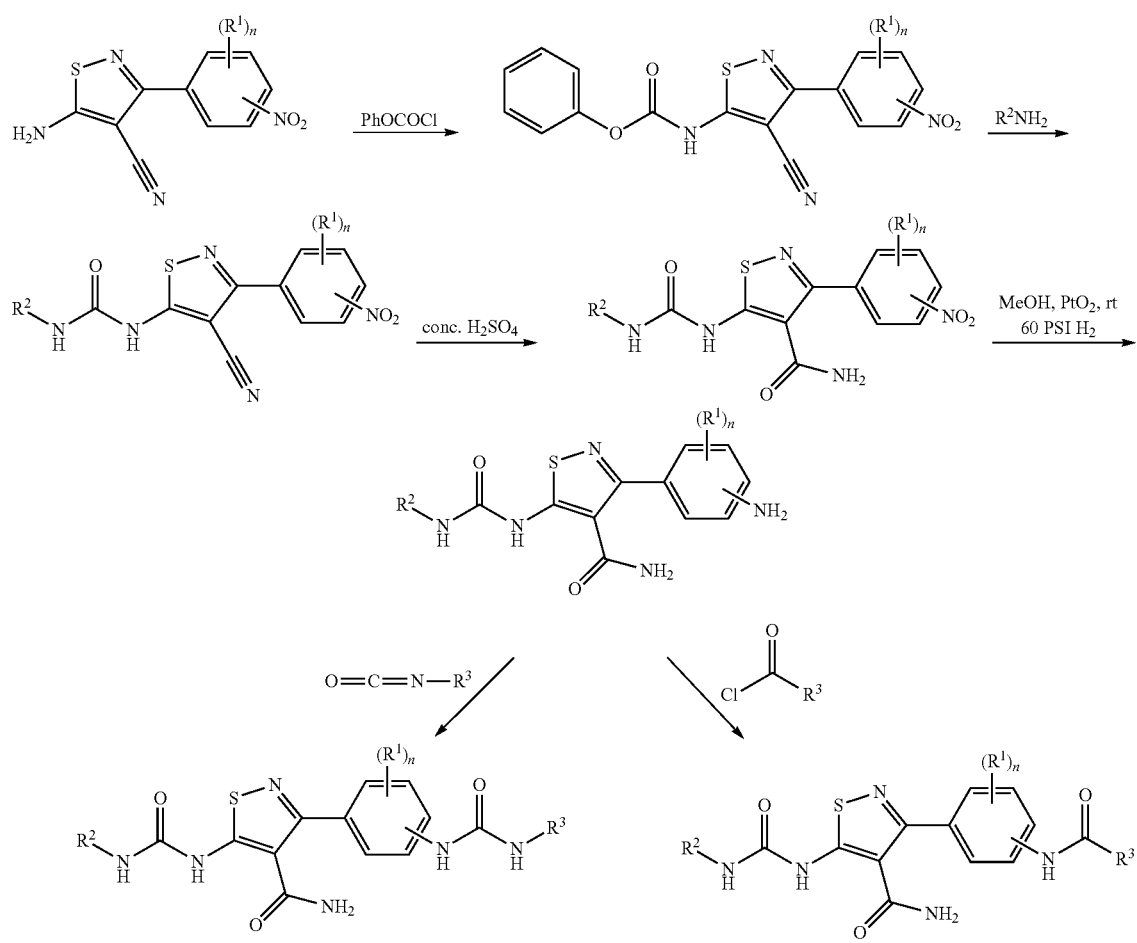
Scheme 3
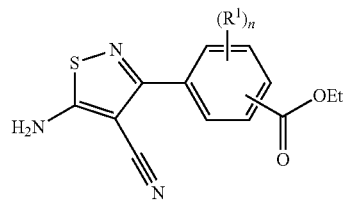
-continued
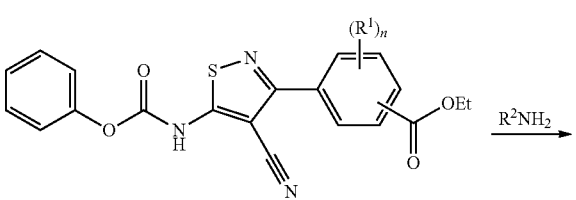

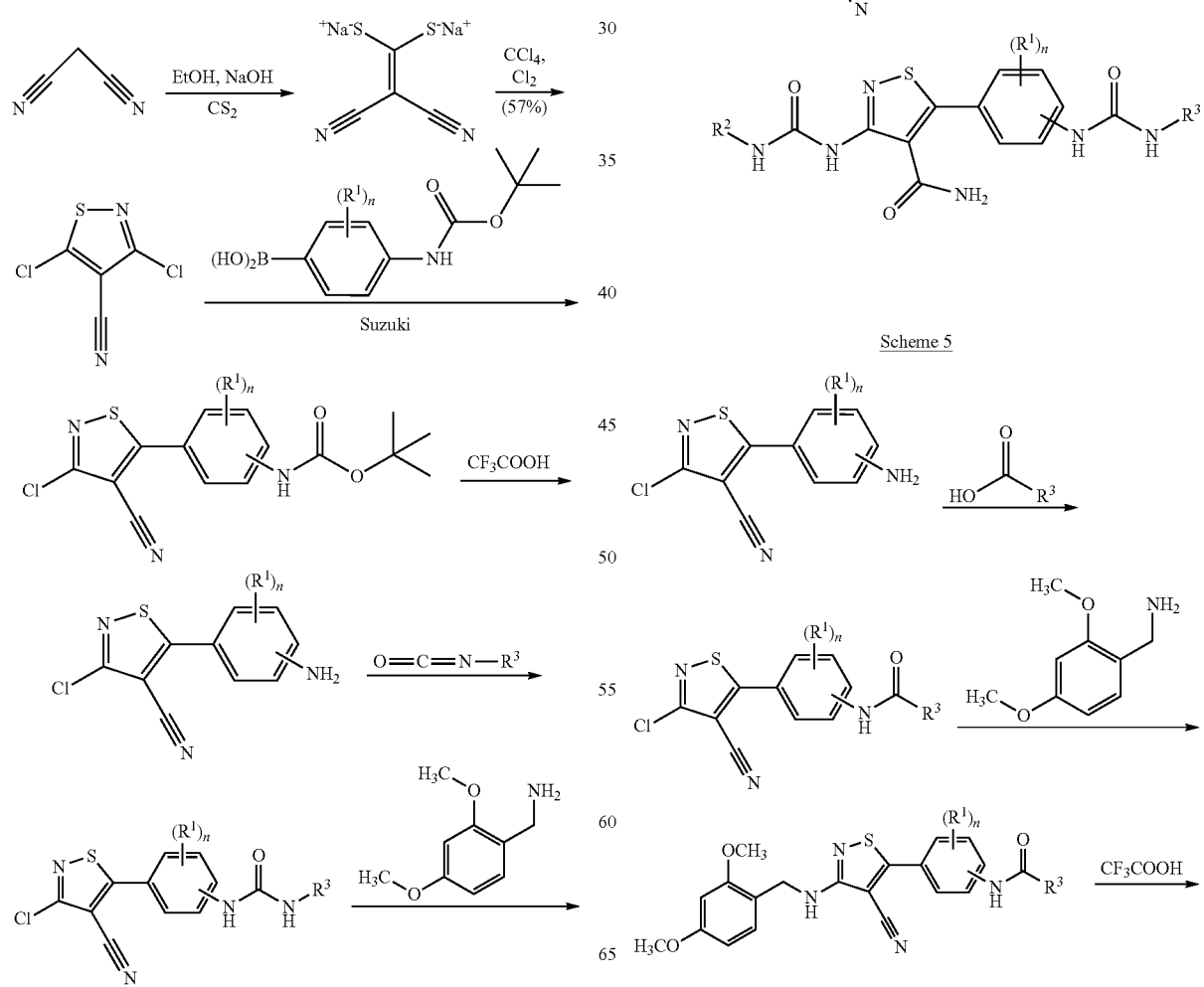

25

-continued

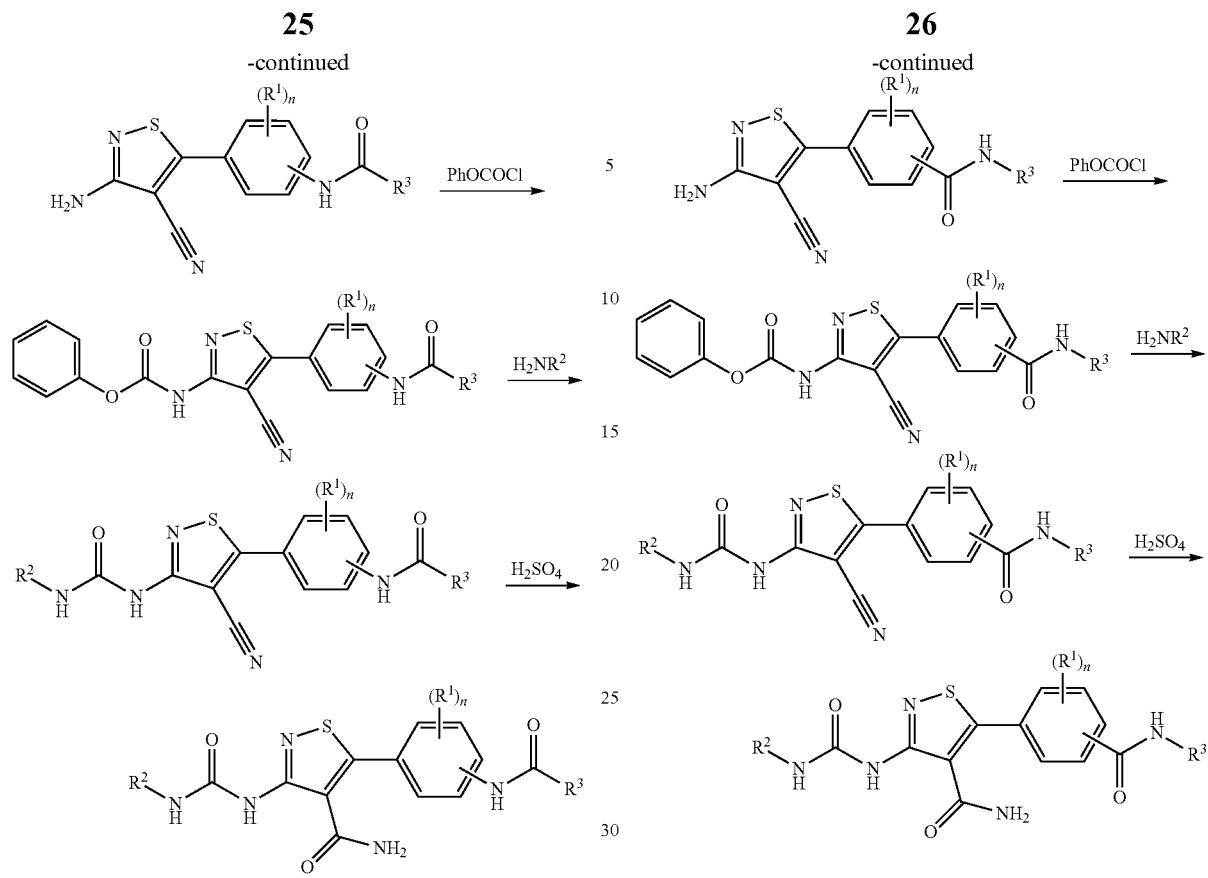

Scheme 6

26

-continued

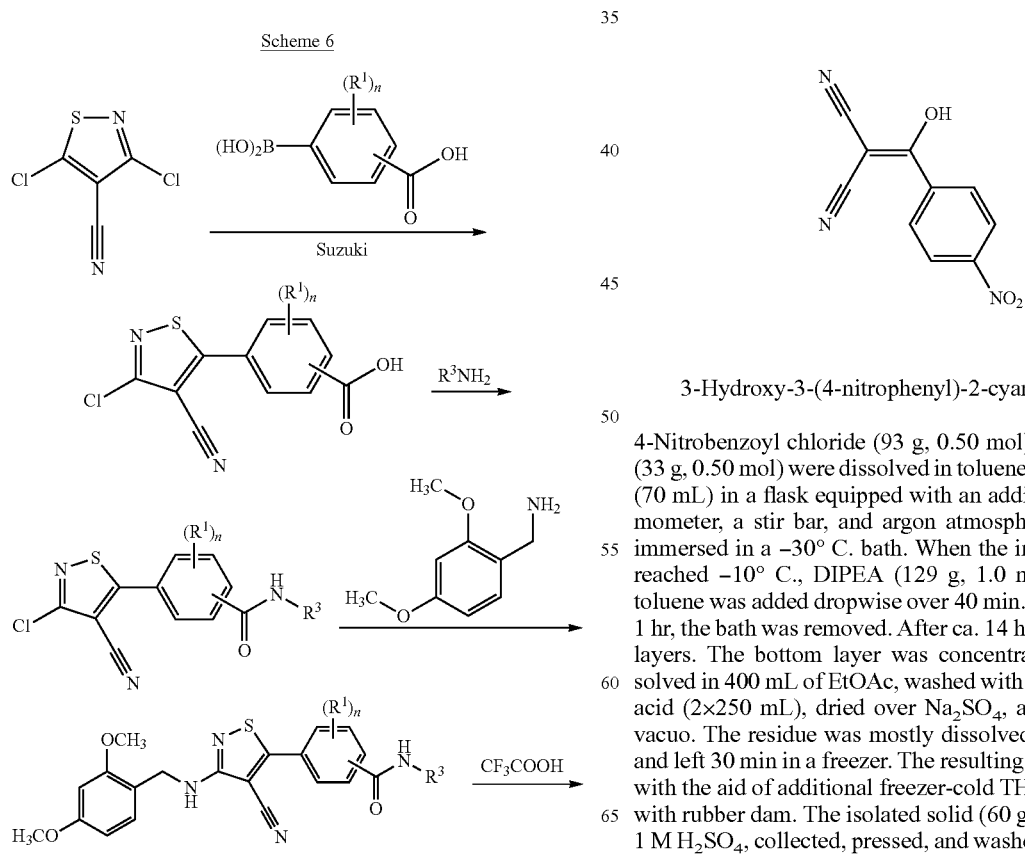

Preparation 1

3-Hydroxy-3-(4-nitrophenyl)-2-cyanoacrylonitrile

4-Nitrobenzoyl chloride (93 g, 0.50 mol) and malononitrile (33 g, 0.50 mol) were dissolved in toluene (400 mL) and THF (70 mL) in a flask equipped with an addition funnel, a thermometer, a stir bar, and argon atmosphere. The flask was immersed in a −30° C. bath. When the internal temperature reached −10° C., DIPEA (129 g, 1.0 mol) in 300 mL of toluene was added dropwise over 40 min. After an additional 1 hr, the bath was removed. After ca. 14 hr, the mixture had 2 layers. The bottom layer was concentrated in vacuo, dissolved in 400 mL of EtOAc, washed with 10% aqueous citric acid (2×250 mL), dried over $Na_2SO_4$, and concentrated in vacuo. The residue was mostly dissolved in THF (100 mL) and left 30 min in a freezer. The resulting solid was collected with the aid of additional freezer-cold THF and pressed well with rubber dam. The isolated solid (60 g) was suspended in 1 M $H_2SO_4$, collected, pressed, and washed with water. After drying, the solid weighed 36 g. This solid was dissolved in EtOAc (400 mL), washed with 1 M H$_2$SO$_4$ (200 mL) and water (200 mL), filtered through phase separation paper, and concentrated. The solid residue was reconcentrated successively from dichloromethane and toluene and dried at high vacuum. At this stage, 25 g were isolated. The HPLC purity was 94%. Analysis of a 60 MHz NMR spectrum showed about 18 mol % DIPEA. The material was used in the next step without further purification.

Another 15 g portion of solid of 95% HPLC purity but containing 30 mol % DIPEA was eventually isolated from the THF filtrate. This material was set aside. The estimated overall yield of the reaction was about 42% NMR (60 MHz) (CDCl$_3$) δ 8.0 (AB, 4H)

Preparation 2

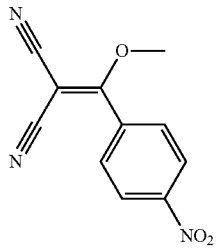 [SMILES: COC(=C(C#N)C#N)c1ccc([N+](=O)[O-])cc1]

3-Methoxy-3-(4-nitrophenyl)-2-cyanoacrylonitrile

3-Hydroxy-3-(4-nitrophenyl)-2-cyanoacrylonitrile (21.5 g, 0.10 mol) was dissolved in acetonitrile (430 mL) and of methanol (43 mL) in a flask equipped with a dropping funnel, a thermometer, a stir bar, and argon atmosphere. The flask was immersed in a −15° C. bath to the level that the internal temperature was maintained between −5° C. and 0° C. (75 mL of a 2.0 M solution in diethyl ether, 0.15 mol) was added dropwise over 20 min. HPLC analysis showed incomplete reaction, and an additional portion (25 mL, 0.05 mol) of trimethylsilyldiazomethane solution was added. This was repeated with 35 mL (0.07 mol). After 20 min, the mixture was poured into a rapidly-stirred solution of acetic acid (15 g, 0.25 mol) in EtOAc (1.8 L). The mixture was extracted with water (3×1.5 L), filtered through phase separation paper, and concentrated in vacuo. the solid residue weighed 14.4 g and was used in the next step without further purification. NMR (60 MHz) (CDCl$_3$) δ 8.0 (AB, 4H); 4.0 (s, 3H).

Preparation 3

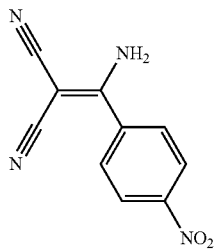 [SMILES: N#CC(C#N)=C(N)c1ccc([N+](=O)[O-])cc1]

3-Amino-3-(4-nitrophenyl)-2-cyanoacrylonitrile

3-Methoxy-3-(4-nitrophenyl)-2-cyanoacrylonitrile (14.4 g, 0.063 mol) was suspended in ethanol (1 L) in a flask equipped with a magnetic stirrer. To the suspension was added 60 mL (ca. 0.20 mol) of a 10% (w/w) solution of ammonia in methanol. The mixture was stirred vigorously for 15 min, at which time HPLC analysis showed the absence of starting material. The now homogeneous mixture was concentrated in vacuo to ca. 80 mL. The solid that had formed was collected with the aid of a small amount of additional ethanol and was pressed well with rubber dam. The cake was washed with of ethanol (2×5 mL) and was left to dry in a hood draft. The dry solid weighed 8.8 g. The filtrate was concentrated and mixed with dichloromethane (10 mL). The resulting solid was collected, washed with dichloromethane (2×2 mL), dried, and combined with the 1st crop to yield 9.9 g (46% for 2 steps). HPLC analysis indicated a purity of 91%. NMR (60 MHz) (DMSO-d6) δ 8.8 (bs, 0.5H); 8.0 (AB, 4H); 3.2 (bs, 1H); 2.8 (bs, 0.5H). The IR spectrum showed nitrile stretches at 2221 and 2207 cm$^{-1}$.

Preparation 4

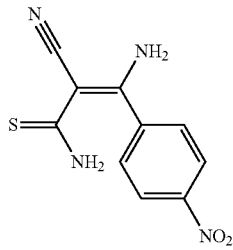 [SMILES: N#C/C(C(N)=S)=C(\N)c1ccc([N+](=O)[O-])cc1]

3-Amino-3-(4-nitrophenyl)-2-thioformamidoacrylonitrile

3-Amino-3-(4-nitrophenyl)-2-cyanoacrylonitrile (8.8 g, 0.052 mol) was suspended in ethanol (60 mL) and water (60 mL) in a flask equipped with a stir bar, a reflux condenser, and an argon atmosphere. After diethyl dithiophosphate (13.3 g, 0.083 mol) was added, the mixture was placed in a 100° C. bath for ca. 14 hr. HPLC analysis indicted incomplete reaction, and an additional portion of diethyl dithiophosphate (2.6 g, 0.014 mol) was added. After 4 hr, the mixture was poured into 1.2 L of ice/water (rapid stirring).

After this suspension had stirred for 40 min, the solid was collected, pressed with rubber dam, and washed with of water (100 mL). The dried solid weighed ca. 8.8 g (ca. 88%). The HPLC purity was 97%. NMR (60 MHz) (DMSO-d6) δ 8.6 (bs 1H); 8.0 (AB, 4H); 8.2 (bs, 1H); 7.8 (bs, 1H); 3.3 (bs, 1H). The IR spectrum exhibited a single nitrile stretch at 2191 cm$^{-1}$.

Preparation 5

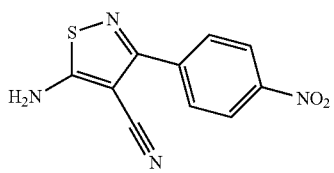 [SMILES: N#Cc1c(-c2ccc([N+](=O)[O-])cc2)nsc1N]

5-Amino-3-(4-nitrophenyl)isothiazole-4-carbonitrile

3-Amino-3-(4-nitrophenyl)-2-thioformamidoacrylonitrile (10.0 g, 0.040 mol) and 30% hydrogen peroxide (9.1 g, 0.08 mol) were mixed with ethanol (50 mL) in a flask equipped with a stir bar and an argon atmosphere. The mixture was stirred vigorously without splashing material on the sides of the flask. After 14 hr, HPLC analysis showed only 50% conversion, and an additional portion of hydrogen peroxide (9.1 g, 0.08 mol) and ethanol (30 mL) were added. After 8 hr, the mixture was poured into rapidly stirring ice/water (250 mL). After the suspension had stirred for 20 min, the solid was collected. This solid was dried to constant weight in an hood draft to yield 9.3 g (95%). HPLC analysis indicated a purity of 97%. NMR (60 MHz) (DMSO-d6/CD3OD) δ 8.2 (AB, 4H); 4.1 (s, 2H). The nitrile stretch has moved to 2216 cm$^{-1}$ Preparation 6

Phenyl [4-cyano-3-(4-nitrophenyl)isothiazol-5-yl] carbamate

To a mixture of 5-amino-3-(4-nitrophenyl)isothiazole-4-carbonitrile (394 mg, 1.60 mmol), N,N-diisopropylethylamine (0.836 mL, 4.8 mmol), and catalytic DMAP in 20 mL 1,2-dichloroethane at rt was added phenyl chloroformate (0.301 mL, 2.40 mmol) drop wise over 1 minute. The reaction mixture was stirred at rt for 22 hours, then added directly to a dry packed silica gel column eluting with CHCl$_3$, then gradient 10% to 50% EtOAc in CHCl$_3$. The title compound was obtained as a beige solid (131 mg, 22%) and used as is for the next step.

$^1$H NMR (DMSO+D$_2$O) δ: 8.33-8.39 (m, 2H), 8.12-8.17 (m, 2H), 7.36-7.44 (m, 2H), 7.14-7.25 (m, 3H)

Preparation 7

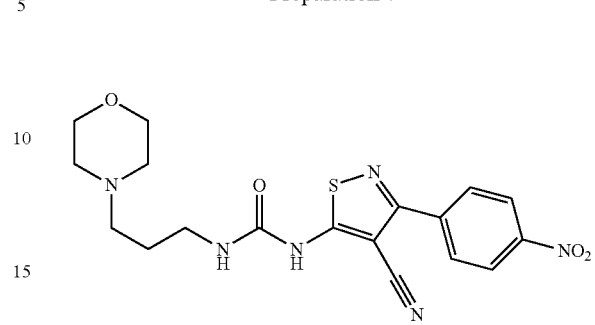

1-[4-cyano-3-(4-nitrophenyl)isothiazol-5-yl]-3-(3-morpholin-4-ylpropyl)urea

A mixture of phenyl (4-cyano-3-(4-nitrophenyl)isothiazol-5-yl)carbamate (37 mg, 0.10 mmol) and 3-morpholinopropylamine (0.021 mL, 0.14 mmol) in 0.8 mL dioxane was heated at 80° C. After 2 hours the reaction mixture was evaporated to a yellowish oily film. This material was then chromatographed eluting with EtOAc, then gradient 2% to 6% MeOH in EtOAc to give the title compound as a pale yellow solid (33 mg, 80%). $^1$H NMR (acetone) δ: 8.38-8.44 (m, 2H), 8.22-8.27 (m, 2H), 6.91 (t, J=5.4 Hz, 1H), 3.59-3.64 (m, 4H), 3.38-3.45 (m, 2H), 2.37-2.45 (m, 6H), 1.77 (quin, J=6.8 Hz, 2H)

Example 1

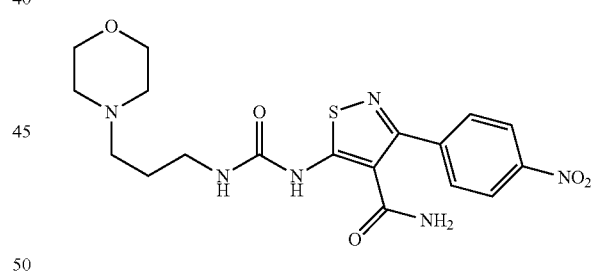

5-({[(3-morpholin-4-ylpropyl)amino]carbonyl}amino)-3-(4-nitrophenyl)isothiazole-4-carboxamide A mixture of 1-(4-cyano-3-(4-nitrophenyl)isothiazol-5-yl)-3-(3-morpholinopropyl)urea (113 mg, 0.27 mmol) in 3.5 mL conc. H$_2$SO$_4$ was heated at 45° C. After 1.5 hours the reaction mixture was quenched into 100 mL ice water giving a white gel-like solid. The aqueous solution was made basic using Na$_2$CO$_3$ and then extracted with EtOAc, the EtOAc layer washed with brine, dried with anhydrous Na$_2$SO$_4$ and rotary evaporated giving the title compound as a light beige solid (118 mg, 100%).

$^1$H NMR (acetone) δ: 10.58 (br. s., 1H), 8.31-8.36 (m, 2H), 7.88-7.94 (m, 2H), 7.50 (br. s., 1H), 3.59-3.64 (m, 4H), 3.39 (td, J=6.7, 5.6 Hz, 2H), 2.41-2.45 (m, 2H), 2.37-2.41 (m, 4H), 1.76 (quin, J=6.8 Hz, 2H)

Example 2

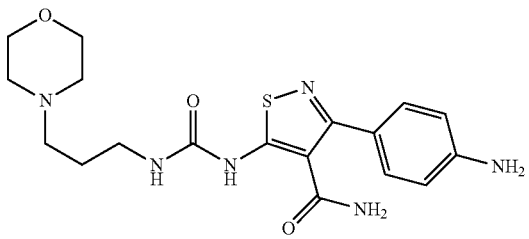 [SMILES: NC(=O)c1c(-c2ccc(N)cc2)nsc1NC(=O)NCCCN1CCOCC1]

3-(4-aminophenyl)-5-({[(3-morpholin-4-ylpropyl)amino]carbonyl}amino)isothiazole-4-carboxamide A mixture of 5-(3-(3-morpholinopropyl)ureido)-3-(4-nitrophenyl)isothiazole-4-carboxamide (110 mg, 0.25 mmol) and platinum oxide (25 mg, 0.11 mmol) in 15 mL MeOH was hydrogenated under 60 PSI hydrogen. After 16.5 hours, the mixture was filtered and rotary evaporated to an off-white solid. Then an additional 16 mg of impure product from another reaction was combined and this material chromatographed eluting with gradient 5% to 15% MeOH in CHCl$_3$ to give the title compound as an off-white solid (47 mg, 40%).

$^1$H NMR (acetone) δ: 10.97 (br. s., 1H), 7.47 (br. s., 1H), 7.22-7.27 (m, 2H), 6.72-6.78 (m, 2H), 6.69 (br. s., 1H), 5.86 (br. s., 1H), 5.00 (s, 2H), 3.59-3.63 (m, 4H), 3.37 (td, J=6.7, 5.6 Hz, 2H), 2.41-2.45 (m, 2H), 2.36-2.41 (m, 4H), 1.75 (quin, J=6.8 Hz, 2H)

Example 3

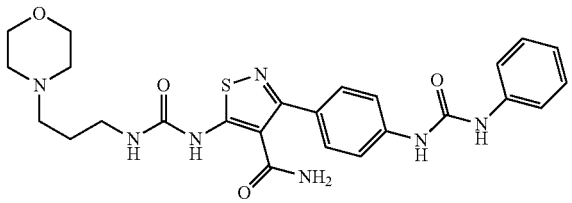 [SMILES: NC(=O)c1c(-c2ccc(NC(=O)Nc3ccccc3)cc2)nsc1NC(=O)NCCCN1CCOCC1]

3-{4-[(anilinocarbonyl)amino]phenyl}-5-({[(3-morpholin-4-ylpropyl)amino]carbonyl}amino)isothiazole-4-carboxamide A mixture of 3-(4-aminophenyl)-5-(3-(3-morpholinopropyl)ureido)isothiazole-4-carboxamide (12 mg, 0.030 mmol), N,N-diisopropylethylamine (0.021 mL, 0.120 mmol), and phenyl isocyanate (0.0056 mL, 0.051 mmol) in 1.0 mL THF was stirred at rt for 19 hours. The reaction was quenched with 0.2 mL aqueous Na$_2$CO$_3$ solution, stirred 5 min at rt, and then partitioned between EtOAc and aqueous Na$_2$CO$_3$ solution, the EtOAc layer washed with H$_2$O, brine, dried with anhydrous Na$_2$SO$_4$ and rotary evaporated to a white solid. The solid was chromatographed eluting with CHCl$_3$, then gradient 2.5% to 10% MeOH in CHCl$_3$. The resulting solid was subjected to an EtOAc/NaHCO$_3$ work-up to remove the presence of any silica gel impurity. Upon evaporation of the EtOAc layer the title compound was obtained as a white solid (12 mg, 77%).

$^1$H NMR (acetone) δ: 10.89 (br. s., 1H), 8.37 (s, 1H), 8.21 (s, 1H), 7.65-7.70 (m, 2H), 7.53-7.58 (m, 2H), 7.46-7.52 (m, 3H), 7.25-7.32 (m, 2H), 6.96-7.03 (m, 1H), 6.66-6.83 (m, 1H), 5.86 (br. s., 1H), 3.59-3.64 (m, 4H), 3.34-3.42 (m, 2H), 2.42-2.46 (m, 2H), 2.37-2.41 (m, 4H), 1.76 (quin, J=6.8 Hz, 2H)

Example 4

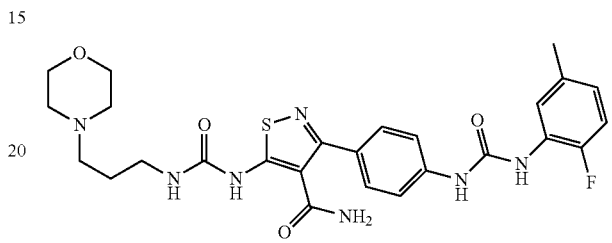

3-[4-({[(2-fluoro-5-methylphenyl)amino]carbonyl}amino)phenyl]-5-({[(3-morpholin-4-ylpropyl)amino]carbonyl}amino)isothiazole-4-carboxamide In a manner similar to that described for Example 3,3-(4-aminophenyl)-5-(3-(3-morpholinopropyl)ureido)isothiazole-4-carboxamide (8 mg, 0.020 mmol) and 2-fluoro-5-methylphenyl isocyanate (0.0029 mL, 0.022 mmol) was used to give the title compound as a white solid (6 mg, 58%).

$^1$H NMR (acetone) δ: 10.88 (br. s., 1H), 8.72 (s, 1H), 8.14 (dd, J=7.8, 2.2 Hz, 1H), 8.02 (d, J=2.9 Hz, 1H), 7.66-7.71 (m, 2H), 7.45-7.54 (m, 3H), 7.02 (dd, J=11.3, 8.4 Hz, 1H), 6.79-6.86 (m, 1H), 6.69-6.79 (m, 1H), 5.87 (br. s., 1H), 3.59-3.64 (m, 4H), 3.34-3.42 (m, 2H), 2.41-2.46 (m, 2H), 2.37-2.41 (m, 4H), 2.32 (s, 3H), 1.76 (quin, J=6.8 Hz, 2H)

Example 5

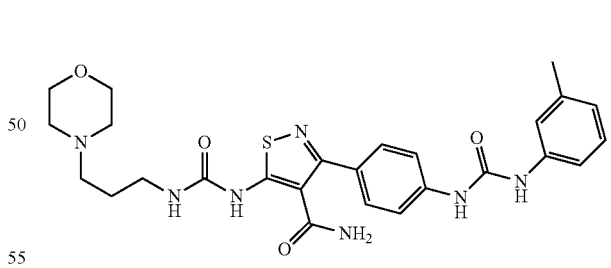

3-[4-({[(3-methylphenyl)amino]carbonyl}amino)phenyl]-5-({[(3-morpholin-4-ylpropyl)amino]carbonyl}amino)isothiazole-4-carboxamide In a manner similar to that described for Example 3,3-(4-aminophenyl)-5-(3-(3-morpholinopropyl)ureido)isothiazole-4-carboxamide (12 mg, 0.030 mmol), 3 drops N,N-diisopropylethylamine, and meta-tolyl isocyanate (0.0056 mL, 0.045 mmol) was used to give the title compound as a white solid (13 mg, 83%).

$^1$H NMR (acetone) δ: 10.89 (br. s., 1H), 8.35 (s, 1H), 8.14 (s, 1H), 7.64-7.69 (m, 2H), 7.44-7.54 (m, 3H), 7.38-7.40 (m, 1H), 7.31-7.36 (m, 1H), 7.16 (t, J=7.8 Hz, 1H), 6.80-6.85 (m, 1H), 6.68-6.79 (m, 1H), 5.86 (br. s., 1H), 3.60-3.64 (m, 4H), 3.34-3.42 (m, 2H), 2.42-2.47 (m, 2H), 2.38-2.43 (m, 4H), 2.30 (s, 3H), 1.76 (quin, J=6.7 Hz, 2H)

Example 6

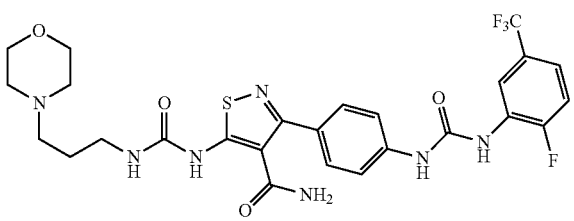 [SMILES: NC(=O)c1c(-c2ccc(NC(=O)Nc3cc(C(F)(F)F)ccc3F)cc2)nsc1NC(=O)NCCCN1CCOCC1]

3-{4-[({[2-fluoro-5-(trifluoromethyl)phenyl]amino}carbonyl)amino]phenyl}-5-({[(3-morpholin-4-ylpropyl)amino]carbonyl}amino)isothiazole-4-carboxamide In a manner similar to that described for Example 3 (, 3-(4-aminophenyl)-5-(3-(3-morpholinopropyl)ureido)isothiazole-4-carboxamide (12 mg, 0.030 mmol), 3 drops N,N-diisopropylethylamine, and 2-fluoro-5-(trifluoromethyl)phenyl isocyanate (0.0087 mL, 0.060 mmol) was used to give the title compound as a white solid (11 mg, 62%).

$^1$H NMR (acetone) δ: 10.87 (br. s., 1H), 8.89 (s, 1H), 8.76-8.81 (m, 1H), 8.45 (d, J=2.6 Hz, 1H), 7.66-7.72 (m, 2H), 7.47-7.56 (m, 3H), 7.36-7.45 (m, 2H), 6.66-6.83 (m, 1H), 5.86 (br. s., 1H), 3.59-3.64 (m, 4H), 3.34-3.42 (m, 2H), 2.41-2.46 (m, 2H), 2.37-2.41 (m, 4H), 1.76 (quin, J=6.7 Hz, 2H)

Example 7

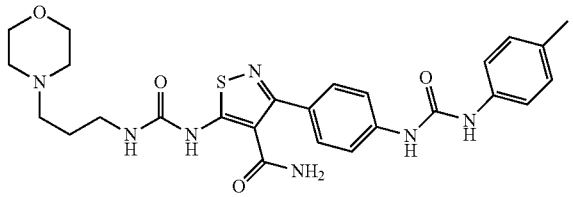 [SMILES: Cc1ccc(NC(=O)Nc2ccc(-c3nsc(NC(=O)NCCCN4CCOCC4)c3C(N)=O)cc2)cc1]

3-[4-({[(4-methylphenyl)amino]carbonyl}amino)phenyl]-5-({[(3-morpholin-4-ylpropyl)amino]carbonyl}amino)isothiazole-4-carboxamide In a manner similar to that described for Example 3,3-(4-aminophenyl)-5-(3-(3-morpholinopropyl)ureido)isothiazole-4-carboxamide (12 mg, 0.030 mmol), N,N-diisopropylethylamine (0.021 mL, 0.120 mmol), and para-tolyl isocyanate (0.0068 mL, 0.054 mmol) was used to give the title compound as a white solid (11 mg, 70%).

$^1$H NMR (CD$_3$OD) δ: 7.55-7.60 (m, 2H), 7.47-7.52 (m, 2H), 7.28-7.34 (m, 2H), 7.09-7.14 (m, 2H), 3.67-3.73 (m, 4H), 3.30-3.34 (m, 2H), 2.41-2.52 (m, 6H), 2.30 (s, 3H), 1.78 (quin, J=7.2 Hz, 2H)

Preparation 7

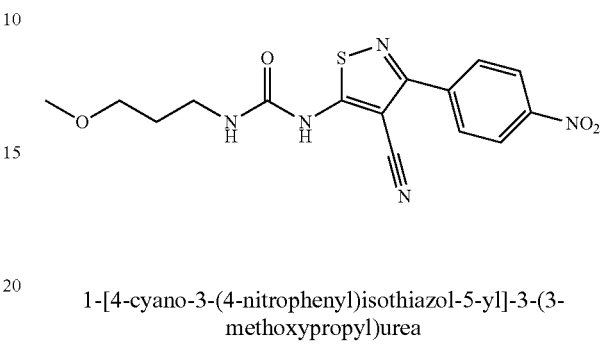

1-[4-cyano-3-(4-nitrophenyl)isothiazol-5-yl]-3-(3-methoxypropyl)urea

A mixture of phenyl (4-cyano-3-(4-nitrophenyl)isothiazol-5-yl)carbamate (37 mg, 0.10 mmol) and 3-methoxypropylamine (0.015 mL, 0.15 mmol) in 0.8 mL dioxane was heated at 80° C. After 2 hours the reaction mixture was evaporated to a solid film. The solid was triturated with dichloromethane and then 10% EtOAc in hexane to give a yellow-orange solid. This material was then chromatographed eluting with gradient 50% to 70% EtOAc in hexane. The filtrate from trituration and material from another reaction were combined and chromatographed with EtOAc/hexane. The clean product lots were combined to give the title compound as an off-white solid (27 mg).

$^1$H NMR (acetone) δ: 10.04 (br. s, 1H), 8.38-8.44 (m, 2H), 8.22-8.28 (m, 2H), 6.90 (s, 1H), 3.47 (t, J=6.0 Hz, 2H), 3.39-3.46 (m, 2H), 3.29 (s, 3H), 1.83 (quin, J=6.3 Hz, 2H)

Example 8

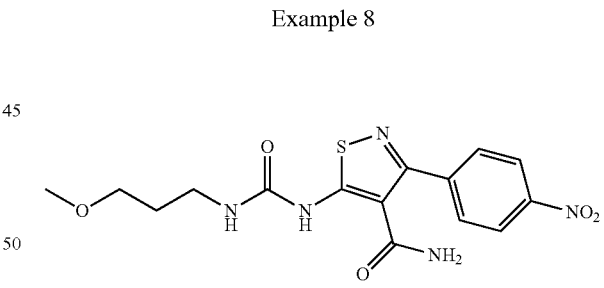

5-({[(3-methoxypropyl)amino]carbonyl}amino)-3-(4-nitrophenyl)isothiazole-4-carboxamide A mixture of 1-(4-cyano-3-(4-nitrophenyl)isothiazol-5-yl)-3-(3-methoxypropyl)urea (12 mg, 0.032 mmol) in 0.8 mL conc. H$_2$SO$_4$ was heated at 45° C. After 1.5 hours the reaction was quenched into 25 mL water containing brine. The aqueous solution was adjusted to pH=1 using saturated NaHCO$_3$ and then extracted with EtOAc, the EtOAc layer washed with brine, dried with anhydrous Na$_2$SO$_4$ and rotary evaporated to a solid. The solid was recrystallized from acetonitrile giving the title compound as a white solid (4 mg, 29%).

¹H NMR (acetone) δ: 10.54 (br. s, 1H), 8.31-8.36 (m, 2H), 7.88-7.93 (m, 2H), 7.40 (br. s, 1H), 3.45 (t, J=6.2 Hz, 2H), 3.36-3.43 (m, 2H), 3.28 (s, 3H), 1.82 (quin, J=6.4 Hz, 2H)

Example 9

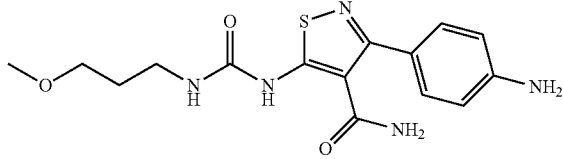 [SMILES: COCCCNC(=O)Nc1snc(-c2ccc(N)cc2)c1C(N)=O]

3-(4-aminophenyl)-5-({[(3-methoxypropyl)amino]carbonyl}amino)isothiazole-4-carboxamide A mixture of 5-(3-(3-methoxypropyl)ureido)-3-(4-nitrophenyl)isothiazole-4-carboxamide (4 mg, 0.009 mmol) and catalytic platinum oxide in 4 mL MeOH was hydrogenated under 60 PSI hydrogen. After 17 hours, the mixture was filtered and rotary evaporated to a white solid. The solid was partitioned between EtOAc and aqueous NaHCO₃ solution, the EtOAc layer dried with anhydrous Na₂SO₄ and evaporated to the title compound as a white solid (2 mg, 66%).

¹H NMR (acetone) δ: 10.93 (br. s, 1H), 7.36 (br. s, 1H), 7.22-7.27 (m, 2H), 6.72-6.78 (m, 2H), 6.67 (br. s, 1H), 5.86 (br. s, 1H), 5.00 (br. s., 2H), 3.44 (t, J=6.2 Hz, 2H), 3.33-3.41 (m, 2H), 3.27 (d, J=0.6 Hz, 3H), 1.81 (quin, J=6.4 Hz, 2H)

Example 10

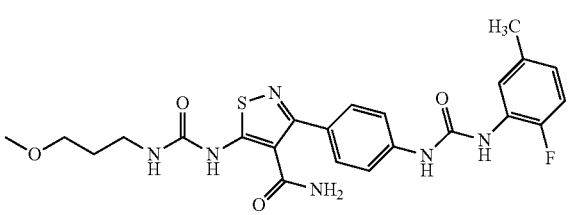 [SMILES: COCCCNC(=O)Nc1snc(-c2ccc(NC(=O)Nc3cc(C)ccc3F)cc2)c1C(N)=O]

3-[4-({[(2-fluoro-5-methylphenyl)amino]carbonyl}amino)phenyl]-5-({[(3-methoxypropyl)amino]carbonyl}amino)isothiazole-4-carboxamide In a manner similar to that described for Example 3,3-(4-aminophenyl)-5-(3-(3-methoxypropyl)ureido)isothiazole-4-carboxamide and 2-fluoro-5-methylphenyl isocyanate may be converted to the title compound.

Example 11

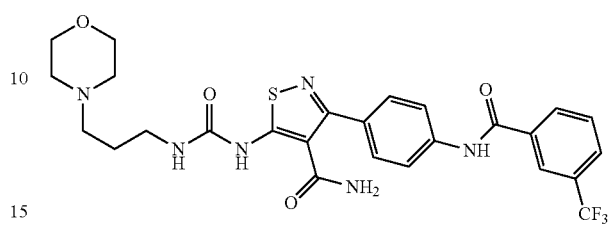

5-({[(3-morpholin-4-ylpropyl)amino]carbonyl}amino)-3-(4-{[3-(trifluoromethyl)benzoyl]amino}phenyl)isothiazole-4-carboxamide To a mixture of 3-(4-aminophenyl)-5-(3-(3-morpholinopropyl)ureido)isothiazole-4-carboxamide (6 mg, 0.015 mmol) and N,N-diisopropylethylamine (0.0078 mL, 0.045 mmol) in 0.8 mL THF at rt was added 3-(trifluoromethyl)benzoyl chloride (0.0024 mL, 0.017 mmol). The reaction was stirred at rt for 2 hours, then quenched with aqueous Na₂CO₃ solution, stirred 5 min at rt, and then partitioned between EtOAc and aqueous Na₂CO₃ solution, the EtOAc layer washed with H₂O, brine, dried with anhydrous Na₂SO₄ and rotary evaporated. The solid was chromatographed eluting with CHCl₃, then gradient 2.5% to 10% MeOH in CHCl₃. The resulting solid was subjected to an EtOAc/NaHCO₃ work-up to remove the presence of any silica gel impurity. Upon evaporation of the EtOAc layer the title compound was obtained as a white solid (7 mg, 76%).

¹H NMR (acetone) δ: 10.86 (br. s., 1H), 9.99 (s, 1H), 8.30-8.35 (m, 2H), 7.93-8.00 (m, 3H), 7.76-7.84 (m, 1H), 7.52-7.63 (m, 3H), 6.82 (br. s., 1H), 5.90 (br. s., 1H), 3.59-3.64 (m, 4H), 3.34-3.42 (m, 2H), 2.41-2.45 (m, 2H), 2.36-2.41 (m, 4H), 1.76 (quin, J=6.7 Hz, 2H)

Preparation 8

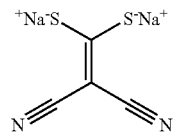

Sodium 2,2-dicyanoethene-1,1-bis(thiolate)

Solid NaOH (187.2 g, 4541 mmol) was added to EtOH (2000.0 mL, 34253 mmol) at rt and stirred until disolved. The solution was cooled to 15° C. and malononitrile (150 g, 2300 mmol) was added in one portion and the resulting suspension was stirred until the malononitrile had dissolved (reaction is slightly endothermic). The reaction mixture was stirred for 1 h and carbon disulfide (136.6 mL, 2271 mmol) was added while keeping the temperature between 10 and 20° C. After about half of the carbon disulfide was added the reaction mixture begins to solidify and becomes very difficult to stir. The addition of carbon disulfide was continued and the reaction was stirred mechanically with a spatula. When the addition was complete the reaction mixture was warmed to 30° C. and then cooled to room temperature. The product was filtered and dried under vacuum at 82° C. for 2 days. The solid material obtained was ground up with a mortar and pestal and then dried under vacuum to give the title compound (335 grams, 79%).

Preparation 9

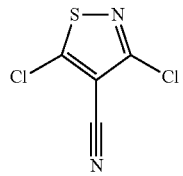

3,5-dichloroisothiazole-4-carbonitrile

A suspension of sodium 2,2-dicyanoethene-1,1-bis(thiolate) (40 grams, 0.21 mol) was suspended in CCl₄ (250 mL) at rt. The reaction mixture was sparged with Cl₂ gas (approximately 2 equivalents) which caused the reaction mixture to reach reflux. The reaction mixture was filtered and concentrated. This procedure was repeated four addition times with 41, 44, 45, and 50 grams of sodium 2,2-dicyanoethene-1,1-bis(thiolate). The reaction products were combined and kugelrohr distilled. The distillate was recrystallized from heptanes to provide the title compound (50 gram, 0.288 mol).

Preparation 10

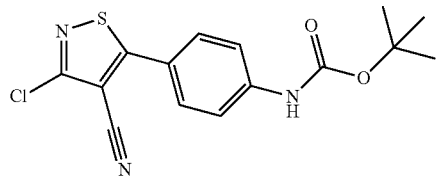 [SMILES: CC(C)(C)OC(=O)Nc1ccc(-c2snc(Cl)c2C#N)cc1]

tert-Butyl 4-(3-chloro-4-cyanoisothiazol-5-yl)phenylcarbamate

A mixture of 3,5-dichloroisothiazole-4-carbonitrile (5.37 g, 30 mmol), 4-(tertbutoxycarbonylamino)phenylboronic acid (14.22 g, 60 mmol), potassium fluoride (6.11 g, 105 mmol), 18-crown-6 (3.96 g, 15 mmol), and palladium acetate (337 mg, 1.5 mmol) in toluene (250 ml) was heated at reflux for 6 hours. The reaction was cooled to RT and the mixture was diluted with water and EtOAc. Layers were separated and the aqueous layer was extracted with EtOAc×3. The combined organics was washed with brine and dried with MgSO₄, filtered, and concentrated. The crude product was purified by flash silica gel column eluted with 5-15% EtOAc in hexanes to obtain the above compound as a white crystalline solid (8.55 g, 85%). NMR and MS spectra are consistent with the structure. HPLC purity 97.6%.

Preparation 11

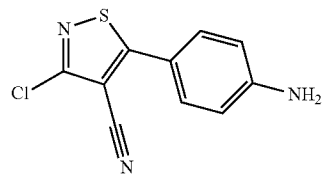 [SMILES: N#Cc1c(Cl)nsc1-c1ccc(N)cc1]

5-(4-Aminophenyl)-3-chloroisothiazole-4-carbonitrile

A solution of tert-Butyl 4-(3-chloro-4-cyanoisothiazol-5-yl) phenylcarbamate (4.76 g, 13.38 mmol) in DCM (100 ml) was treated with 10 mL of TFA. The reaction mixture was stirred at RT overnight. Solvent was removed in vacuo. The residue was diluted with water and DCM (100 ml). Layers were separated and the aqueous layer was extracted with DCM×2. The combined organics was washed with brine and dried with MgSO₄, filtered, and concentrated. Product was rinsed with Et₂O/hexanes and collected by filtration as a bright yellow solid (3.15 g, 94%).

Preparation 12

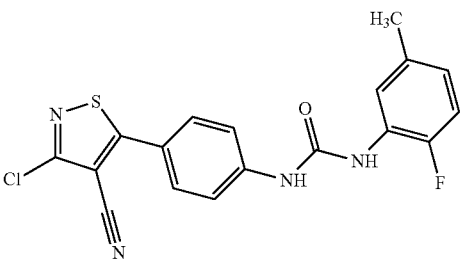 [SMILES: Cc1ccc(F)c(NC(=O)Nc2ccc(-c3snc(Cl)c3C#N)cc2)c1]

1-[4-(3-chloro-4-cyanoisothiazol-5-yl)phenyl]-3-(2-fluoro-5-methylphenyl)urea

A solution of 5-(4-Aminophenyl)-3-chloroisothiazole-4-carbonitrile (4.565 g, 19.4 mmol) and 2-fluoro-5-methylphenyl isocyanate (5.85 g, 38.7 mmol) in 100 mL of dry THF was heated to reflux overnight. TLC indicated presence of considerable amount of starting material. Additional 2 g of 2-fluoro-5-methylphenyl isocyanate was added and the reaction was continued for another 24 h. The reaction was cooled to RT. THF was removed in vacuo and the resulting solid was stirred in 200 mL of Et$_2$O for 1 h. Product was collected by filtration and washed with Et$_2$O/hexanes to afford a light yellow solid (6.78 g, 90%).

Preparation 13

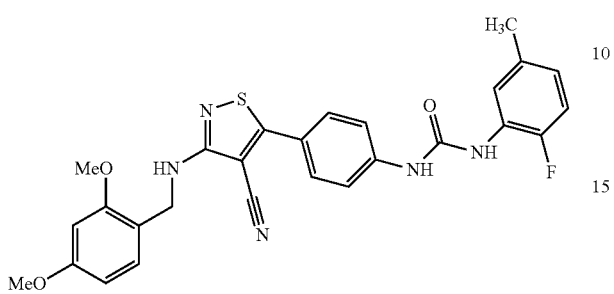

1-(4-{4-cyano-3-[(2,4-dimethoxybenzyl)amino]
isothiazol-5-yl}phenyl)-3-(2-fluoro-5-methylphenyl)
urea A suspension of 1-[4-(3-chloro-4-cyanoisothiazol-5-yl)phenyl]-3-(2-fluoro-5-methylphenyl)urea (4.3 g, 11.1 mmol) in 15 mL of 2,4-dimethoxybenzylamine was heated to 73° C. for 24 h. The reaction became clear after ~3 h. The reaction was cooled to RT. The residue was diluted with 300 mL of DCM and was washed with 10% HCl solution two times, saturated Na$_2$S$_2$O$_5$ two times followed by brine. The organic solution was dried with MgSO$_4$, filtered, and concentrated. The crude product was purified by flash silica gel column eluted with 2-5% MTBE in DCM/hexanes (2:1) to obtain the title compound as a light yellow solid (1.19 g, 21%).

Preparation 14

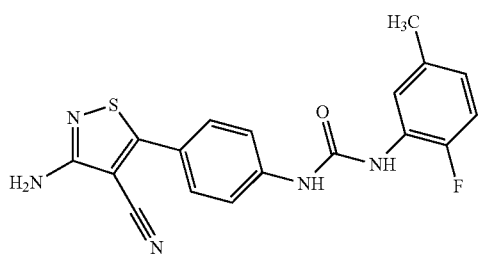 [SMILES: Cc1ccc(F)c(NC(=O)Nc2ccc(-c3snc(N)c3C#N)cc2)c1]

1-[4-(3-amino-4-cyanoisothiazol-5-yl)phenyl]-3-(2-
fluoro-5-methylphenyl)urea

A suspension of 1-(4-{4-cyano-3-[(2,4-dimethoxybenzyl)amino]isothiazol-5-yl}phenyl)-3-(2-fluoro-5-methylphenyl)urea (593 mg, 1.15 mmol) in 50 mL of DCM was treated with 1.5 mL of TFA. Solid was dissolved and the reaction turned to yellow and then red in color. TLC indicated the completion of the reaction in <30 min. Saturated Na$_2$CO$_3$ solution was added and the mixture was stirred for 30 min. Layers were separated and the aqueous layer was extracted with DCM×3. The combined organics was washed with brine and dried with MgSO$_4$, filtered, and concentrated. The crude product was redissolved in 100 mL of EtOAc. Insoluble impurity was filtered through celite and washed with EtOAc. Filtrate was concentrated in vacuo to afford the product as a cream solid (398 mg, 94%).

Preparation 15

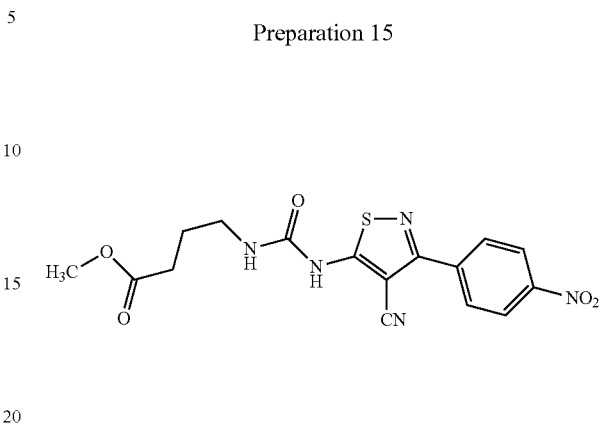

Methyl 4-[({[4-cyano-3-(4-nitrophenyl)isothiazol-5-
yl]amino}carbonyl)amino]butanoate A solution of 5-amino-3-(4-nitrophenyl)isothiazole-4-carbonitrile (25.0 g, 0.101 mol) in tetrahydrofuran (300 mL) dimethylsulfoxide (40 mL) at ambient temperature was treated with potassium carbonate (35.0 g, 0.25 mol). The resulting mixture was stirred at ambient temperature for 15 min. The reaction mixture was treated with 4-isocyanatobutyric acid methyl ester (21.8 g, 0.15 mol) at ambient temperature. The mixture was stirred at ambient temperature overnight. The reaction mixture was filtered through celite and filtrate concentrated in vacuo. The residue was dissolved EtOAc (600 mL) and washed with water and brine then dried (sodium sulfate), filtered, solvent concentrated in vacuo. The crude residue was purified by column chromatography (20% ethyl acetate in dichloromethane) to give the title compound as a light brown solid (31.5 g, 78%).

Example 45

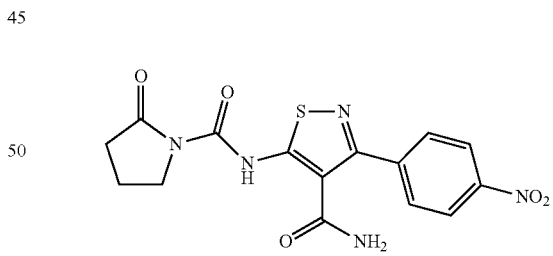

3-(4-Nitro-phenyl)-5-[(2-oxo-pyrrolidine-1-carbo-
nyl)-amino]-isothiazole-4-carboxylic acid amide Methyl 4-[({[4-cyano-3-(4-nitrophenyl)isothiazol-5-yl]amino}carbonyl)amino]butanoate (10.0 g) was added portion wise to concentrated sulfuric acid (50.0 mL) at ambient temperature over 20 min. The resulting suspension was heated to 45° C. over 90 min. The reaction mixture was cooled to ambient temperature. The reaction mixture was poured into ice water (600 ml), stirred for 30 min. The solid which formed was collected and washed with water then dried in vacuo to give the titlee compound as off white solid (10.2 g, 99%).

Example 46

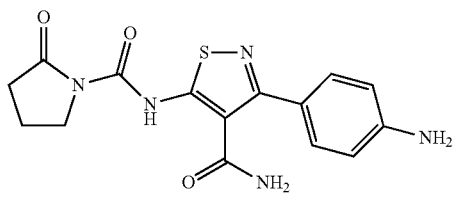

3-(4-Aminophenyl)-5-{[(2-oxopyrrolidin-1-yl)carbonyl]amino}isothiazole-4-carboxamide 3-(4-Nitro-phenyl)-5-[(2-oxo-pyrrolidine-1-carbonyl)-amino]-isothiazole-4-carboxylic acid amide (10.2 g,) and 10% palladium on carbon (2 g) in tetrahydrofuran (300 mL) and dimethylformamide (50 mL) was hydrogenated at 80 psi over 24 hr in metal bomb. The catalyst was removed by filtration through celite and washed with tetrahydrofuran. The filtrate was concentrated in vacuo to give an off white solid, which was stirred in ether (150 mL) and filtered to give the title compound as a off white solid (8.7 g, 94%).

Example 47

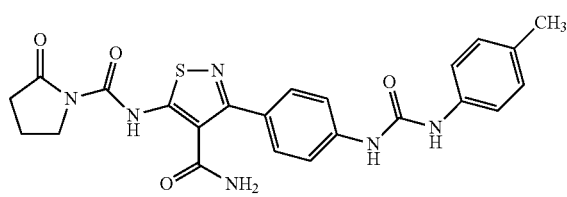 [SMILES: Cc1ccc(NC(=O)Nc2ccc(-c3nsc(NC(=O)N4CCCC4=O)c3C(N)=O)cc2)cc1]

3-[4-({[(4-Methylphenyl)amino]carbonyl}amino)phenyl]-5-{[(2-oxopyrrolidin-1-yl)carbonyl]amino}isothiazole-4-carboxamide A solution of 3-(4-aminophenyl)-5-{[(2-oxopyrrolidin-1-yl)carbonyl]amino}isothiazole-4-carboxamide (9.6 g, 0.027 mol), diisopropylethylamine (5.3 g, 0.046 mol) in dimethylformamide (150 mL) at ambient temperature was treated with para-Tolyl isocyanate (4.0 g 0.03 mol) over 20 minute period. The resulting mixture was stirred at ambient temperature for 2 hr. The reaction mixture was concentrated in vacuo to give an off white solid, which was stirred in EtOAc (150 mL), filtered the solid and washed with EtOAc to give the title compound as a white solid (11.8 g, 88%).

Example 48

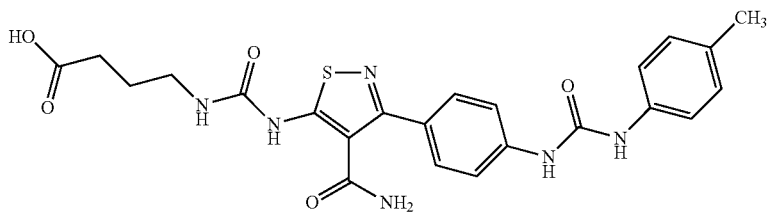 [SMILES: Cc1ccc(NC(=O)Nc2ccc(-c3nsc(NC(=O)NCCCC(=O)O)c3C(N)=O)cc2)cc1]

4-{[({4-(Aminocarbonyl)-3-[4-({[(4-methylphenyl)amino]carbonyl}amino)phenyl]isothiazol-5-yl}amino)carbonyl]amino}butanoic acid 3-[4-({[(4-methylphenyl)amino]carbonyl}amino)phenyl]-5-{[(2-oxopyrrolidin-1-yl)carbonyl]amino}isothiazole-4-carboxamide (11.8 g,) was added to 1 N sodium hydroxide (100 mL) at ambient temperature. The resulting mixture was stirred at ambient temperature for overnight (reaction mixture became clear solution). Reaction mixture acidified with 2 N HCl. The solid which formed was collected by filtration and washed with water then dried in vacuo to give the title compound as off white solid (9.1 g, 75%).

ESI-MS: Calc. for $C_{23}H_{25}N_6O_5{}_2S$ (M+H)$^+$: 497.5, found. 497.2

Example 49

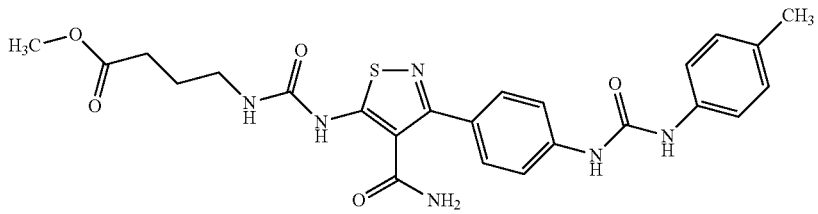

43

Methyl 4-{[({4-(aminocarbonyl)-3-[4-({[(4-methylphenyl)amino]carbonyl}amino) phenyl]isothiazol-5-yl}amino)carbonyl]amino}butanoate A mixture of methyl 4-[({[4-(aminocarbonyl)-3-(4-aminophenyl)isothiazol-5-yl]amino}carbonyl)amino]butanoate (121 mg, 0.321 mmol), N,N-diisopropylethylamine (0.14 mL, 0.80 mmol), and para-tolyl isocyanate (0.053 mL, 0.42 mmol) in 4.0 mL dioxane was reacted at room temperature for 21 hours. The reaction was quenched with 1 mL MeOH, stirred 5 min a troom temperature, and then evaporated. The resulting solid residue was triturated with EtOAc to give 159 mg of an off-white solid. To this material was added 51 mg of an impure lot from another reaction, and the combined lots triturated with acetonitrile/MeOH, again triturated with acetonitrile to give a white solid. This material was recrystallized from CHCl$_3$/MeOH/EtOAc mixture to give 89 mg of white solid. The impure filtrate lots were then chromatographed eluting with CHCl$_3$/EtOAc plus 5% MeOH and the resulting product triturated with acetonitrile to give an additional 56 mg of clean product. The lots were combined giving the title compound as a white solid (145 mg, combined yield 67%).

$^1$H NMR (DSMO-d6) δ: 10.23 (s, 1H), 8.79 (s, 1H), 8.60 (s, 1H), 7.80 (t, J=5.6 Hz, 1H), 7.59 (br. s., 1H), 7.47-7.54 (m, 4H), 7.32-7.37 (m, 2H), 7.09 (d, J=8.2 Hz, 2H), 6.71 (br. s., 1H), 3.60 (s, 3H), 3.13-3.20 (m, 2H), 2.36 (t, J=7.5 Hz, 2H), 2.25 (s, 3H), 1.72 (quin, J=7.1 Hz, 2H)

Example 50

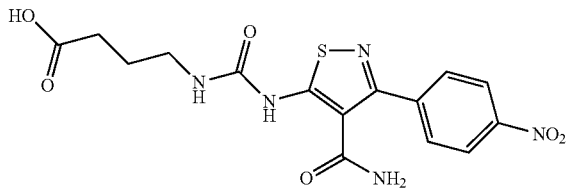 [SMILES: NC(=O)c1c(-c2ccc([N+](=O)[O-])cc2)nsc1NC(=O)NCCCC(=O)O]

4-[({[4-(Aminocarbonyl)-3-(4-nitrophenyl)isothiazol-5-yl]amino}carbonyl)amino]butanoic acid 3-(4-Nitro-phenyl)-5-[(2-oxo-pyrrolidine-1-carbonyl)-amino]-isothiazole-4-carboxylic acid amide (12.5 g) added to 1 N sodium hydroxide (250 mL) at ambient temperature. The resulting mixture was stirred at ambient temperature for overnight (reaction mixture clear solution). Reaction mixture acidified with 2 N HCl. The solid which formed was collected by filtration and washed with water then dried in vacuo to give the title compound as off white solid (11.5 g, 88%).

Example 51

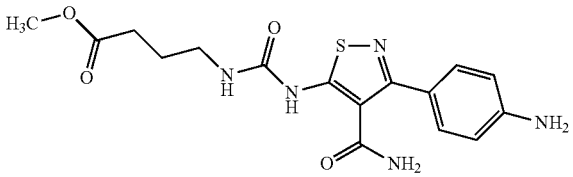 [SMILES: COC(=O)CCCNC(=O)Nc1snc(-c2ccc(N)cc2)c1C(N)=O]

44

Methyl 4-[({[4-(aminocarbonyl)-3-(4-aminophenyl)isothiazol-5-yl]amino}carbonyl)amino]butanoate Dimethylsulfate (4.4 g, 0.035 mol) was added to a solution of 4-[({[4-(aminocarbonyl)-3-(4-nitrophenyl)isothiazol-5-yl]amino}carbonyl)amino]butanoic acid (11.5 g, 0.029 mol) and potassium carbonate (6.0 g 0.043 mol) in dimethylformamide (250 mL) at ambient temperature over 20 min. The resulting mixture was stirred at ambient temperature for overnight. The reaction mixture was filtered, filtrate was concentrated in vacuo. Residue taken in ethyl acetate (300 mL) and washed with water and brine dried on sodium sulfate. Solvent concentrated in vacuo, gave yellow solid (10.4 g). Crude solid used in next step. The crude solid (9.5 g) and 10% palladium on carbon (2 g) in tetrahydrofuran (300 mL) and dimethylformamide (50 mL) was hydrogenated at 80 psi over 24 hr in metal bomb. The catalyst was removed by filtration throught celite and washed with tetrahydrofuran. The filtrate was concentrated in vacuo to give off white solid, which was stirred in ether (150 mL) and filtered to give the title compound as a off white solid (8.5 g, 96%).

ESI-MS: Calc. for C$_{16}$H$_{20}$N$_5$O$_3$S (M+H)$^+$: 378.4, found. 378.2

Preparation 16

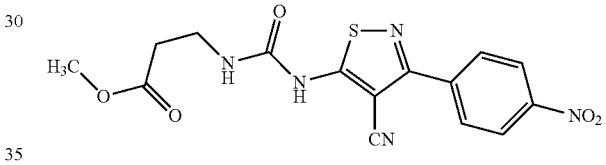

Methyl 3-[({[4-cyano-3-(4-nitrophenyl)isothiazol-5-yl]amino}carbonyl)amino]propanoate Potassium carbonate (35.0 g, 0.25 mol) was added to a solution of 5-amino-3-(4-nitrophenyl)isothiazole-4-carbonitrile (25.0 g, 0.101 mol) in tetrahydrofuran (300 mL) dimethylsulfoxide (60 mL) at ambient temperature. The resulting mixture was stirred at ambient temperature for 15 min. 3-Isocyanato-pripionic acid methyl ester (22.0 g, 0.15 mol) was added at ambient temperature. The mixture was stirred at ambient temperature overnight. The reaction mixture was filtered through celite and the filtrate concentrated in vacuo. The residue was dissolved EtOAc (600 mL) and washed with water and brine then dried (sodium sulfate), filtered, solvent concentrated in vacuo. The crude residue was purified by column chromatography (20% EtOAc in dichloromethane) to give the title compound as a light brown solid (36.0 g, 94%).

Example 52

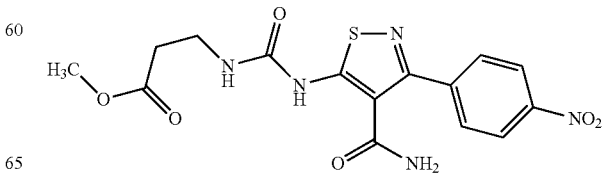

Methyl 3-[({[4-(aminocarbonyl)-3-(4-nitrophenyl) isothiazol-5-yl]amino}carbonyl)amino]propanoate Methyl 3-[({[4-cyano-3-(4-nitrophenyl)isothiazol-5-yl] amino}carbonyl)amino]propanoate (36.0 g) was added portionwise to concentrated sulfuric acid (150.0 mL) at ambient temperature over 20 min. The resulting suspension was heated to 45° C. over 90 min. The reaction mixture was cooled to ambient temperature. The reaction mixture was poured into ice water (600 ml), stirred for 30 min. The solid which formed was collected by filtration and washed with water then dried in vacuo to give the title compound as an off white solid (28.0 g, 75%).

Example 53

5-({[(3-Hydroxypropyl)amino]carbonyl}amino)-3-(4-nitrophenyl)isothiazole-4-carboxamide Sodium borohydride (24.0 g 0.636 mol) was added to a solution of methyl 3-[({[4-(aminocarbonyl)-3-(4-nitrophenyl)isothiazol-5-yl]amino}carbonyl)amino]propanoate (25.0 g, 0.0636 mol) in tetrahydrofuran (1200 mL). The resulting suspension was heated to reflux. Methanol (200 mL) was added drop wise over 1 hr. and the reaction was refluxed for 1 hr. The reaction mixture was cooled to ambient temperature and solvent concentrated in vacuo. The residue taken in EtOAc (600 mL) and washed with water, 2 N HCl and brine then dried (sodium sulfate), filtered, solvent concentrated in vacuo to give the title compound as a yellow solid (18.8 g, 80%).

Example 54

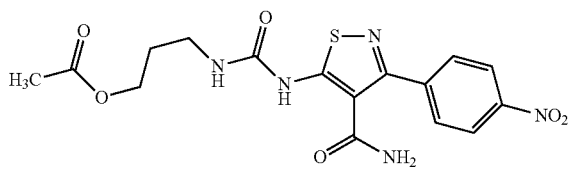 [SMILES: CC(=O)OCCCNC(=O)Nc1snc(-c2ccc([N+](=O)[O-])cc2)c1C(N)=O]

3-[({[4-(Aminocarbonyl)-3-(4-nitrophenyl)isothiazol-5-yl]amino}carbonyl)amino]propyl acetate Acetic anhydride (4.2 g 0.041 mol) was added to a solution of 5-({[(3-hydroxypropyl)amino]carbonyl}amino)-3-(4-nitrophenyl)isothiazole-4-carboxamide (12.0 g, 0.032 mol) in pyridine (120 mL) at ambient temperature over 10 min. The resulting mixture was stirred at ambient temperature for 2 hr. The reaction mixture was concentrated in vacuo. The residue taken in EtOAc (500 mL) and washed with water and brine then dried (sodium sulfate), filtered, solvent concentrated in vacuo to give the title compound as a yellow solid (12.2 g, 92%).

Example 55

3-[({[4-(Aminocarbonyl)-3-(4-aminophenyl)isothiazol-5-yl]amino}carbonyl)amino]propyl acetate 3-[({[4-(aminocarbonyl)isothiazol-3-(4-nitrophenyl)-5-yl]amino}carbonyl)amino]propyl acetate (12.0 g,) and 10% palladium on carbon (3 g) in tetrahydrofuran (400 mL) and dimethylformamide (100 mL) was hydrogenated at 80 psi over 24 hr. in metal bomb. Filter the catalyst on celite and washed with tetrahydrofuran. The filtrate was concentrated in vacuo to give off white solid, which was stirred in ether (100 mL) and filtered gave the title compound as an off white solid (8.5 g, 77%).

Example 56

5-({[(3-Hydroxypropyl)amino]carbonyl}amino)-3-[4-({[(4-methylphenyl)amino]carbonyl}amino)phenyl]isothiazole-4-carboxamide para-Tolyl isocyanate (3.2 g 0.024 mol) was added to a solution of 3-[({[4-(aminocarbonyl)-3-(4-aminophenyl) isothiazol-5-yl]amino}carbonyl)amino]propyl acetate (8.4 g, 0.022 mol), diisopropylethylamine (4.3 g, 0.046 mol) in tetrahydrofuran (250 mL) dimethylsulfoxide (20 mL) at ambient temperature. The resulting mixture was stirred at ambient temperature for 2 hr. The reaction mixture was concentrated in vacuo to give off white solid, which was stirred in ether (150 mL), filtered the solid and washed with ether gave a white solid (10.8 g, 95%). The solid was taken in methanol (100 mL) and tetrahydrofuran (100 ml) mixture, 25% sodium methoxide in methanol (5 mL) was added at ambient temperature. The resulting mixture was stirred at ambient temperature for 2 hr. The reaction mixture was concentrated in vacuo to give off white solid, the solid stirred in water and acidified with 2 N HCl and filtered the solid. Washed with water and dried to give the title compound as an off white solid (8.7 g, 87%).

ESI-MS: Calc. for $C_{22}H_{25}N_6O_4S$ (M+H)$^+$: 469.5, found. 469.1

Example 57

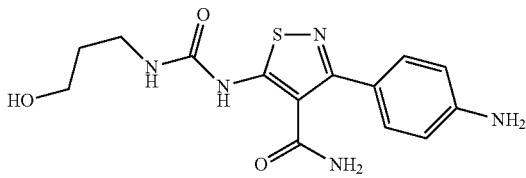

3-(4-Aminophenyl)-5-({[(3-hydroxypropyl)amino]carbonyl}amino)isothiazole-4-carboxamide 3-[({[4-(aminocarbonyl)-3-(4-aminophenyl)isothiazol-5-yl]amino}carbonyl)amino]propyl acetate (10.0 g) and 10% palladium on carbon (3 g) in tetrahydrofuran (400 mL) and dimethylformamide (100 mL) was hydrogenated at 80 psi over 24 hr. in metal bomb. The catalyst was removed by filtration through celite and washed with tetrahydrofuran. The filtrate was concentrated in vacuo to give a yellow solid, which was stirred in ether (100 mL) and collected by filtration to give the title compound as a light yellow solid (8.8 g, 96%).

ESI-MS: Calc. for $C_{14}H_{17}N_5O_3S$ (M+H)$^+$: 336.3, found. 336.2

Example 58

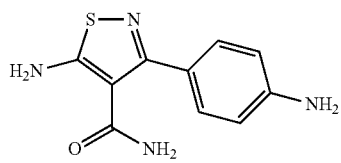 [SMILES: NC(=O)c1c(-c2ccc(N)cc2)nsc1N]

5-Amino-3-(4-aminophenyl)isothiazole-4-carboxamide

A mixture of 5-amino-3-(4-nitrophenyl)isothiazole-4-carboxamide (63 mg, 0.24 mmol), 12 drops saturated aqueous $NH_4Cl$, and catalytic Zn powder in 4 mL MeOH was rapidly stirred at rt. After 1.5 hours additional saturated aqueous $NH_4Cl$ (6 drops) and catalytic Zn powder was added and the reaction heated at 55° C. Then additional solid $NH_4Cl$ and catalytic Zn powder was added to push the reaction to completion. At 4 hours the reaction was filtered using Celite and the solids rinsed with MeOH and EtOAc, the filtrate evaporated and treated to an aqueous workup using EtOAc and saturated aqueous $NaHCO_3$ to give a yellow gummy solid. This material was triturated with 20% EtOAc/hexane to give the title compound as a yellow-beige solid (53 mg, 94%).

$^1$H NMR (Acetone-d6) δ: 7.62 (br. s., 2H), 7.20-7.25 (m, 2H), 6.71-6.77 (m, 2H), 6.29 (br. s., 1H), 5.53 (br. s., 1H), 4.98 (br. s., 2H)

Example 59

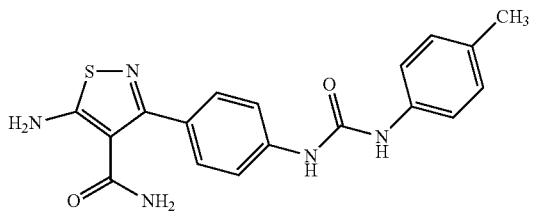 [SMILES: Cc1ccc(NC(=O)Nc2ccc(-c3nsc(N)c3C(N)=O)cc2)cc1]

5-Amino-3-[4-({[(4-methylphenyl)amino]carbonyl}amino)phenyl]isothiazole-4-carboxamide A mixture of 5-amino-3-(4-aminophenyl)isothiazole-4-carboxamide (25 mg, 0.11 mmol), N,N-diisopropylethylamine (0.047 mL, 0.27 mmol), and para-tolyl isocyanate (0.016 mL, 0.13 mmol) in 0.9 mL DCM was reacted at room temperature. After 1 hour an additional 0.006 mL para-tolyl isocyanate was added, and then 0.004 mL at 3.5 hrs. At 21 hours the reaction was quenched with 1 mL MeOH, stirred 10 min at rt, and then evaporated. The residue was triturated with EtOAc which afforded the title compound as a pale yellow solid (28 mg, 72%).

$^1$H NMR (Acetone-d6) δ: 8.28 (s, 1H), 8.08 (s, 1H), 7.61-7.68 (m, 4H), 7.40-7.48 (m, 4H), 7.10 (d, J=8.2 Hz, 2H), 6.33 (br. s, 1H), 5.49 (br. s, 1H), 2.27 (s, 3H)

Example 60

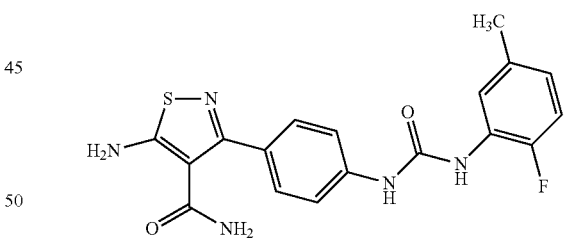

5-Amino-3-[4-({[(2-fluoro-5-methylphenyl)amino]carbonyl}amino)phenyl]isothiazole-4-carboxamide A mixture of 5-amino-3-(4-aminophenyl)isothiazole-4-carboxamide (18 mg, 0.079 mmol), N,N-diisopropylethylamine (0.034 mL, 0.20 mmol), and 2-fluoro-5-methylphenyl isocyanate (0.014 mL, 0.11 mmol) in 1.0 mL dioxane was reacted at room temperature for 2.5 hours. The reaction was quenched with 0.5 mL MeOH, stirred 5 min at room temperature, and then evaporated. The residue was recrystallized from EtOAc/CHCl$_3$ to give the title compound as a pale yellow solid (27 mg, 88%).

¹H NMR (Acetone-d6) δ: 8.70 (s, 1H), 8.15 (d, J=7.6 Hz, 1H), 8.01 (br. s., 1H), 7.67 (d, J=8.5 Hz, 2H), 7.63 (br. s., 2H), 7.48 (d, J=8.5 Hz, 2H), 7.02 (dd, J=11.4, 8.2 Hz, 1H), 6.78-6.86 (m, 1H), 2.32 (s, 3H)

Preparation 17

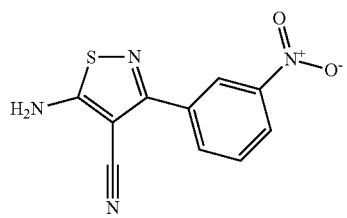 [SMILES: N#Cc1c(-c2cccc([N+](=O)[O-])c2)nsc1N]

5-Amino-3-(3-nitrophenyl)isothiazole-4-carbonitrile

3-Nitrobenzoyl chloride was converted to the title compound using a route siimilar to that described in preparations 1-5.

Example 61

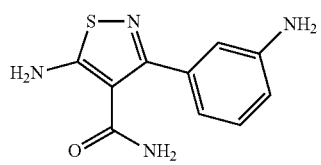 [SMILES: NC(=O)c1c(-c2cccc(N)c2)nsc1N]

5-Amino-3-(3-nitrophenyl)isothiazole-4-carboxamide

A mixture of 5-amino-3-(3-nitrophenyl)isothiazole-4-carbonitrile (500 mg, 2.03 mmol) in 5 mL conc. $H_2SO_4$ was heated at 65° C. After 4 hours the mixture was slowly added to 75 mL ice water (including an additional reaction run on 0.50 mmol scale in 1.5 mL conc. $H_2SO_4$). The mixture was stirred for 10 min, and then the precipitate filtered and rinsed with water and 10% EtOAc/hexane to give the title compound as a light beige solid (572 mg, 86% combined yield).
¹H NMR (DSMO-d6) δ: 8.34 (t, J=1.9 Hz, 1H), 8.27 (ddd, J=8.2, 2.3, 0.9 Hz, 1H), 7.97 (dt, J=8.1, 1.2 Hz, 1H), 7.68-7.74 (m, 1H), 7.37 (s, 2H)

Example 62

5-Amino-3-(3-aminophenyl)isothiazole-4-carboxamide

A mixture of 5-amino-3-(3-nitrophenyl)isothiazole-4-carboxamide (150 mg, 0.57 mmol), 0.5 mL saturated aqueous $NH_4Cl$, and catalytic Zn powder in 6 mL MeOH was rapidly stirred at rt. After 1.5 hours additional saturated aqueous $NH_4Cl$ and catalytic Zn powder was added several times to push the reaction to completion. At 20 hours the reaction was heated at 55° C. for 6 hours, then stirred overnight at rt. The reaction was filtered using Celite and the solids rinsed with MeOH, the filtrate evaporated and treated to an aqueous workup using EtOAc and aqueous $Na_2CO_3$ to give a pale yellow solid. The solid was triturated with EtOAc/hexane to give 94 mg of faint yellow solid. Then the filtrate lot and the 94 mg of solid were separately chromatographed eluting with hexane/acetone and combined to give the title compound as an off-white solid (96 mg, 72%).
¹H NMR (Acetone-d6) δ: 7.72 (br. s., 2H), 7.13-7.20 (m, 1H), 6.75-6.80 (m, 2H), 6.68 (d, J=7.3 Hz, 1H), 6.28 (br. s., 1H), 5.46 (br. s., 1H), 4.87 (br. s., 2H)

Example 63

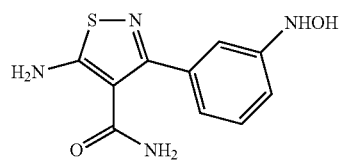

5-Amino-3-[3-(hydroxyamino)phenyl]isothiazole-4-carboxamide

A mixture of 5-amino-3-(3-nitrophenyl)isothiazole-4-carboxamide (50 mg, 0.19 mmol) and platinum oxide (20 mg, 0.088 mmol) in 5 mL MeOH was hydrogenated under 60 PSI hydrogen. After 5 hours an additional catalytic amount of platinum oxide was added and the reaction continued for 67 hours. The reaction mixture was filtered using Celite and the filter bed rinsed with 40% MeOH/CHCl₃. The filtrate was evaporated to give 32 mg of yellow solid. Then 22 mg of this material was chromatographed eluting with CHCl₃/MeOH to give the title compound as a pale yellow solid (10.2 mg).
¹H NMR (DSMO-d6) δ: 8.42 (s, 1H), 8.39 (d, J=2.3 Hz, 1H), 7.67 (s, 2H), 7.21-7.28 (m, 1H), 7.15 (br. s., 1H), 6.93 (s, 1H), 6.90 (d, J=7.9 Hz, 1H), 6.83 (d, J=7.3 Hz, 1H), 5.64 (br. s., 1H)

Example 64

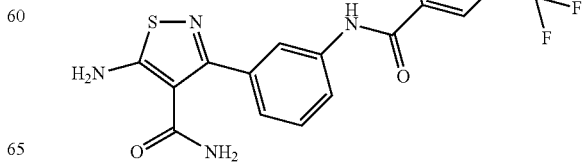

5-Amino-3-(3-{[3-(trifluoromethyl)benzoyl]amino}phenyl)isothiazole-4-carboxamide To a mixture of 5-amino-3-(3-aminophenyl)isothiazole-4-carboxamide (13 mg, 0.056 mmol) and N,N-diisopropylethylamine (0.029 mL, 0.17 mmol) in 1.0 mL CH$_2$Cl$_2$ at room temperature was added 3-(trifluoromethyl)benzoyl chloride (0.008 mL, 0.056 mmol) and the reaction stirred at room temperature. After 1 hour, additional 3-(trifluoromethyl)benzoyl chloride (0.0015 mL) was added, then again at 2 hours (0.002 mL) and 3 hours (0.0015 mL). After 4 hours the reaction was evaporated, and then treated to an aqueous Na$_2$CO$_3$ and EtOAc workup to yield a light yellow solid. The solid was precipitated from EtOAc/hexane to give the title compound as an off-white solid (16 mg, 68%).

$^1$H NMR (Acetone-d6) δ: 9.93 (br. s., 1H), 8.29-8.36 (m, 2H), 8.01-8.06 (m, 1H), 7.98-8.00 (m, 1H), 7.94 (d, J=7.9 Hz, 1H), 7.76-7.83 (m, 1H), 7.68 (br. s., 2H), 7.50 (t, J=7.8 Hz, 1H), 7.29-7.34 (m, 1H)

Example 65

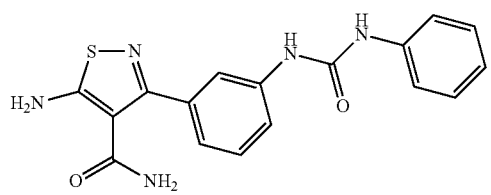 [SMILES: NC(=O)c1c(-c2cccc(NC(=O)Nc3ccccc3)c2)nsc1N]

5-Amino-3-{3-[(anilinocarbonyl)amino]phenyl}isothiazole-4-carboxamide

A mixture of 5-amino-3-(3-aminophenyl)isothiazole-4-carboxamide (21 mg, 0.090 mmol), N,N-diisopropylethylamine (0.039 mL, 0.23 mmol), and phenyl isocyanate (0.014 mL, 0.13 mmol) in 1.0 mL dioxane was reacted at rt for 1 hour. The precipitant was filtered and rinsed with 30% EtOAc/hexane to give the title compound as a white solid (31 mg, 96%).

$^1$H NMR (DSMO-d6) δ: 8.81 (s, 1H), 8.68 (s, 1H), 7.62 (s, 1H), 7.58 (s, 2H), 7.52 (d, J=8.2 Hz, 1H), 7.45 (d, J=7.6 Hz, 2H), 7.35 (t, J=7.9 Hz, 1H), 7.28 (t, J=7.8 Hz, 2H), 7.17 (br. s., 1H), 7.08 (d, J=7.6 Hz, 1H), 6.93-7.01 (m, 1H), 5.88 (br. s., 1H)

Preparation 18

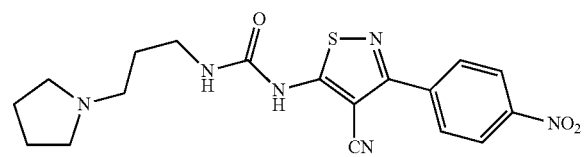 [SMILES: N#Cc1c(-c2ccc([N+](=O)[O-])cc2)nsc1NC(=O)NCCCN1CCCC1]

1-[4-Cyano-3-(4-nitrophenyl)isothiazol-5-yl]-3-(3-pyrrolidin-1-ylpropyl)urea

Carbonyldiimidazole (24.7 g, 0.152 mol) was added to a solution of 3-pyrrolidin-1-yl-propylamine (19.5 g, 0.152 mol) in dimethylformamide (200 mL) at 0° C. The resulting mixture was stirred at ambient temperature for 1 hr.

Potassium carbonate (35.0 g, 0.25 mol) was added to a solution of 5-amino-3-(4-nitrophenyl)isothiazole-4-carbonitrile (25.0 g, 0.101 mol) in dimethylformamide (200 mL) at ambient temperature. The resulting mixture was stirred at ambient temperature for 15 min. The above mixture was added at ambient temperature. The mixture was stirred at ambient temperature for over night. The reaction mixture was concentrated in vacuo. The residue was dissolved ethyl acetate (600 mL) and filtered through celite and washed with ethyl acetate. The filtrate was washed with water and brine then dried (sodium sulfate), filtered, and concentrated in vacuo. The crude compound purified by column chromatography (10% methanol/dichloromethane) to give the title compound as a yellow solid (34.0 g, 85%).

Example 66

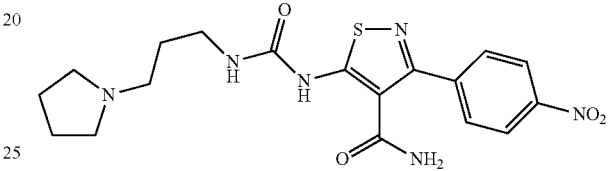

3-(4-Nitrophenyl)-5-({[(3-pyrrolidin-1-ylpropyl)amino]carbonyl}amino)isothiazole-4-carboxamide 1-[4-cyano-3-(4-nitrophenyl)isothiazol-5-yl]-3-(3-pyrrolidin-1-ylpropyl)urea (36.0 g) was added portion wise to concentrated sulfuric acid (180.0 mL) at ambient temperature over 20 min. The resulting suspension was heated to 45° C. over 90 min. The reaction mixture was cooled to ambient temperature. The reaction mixture was poured into ice water (2000 ml), stirred for 30 min. The resulting mixture was made basic using ammonium hydroxide, filtered the solid and washed with water then dried in vacuo to give the title compound as off white solid (34.0 g, 90%).

Example 67

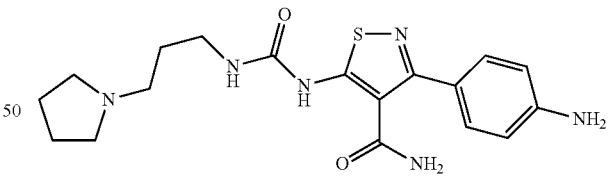

3-(4-Aminophenyl)-5-({[(3-pyrrolidin-1-ylpropyl)amino]carbonyl}amino)isothiazole-4-carboxamide 3-(4-nitrophenyl)-5-({[(3-pyrrolidin-1-ylpropyl)amino]carbonyl}amino)isothiazole-4-carboxamide (16.0 g,) and 10% palladium on carbon (6 g) in tetrahydrofuran (1500 mL) was hydrogenated at 80 psi over 24 hr in metal bomb. Filter the catalyst on celite and washed with tetrahydrofuran. The filtrate was concentrated in vacuo to give off white solid, which was stirred in ether (200 mL) and filtered to give the title compound as a white solid (13.8 g, 93%).

ESI-MS: Calc. for $C_{18}H_{25}N_6O_2S$ (M+H)$^+$: 389, found. 389.1

Example 68

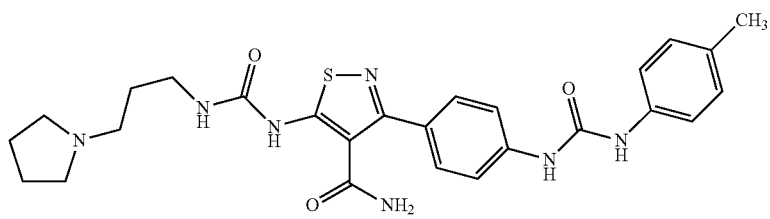 [SMILES: Cc1ccc(NC(=O)Nc2ccc(-c3nsc(NC(=O)NCCCN4CCCC4)c3C(N)=O)cc2)cc1]

3-[4-({[(4-Methylphenyl)amino]carbonyl}amino)
phenyl]-5-({[(3-pyrrolidin-1-ylpropyl)amino]
carbonyl}amino)isothiazole-4-carboxamide Para-Tolyl isocyanate (4.5 g 0.0339 mol) was added to a solution of 3-(4-aminophenyl)-5-({[(3-pyrrolidin-1-ylpropyl)amino]carbonyl}amino)isothiazole-4-carboxamide (12.0 g, 0.0308 mol), diisopropylethylamine (6.0 g, 0.046 mol) in mixture of tetrahydrofuran (300 mL) and dimethylformamide (50 ml) at ambient temperature over 20 min. The resulting mixture was stirred at ambient temperature for 2 hr. The reaction mixture was concentrated in vacuo to give off white solid, which was stirred in 20% tetrahydrofuran and ethyl acetate (200 mL) mixture, filtered the solid and washed with ethyl acetate the title compound as a white solid (15.8 g, 98%).

ESI-MS: Calc. for $C_{26}H_{32}N_{17}O_3S$ (M+H)$^+$: 522, found. 522.2

Preparation 19

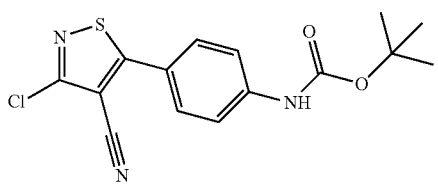 [SMILES: CC(C)(C)OC(=O)Nc1ccc(-c2snc(Cl)c2C#N)cc1]

tert-Butyl [4-(3-chloro-4-cyanoisothiazol-5-yl)phenyl]carbamate

A mixture of 3,5-dichloroisothiazole-4-carbonitrile (5.37 g, 30 mmol), 4-(tert-butoxycarbonylamino)phenylboronic acid (14.22 g, 60 mmol), potassium fluoride (6.11 g, 105 mmol), 18-crown-6 (3.96 g, 15 mmol), and palladium acetate (337 mg, 1.5 mmol) in toluene (250 ml) was heated at reflux for 6 hours. The reaction was cooled to room temperature and the mixture was diluted with water and EtOAc. Layers were separated and the aqueous layer was extracted with EtOAc (3×). The combined organic extracts were washed with brine and dried with MgSO$_4$, filtered, and concentrated. The crude product was purified by flash silica gel column eluted with 5-15% EtOAc in hexanes to obtain the title compound as a white crystalline solid (8.55 g, 85%).

Preparation 20

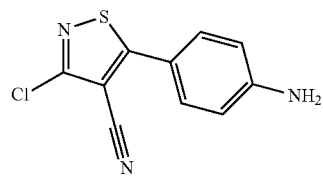 [SMILES: N#Cc1c(Cl)nsc1-c1ccc(N)cc1]

3-(4-Amino-phenyl)-5-chloro-isothiazole-4-carbonitrile

A solution of tert-butyl [4-(3-chloro-4-cyanoisothiazol-5-yl)phenyl]carbamate (4.76 g, 13.38 mmol) in CH$_2$Cl$_2$ (100 ml) was treated with 10 mL of trifluoroacetic acid. The reaction mixture was stirred at room temperature overnight. Solvent was removed in vacuo. The residue was diluted with water and CH$_2$Cl$_2$ (100 ml). Layers were separated and the aqueous layer was extracted with CH$_2$Cl$_2$ (2×). The combined organic extracts were washed with brine and dried with MgSO$_4$, filtered, and concentrated. Product was rinsed with Et$_2$O/hexanes and collected by filtration to give the title compound as a bright yellow solid (3.15 g, 94%).

Preparation 21

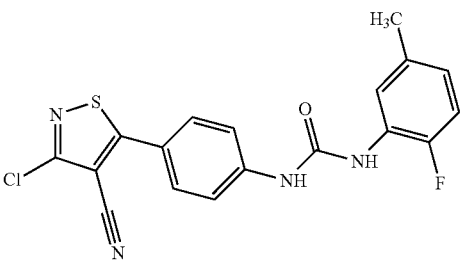 [SMILES: Cc1ccc(F)c(NC(=O)Nc2ccc(-c3snc(Cl)c3C#N)cc2)c1]

1-[4-(5-Chloro-4-cyano-isothiazol-3-yl)-phenyl]-3-(2-fluoro-5-methyl-phenyl)-urea A solution of 3-(4-amino-phenyl)-5-chloro-isothiazole-4-carbonitrile (4.565 g, 19.4 mmol) and 2-fluoro-5-methylphenyl isocyanate (5.85 g, 38.7 mmol) in 100 mL of dry THF was heated to reflux overnight. TLC indicated presence of considerable amount of starting material. Additional 2 g of 2-fluoro-5-methylphenyl isocyanate was added and the reaction was continued for another 24 h. The reaction was cooled to room temperature. THF was removed in vacuo and the resulting solid was stirred in 200 mL of Et₂O for 1 h. Product was collected by filtration and washed with Et₂O/hexanes to afford the title compound as a light yellow solid (6.78 g, 90%).

Preparation 22

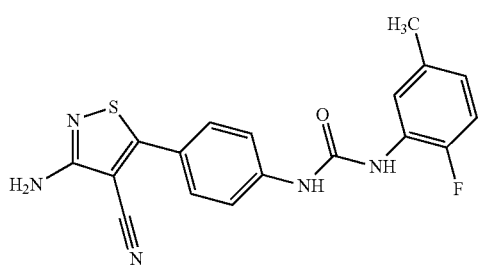 [SMILES: Cc1ccc(F)c(NC(=O)Nc2ccc(-c3snc(N)c3C#N)cc2)c1]

1-(4-(3-Amino-4-cyanoisothiazol-5-yl)phenyl)-3-(2-fluoro-5-methylphenyl)urea

A suspension of 1-(4-{4-cyano-3-[(2,4-dimethoxybenzyl)amino]isothiazol-5-yl}phenyl)-3-(2-fluoro-5-methylphenyl)urea (593 mg, 1.15 mmol) in 50 mL of CH₂Cl₂ was treated with 1.5 mL of trifluoroacetic acid. Solid was dissolved and the reaction turned to yellow and then red in color. TLC indicated the completion of the reaction in <30 min. Saturated Na₂CO₃ solution was added and the mixture was stirred for 30 min. Layers were separated and the aqueous layer was extracted with CH₂Cl₂ (3×). The combined organic extracts were washed with brine and dried with MgSO₄, filtered, and concentrated. The crude product was redissolved in 100 mL of EtOAc. Insoluble impurity was filtered through celite and washed with EtOAc. Filtrate was concentrated in vacuo to afford the title compound as a cream solid (398 mg, 94%).

Example 69

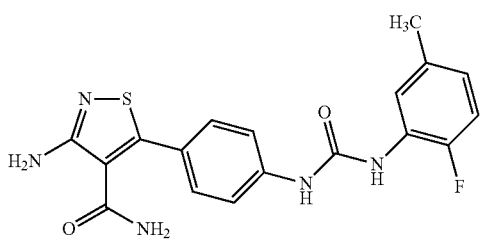 [SMILES: Cc1ccc(F)c(NC(=O)Nc2ccc(-c3snc(N)c3C(N)=O)cc2)c1]

3-Amino-5-[4-({[(2-fluoro-5-methylphenyl)amino]carbonyl}amino)phenyl]isothiazole-4-carboxamide To a mixture of 1-[4-(3-amino-4-cyanoisothiazol-5-yl)phenyl]-3-(2-fluoro-5-methylphenyl)urea (10.2 mg, 0.028 mmol) in 0.8 mL EtOH at rt was added 15 drops 1.0M aqueous NaOH, 7 drops 30% hydrogen peroxide and the reaction stirred at rt for 30 min, then heated at 60° C. After 2.5 hours an aqueous HCl (dilute) and EtOAc workup was done to give a light yellow solid. To this material was added an impure lot from another reaction, and the combined lots triturated with EtOAc to give the title compound as a pale yellow solid (26 mg, 93% combined yield).

¹H NMR (DSMO-d6) δ: 9.32 (s, 1H), 8.55 (d, J=2.6 Hz, 1H), 7.98 (dd, J=7.9, 1.8 Hz, 1H), 7.54-7.59 (m, 2H), 7.49 (br. s., 1H), 7.39-7.44 (m, 2H), 7.06-7.15 (m, 2H), 6.78-6.85 (m, 1H), 6.21 (s, 2H), 2.28 (s, 3H)

Preparation 23

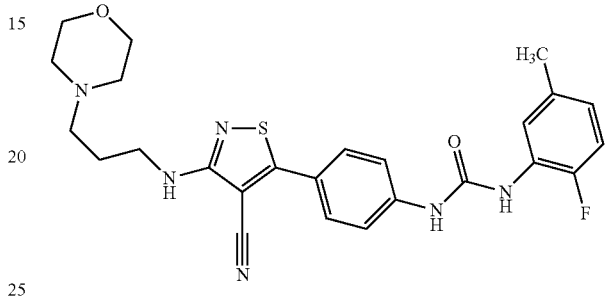

1-(4-{4-Cyano-3-[(3-morpholin-4-ylpropyl)amino]isothiazol-5-yl}phenyl)-3-(2-fluoro-5-methylphenyl)urea A mixture of 1-[4-(3-chloro-4-cyanoisothiazol-5-yl)phenyl]-3-(2-fluoro-5-methylphenyl)urea (50 mg, 0.13 mmol) and 0.2 mL 3-morpholinopropylamine was heated at 70° C. for 18 hours. Then an aqueous Na₂CO₃/brine mixture and EtOAc workup was done, and the resulting material chromatographed eluting with CHCl₃/MeOH. The resulting solid was then triturated with a 1:1/CHCl₃/hexane mixture which gave the title compound as a pale yellow solid (10 mg, 16%).

¹H NMR (Acetone-d6) δ: 8.88 (s, 1H), 8.13 (dd, J=7.8, 1.9 Hz, 1H), 8.08 (d, J=2.6 Hz, 1H), 7.73-7.80 (m, 4H), 7.10 (t, J=4.7 Hz, 1H), 7.03 (dd, J=11.4, 8.5 Hz, 1H), 6.81-6.87 (m, 1H), 3.69-3.74 (m, 4H), 3.49-3.57 (m, 2H), 2.50-2.55 (m, 2H), 2.46 (br. s., 4H), 2.32 (s, 3H), 1.87 (quin, J=6.2 Hz, 2H)

Example 70

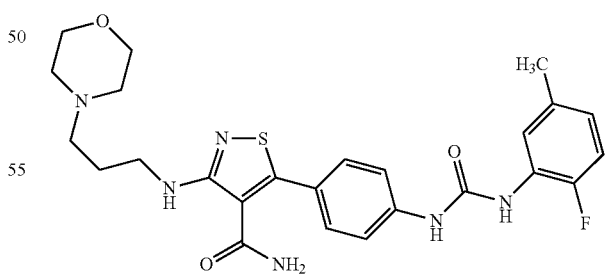

5-[4-({[(2-Fluoro-5-methylphenyl)amino]carbonyl}amino)phenyl]-3-[(3-morpholin-4-ylpropyl)amino]isothiazole-4-carboxamide To a solution of 1-(4-{4-cyano-3-[(3-morpholin-4-ylpropyl)amino]isothiazol-5-yl}phenyl)-3-(2-fluoro-5-methylphenyl)urea (5 mg, 0.011 mmol) in 0.8 mL DMSO at rt was added catalytic $K_2CO_3$, 1 drop 30% hydrogen peroxide and the reaction stirred at rt for 30 min. The reaction was added into a solution of dilute brine and the precipitant filtered and rinsed with water, then 20% EtOAc/hexane. The product was washed from the filter paper using 15% MeOH/$CHCl_3$ and then evaporated to give the title compound as a white solid (5 mg, 85%).

$^1$H NMR (Acetone-d6) δ: 8.80 (s, 1H), 8.13 (dd, J=7.8, 2.2 Hz, 1H), 8.05 (d, J=2.9 Hz, 1H), 7.70-7.75 (m, 2H), 7.44-7.49 (m, 2H), 7.39 (t, J=5.4 Hz, 1H), 7.02 (dd, J=11.4, 8.2 Hz, 1H), 6.80-6.86 (m, 1H), 6.68 (br. s., 1H), 6.10 (br. s., 1H), 3.63-3.67 (m, 4H), 3.46-3.53 (m, 2H), 2.38-2.47 (m, 6H), 2.32 (s, 3H), 1.82 (quin, J=6.7 Hz, 2H)

Preparation 24

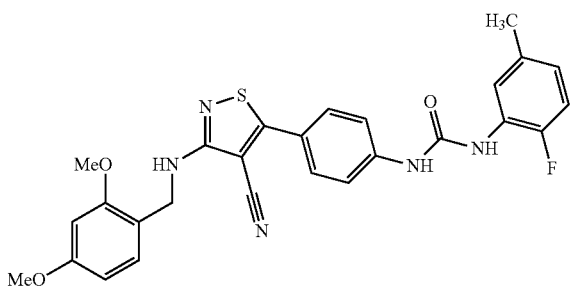 [SMILES: COc1ccc(CNc2nsc(-c3ccc(NC(=O)Nc4cc(C)ccc4F)cc3)c2C#N)c(OC)c1]

1-(4-{4-Cyano-3-[(2,4-dimethoxybenzyl)amino] isothiazol-5-yl}phenyl)-3-(2-fluoro-5-methylphenyl) urea A suspension of 1-[4-(5-Chloro-4-cyano-isothiazol-3-yl)-phenyl]-3-(2-fluoro-5-methyl-phenyl)-urea (see Preparation 21 above; 4.3 g, 11.1 mmol) in 15 mL of 2,4-dimethoxybenzylamine was heated to 73° C. for 24 h. The reaction became clear after ~3 h. The reaction was cooled to room temperature. The residue was diluted with 300 mL of DCM and was washed with 10% HCl solution two times, saturated $Na_2S_2O_5$ two times followed by brine. The organic solution was dried with $MgSO_4$, filtered, and concentrated. The crude product was purified by flash silica gel column eluted with 2-5% MTBE in DCM/hexanes (2:1) to obtain the title compound as a light yellow solid (1.19 g, 21%).

Example 71

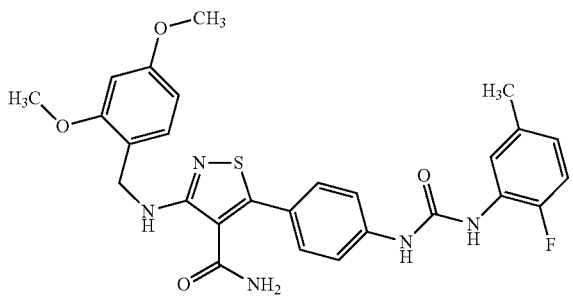 [SMILES: COc1ccc(CNc2nsc(-c3ccc(NC(=O)Nc4cc(C)ccc4F)cc3)c2C(N)=O)c(OC)c1]

3-[(2,4-Dimethoxybenzyl)amino]-5-[4-({[(2-fluoro-5-methylphenyl)amino]carbonyl}amino)phenyl] isothiazole-4-carboxamide To a solution of 1-(4-{4-cyano-3-[(2,4-dimethoxybenzyl) amino]isothiazol-5-yl}phenyl)-3-(2-fluoro-5-methylphenyl) urea (26 mg, 0.050 mmol) in 0.8 mL DMSO at rt was added catalytic $K_2CO_3$, 5 drops 30% hydrogen peroxide and the reaction stirred at rt for 30 min. The reaction was added into a solution of dilute brine and the precipitant filtered and rinsed with water, then 30% EtOAc/hexane to give the title compound as a pale yellow solid (24 mg, 91%).

$^1$H NMR (DSMO-d6) δ: 9.31 (s, 1H), 8.55 (d, J=2.3 Hz, 1H), 7.98 (dd, J=7.8, 1.6 Hz, 1H), 7.50-7.60 (m, 3H), 7.41 (d, J=8.5 Hz, 2H), 7.17 (d, J=8.5 Hz, 1H), 7.11 (dd, J=11.4, 8.2 Hz, 1H), 6.95 (br. s., 1H), 6.88 (t, J=5.9 Hz, 1H), 6.78-6.85 (m, 1H), 6.57 (d, J=2.3 Hz, 1H), 6.47 (dd, J=8.4, 2.2 Hz, 1H), 4.39 (d, J=5.9 Hz, 2H), 3.81 (s, 3H), 3.74 (s, 3H), 2.27 (s, 3H)

Biological data for the compounds of the present invention was generated by use of the following assays.

VEGFR2 Kinase Assay

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of $2.5NH_2SO_4$ to each well and read using a microplate ELISA reader set at 492 nm. $IC_{50}$ values for compound inhibition were calculated directly from graphs of optical density (arbitrary units) versus compound concentration following subtraction of blank values.

VEGFR2 Cellular Assay

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by $VEGF_{165}$ stimulation (10 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of $2.5NH_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Cellular Assay

Automated FLIPR (Fluorometric Imaging Plate Reader) technology was used to screen for inhibitors of PDGF-induced increases in intracellular calcium levels in fluorescent dye loaded endothelial cells. NHDF-Ad (Normal Human Dermal Fibroblasts, Adult; Lonza) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by PDGF-BB stimulation (30 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF-BB stimulated responses in the absence of inhibitor.

The biological results for the various compounds are shown in Tables 1 and 2 below.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered orally, subcutaneously, intravenously, intrathecally or some suitable combination(s) thereof.

In addition to the common dosage forms set out above, the compounds of this invention may also be administered by controlled release means and/or delivery devices such as those described in U.S. Pat. Nos. 3,845,770; 3,916,899; 3,536,809; 3,598,123; 3,630,200; 4,008,719; and 5,366,738 the disclosures of which are incorporated herein by reference.

For use where a composition for intravenous administration is employed, a suitable daily dosage range for anti-inflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day. For the treatment of diseases of the eye, ophthalmic preparations for ocular administration comprising 0.001-1% by weight solutions or suspensions of the compounds of this invention in an acceptable ophthalmic formulation may be used.

Preferably, the pharmaceutical preparation is in a unit dosage form. In such form, the preparation is subdivided into suitably sized unit doses containing appropriate quantities of the active component, e.g., an effective amount to achieve the desired purpose.

The magnitude of prophylactic or therapeutic dose of a compound of this invention will, of course, vary with the nature of the severity of the condition to be treated and with the particular compound and its route of administration. It will also vary according to the age, weight and response of the individual patient. It is understood that a specific daily dosage amount can simultaneously be both a therapeutically effective amount, e.g., for treatment to slow progression of an existing condition, and a prophylactically effective amount, e.g., for prevention of condition.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

In one aspect, the present invention provides a kit comprising a therapeutically effective amount of at least one compound of the present invention, or a pharmaceutically acceptable salt of said compound and a pharmaceutically acceptable carrier, vehicle or diluents, and directions for the use of said kit.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

TABLE 1

| Example | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 1 | 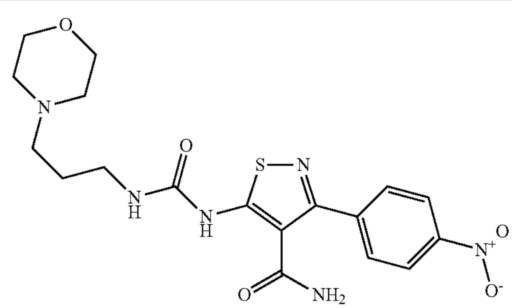 | 5-({[{3-morpholin-4-ylpropyl)amino]carbonyl}amino)-3-(4-nitrophenyl)isothiazole-4-carboxamide | >10000 | >10000 | >10000 |
| Example 2 | 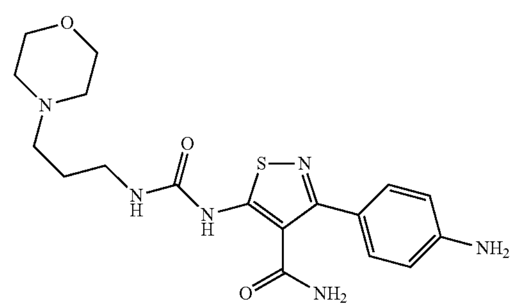 [SMILES: NC(=O)c1c(-c2ccc(N)cc2)nsc1NC(=O)NCCCN1CCOCC1] | 3-(4-aminophenyl)-5-({[(3-morpholin-4-ylpropyl)amino]carbonyl}amino)isothiazole-4-carboxamide | 3280 | NT | >10000 |

TABLE 1-continued

| Example | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 3 | 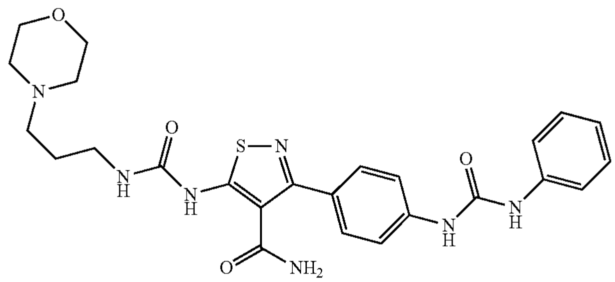 [SMILES: NC(=O)c1c(-c2ccc(NC(=O)Nc3ccccc3)cc2)nsc1NC(=O)NCCCN1CCOCC1] | 3-{4-[(aminocarbonyl)amino]phenyl}-5-({[(3-morpholin-4-ylpropyl)amino]carbonyl}amino)isothiazole-4-carboxamide | 8 | 9 | 21 |
| Example 4 | 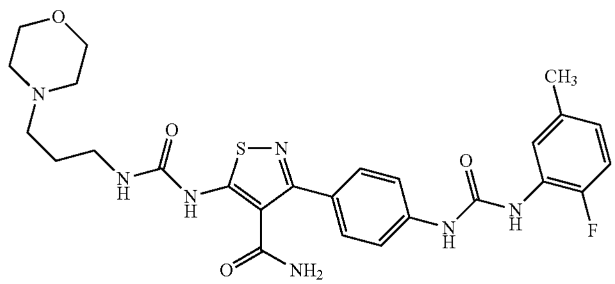 [SMILES: Cc1ccc(F)c(NC(=O)Nc2ccc(-c3nsc(NC(=O)NCCCN4CCOCC4)c3C(N)=O)cc2)c1] | 3-[4-({[(2-fluoro-5-methylphenyl)amino]carbonyl}amino)phenyl]-5-({[(3-morpholin-4-ylpropyl)amino]carbonyl}amino)isothiazole-4-carboxamide | 14 | 11 | 47 |
| Example 5 | 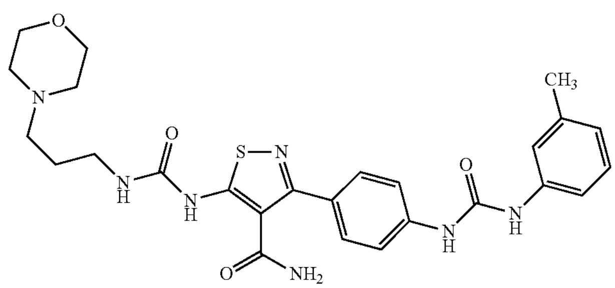 [SMILES: Cc1cccc(NC(=O)Nc2ccc(-c3nsc(NC(=O)NCCCN4CCOCC4)c3C(N)=O)cc2)c1] | 3-[4-({[(3-methylphenyl)amino]carbonyl}amino)phenyl]-5-({[(3-morpholin-4-ylpropyl)amino]carbonyl}amino)isothiazole-4-carboxamide | 3 | 3 | 10 |
| Example 6 | 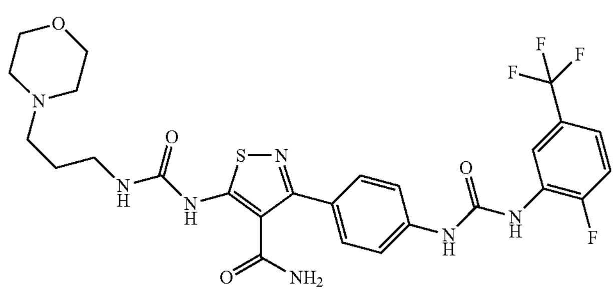 [SMILES: NC(=O)c1c(-c2ccc(NC(=O)Nc3cc(C(F)(F)F)ccc3F)cc2)nsc1NC(=O)NCCCN1CCOCC1] | 3-{4-[3-(2-Fluoro-5-trifluoromethyl-phenyl)-ureido]-2-methyl-phenyl}-5-[3-(3-morpholin-4-yl-propyl)-ureido]-isothiazole-4-carboxylic acid amide | 6 | 13 | 24 |
| Example 7 | 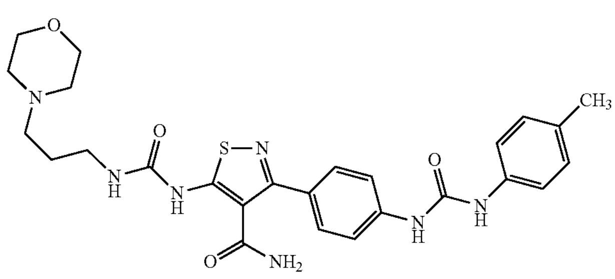 [SMILES: Cc1ccc(NC(=O)Nc2ccc(-c3nsc(NC(=O)NCCCN4CCOCC4)c3C(N)=O)cc2)cc1] | 3-[4-({[(4-methylphenyl)amino]carbonyl}amino)phenyl]-5-({[(3-morpholin-4-ylpropyl)amino]carbonyl}amino)isothiazole-4-carboxamide | 8 | 7 | 12 |

TABLE 1-continued

| Example | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|
| Example 8 | 5-({[(3-methoxypropyl)amino]carbonyl}amino)-3-(4-nitrophenyl)isothiazole-4-carboxamide | NT | NT | NT |
| Example 9 | 3-(4-aminophenyl)-5-({[(3-methoxypropyl)amino]carbonyl}amino)isothiazole-4-carboxamide | 4520 | >1000 | >10000 |
| Example 10 | 3-[4-({[(2-fluoro-5-methylphenyl)amino]carbonyl}amino)phenyl]-5-({[(3-methoxypropyl)amino]carbonyl}amino)isothiazole-4-carboxamide | 39 | NT | NT |
| Example 11 | 5-({[(3-morpholin-4-ylpropyl)amino]carbonyl}amino)-3-(4-{[3-(trifluoromethyl)benzoyl]amino}phenyl)isothiazole-4-carboxamide | 4520 | >1000 | >1000 |
| Example 12 | 3-[3-(4-Carbamoyl-3-{4-[3-(2-fluoro-5-trifluoromethyl-phenyl)-ureido]-2-methyl-phenyl}-isothiazol-5-yl)-ureido]-propionic acid | NT | NT | NT |

TABLE 1-continued

| Example | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 13 | 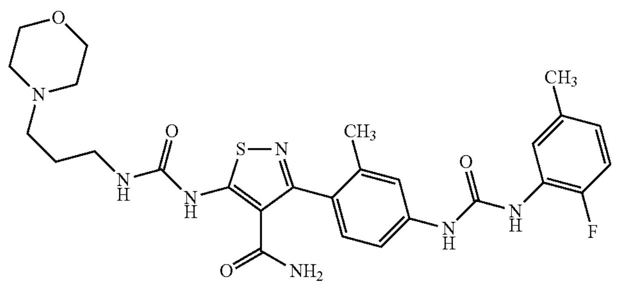 [SMILES: Cc1ccc(F)c(NC(=O)Nc2ccc(-c3nsc(NC(=O)NCCCN4CCOCC4)c3C(N)=O)c(C)c2)c1] | 3-{4-[3-(2-Fluoro-5-methyl-phenyl)-ureido]-2-methyl-phenyl}-5-[3-(3-morpholin-4-yl-propyl)-ureido]-isothiazole-4-carboxylic acid amide | 27 | NT | NT |
| Example 14 | 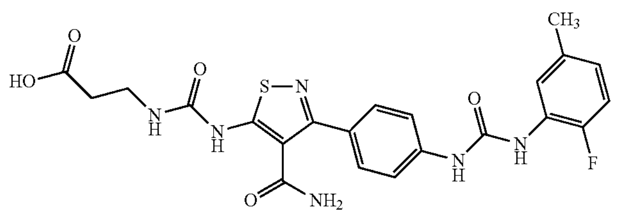 [SMILES: Cc1ccc(F)c(NC(=O)Nc2ccc(-c3nsc(NC(=O)NCCC(=O)O)c3C(N)=O)cc2)c1] | 3-[3-(4-Carbamoyl-3-{4-[3-(2-fluoro-5-methyl-phenyl)-ureido]-phenyl}-isothiazol-5-yl)-ureido]-propionic acid | NT | NT | NT |
| Example 15 | 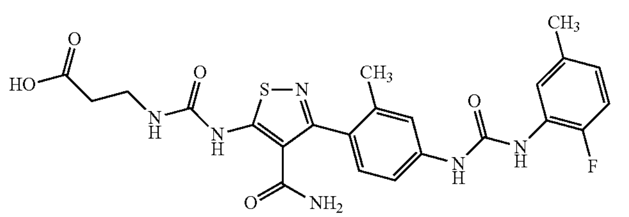 [SMILES: Cc1ccc(F)c(NC(=O)Nc2ccc(-c3nsc(NC(=O)NCCC(=O)O)c3C(N)=O)c(C)c2)c1] | 3-[3-(4-Carbamoyl-3-{4-[3-(2-fluoro-5-methyl-phenyl)-ureido]-2-methyl-phenyl}-isothiazol-5-yl)-ureido]-propionic acid | NT | NT | NT |
| Example 16 | 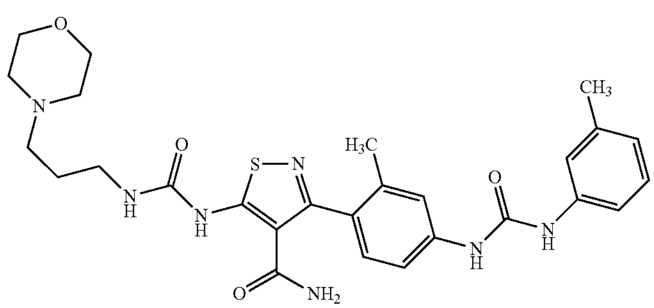 [SMILES: Cc1cccc(NC(=O)Nc2ccc(-c3nsc(NC(=O)NCCCN4CCOCC4)c3C(N)=O)c(C)c2)c1] | 3-[2-Methyl-4-(3-m-tolyl-ureido)-phenyl]-5-[3-(3-morpholin-4-yl-propyl)-ureido]-isothiazole-4-carboxylic acid amide | NT | NT | NT |
| Example 17 | 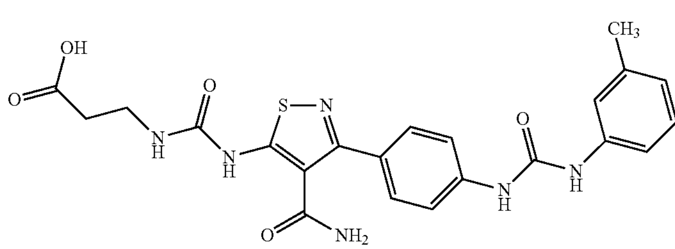 [SMILES: Cc1cccc(NC(=O)Nc2ccc(-c3nsc(NC(=O)NCCC(=O)O)c3C(N)=O)cc2)c1] | 3-(3-{4-Carbamoyl-3-[2-methyl-4-(3-m-tolyl-ureido)-phenyl]-isothiazol-5-yl}-ureido)-propionic acid | NT | NT | NT |

TABLE 1-continued

| Example | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 18 | 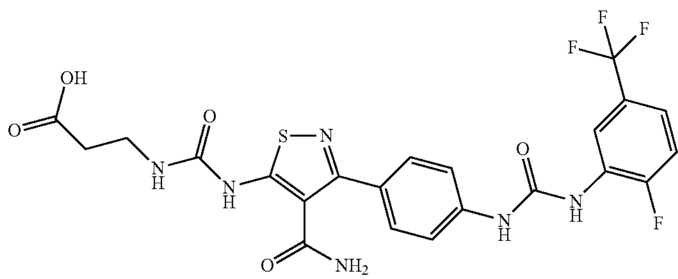 [SMILES: NC(=O)c1c(-c2ccc(NC(=O)Nc3cc(C(F)(F)F)ccc3F)cc2)nsc1NC(=O)NCCC(=O)O] | 3-[3-(4-Carbamoyl-3-{4-[3-(2-fluoro-5-trifluoromethyl-phenyl)-ureido]-phenyl}-isothiazol-5-yl)-ureido]-propionic acid | NT | NT | NT |
| Example 19 | 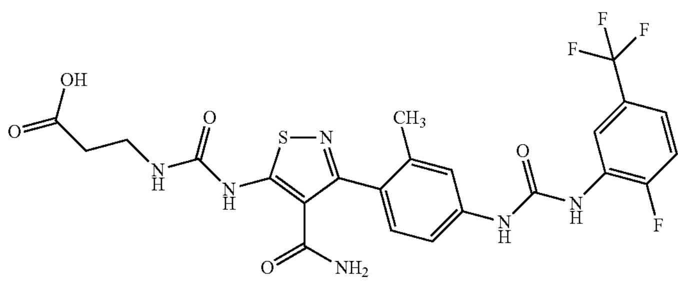 [SMILES: Cc1cc(NC(=O)Nc2cc(C(F)(F)F)ccc2F)ccc1-c1nsc(NC(=O)NCCC(=O)O)c1C(N)=O] | 3-[3-(4-Carbamoyl-3-{4-[3-(2-fluoro-5-trifluoromethyl-phenyl)-ureido]-2-methyl-phenyl}-isothiazol-5-yl)-ureido]-propionic acid | NT | NT | NT |
| Example 20 | 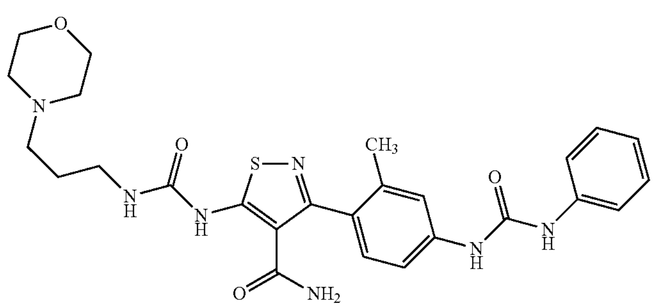 [SMILES: Cc1cc(NC(=O)Nc2ccccc2)ccc1-c1nsc(NC(=O)NCCCN2CCOCC2)c1C(N)=O] | 3-[2-Methyl-4-(3-phenyl-ureido)-phenyl]-5-[3-(3-morpholin-4-yl-propyl)-ureido]-isothiazole-4-carboxylic acid amide | NT | NT | NT |
| Example 21 | 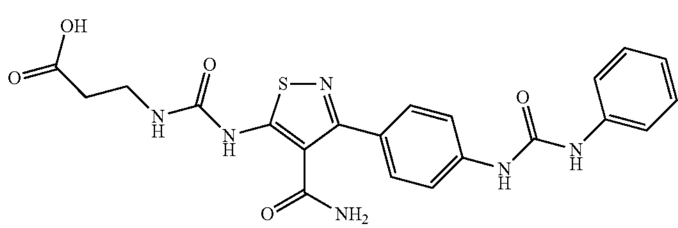 [SMILES: NC(=O)c1c(-c2ccc(NC(=O)Nc3ccccc3)cc2)nsc1NC(=O)NCCC(=O)O] | 3-(3-{4-Carbamoyl-3-[4-(3-phenyl-ureido)-phenyl]-isothiazol-5-yl}-ureido)-propionic acid | NT | NT | NT |
| Example 22 | 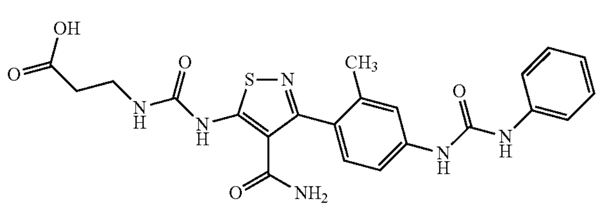 [SMILES: Cc1cc(NC(=O)Nc2ccccc2)ccc1-c1nsc(NC(=O)NCCC(=O)O)c1C(N)=O] | 3-(3-{4-Carbamoyl-3-[2-methyl-4-(3-phenyl-ureido)-phenyl]-isothiazol-5-yl}-ureido)-propionic acid | NT | NT | NT |

TABLE 1-continued

| Example | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 23 | 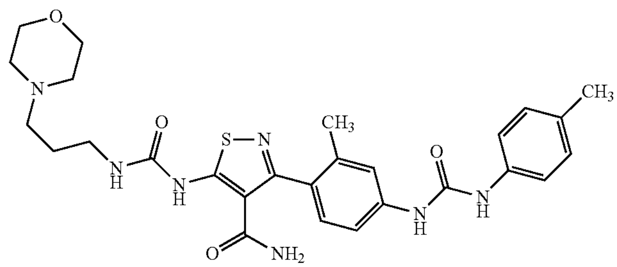 [SMILES: Cc1ccc(NC(=O)Nc2ccc(-c3nsc(NC(=O)NCCCN4CCOCC4)c3C(N)=O)c(C)c2)cc1] | 3-[2-Methyl-4-(3-p-tolyl-ureido)-phenyl]-5-[3-(3-morpholin-4-yl-propyl)-ureido]-isothiazole-4-carboxylic acid amide | NT | NT | NT |
| Example 24 | 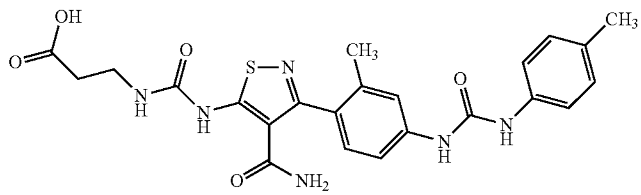 [SMILES: Cc1ccc(NC(=O)Nc2ccc(-c3nsc(NC(=O)NCCC(=O)O)c3C(N)=O)c(C)c2)cc1] | 3-(3-{4-Carbamoyl-3-[2-methyl-4-(3-p-tolyl-ureido)-phenyl]-isothiazol-5-yl}-ureido)-propionic acid | NT | NT | NT |
| Example 25 | 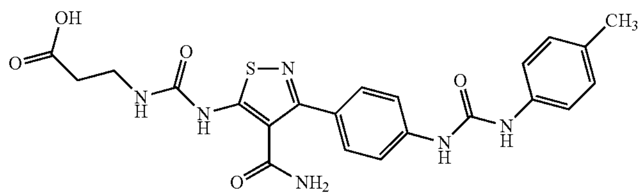 [SMILES: Cc1ccc(NC(=O)Nc2ccc(-c3nsc(NC(=O)NCCC(=O)O)c3C(N)=O)cc2)cc1] | 3-(3-{4-Carbamoyl-3-[4-(3-p-tolyl-ureido)-phenyl]-isothiazol-5-yl}-ureido)-propionic acid | NT | NT | NT |
| Example 26 | 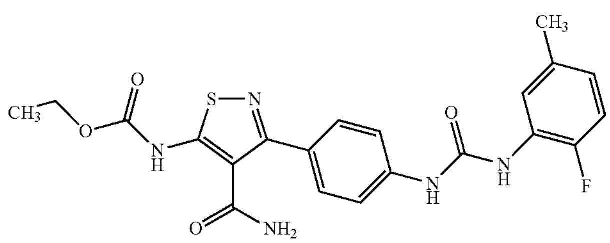 [SMILES: CCOC(=O)Nc1snc(-c2ccc(NC(=O)Nc3cc(C)ccc3F)cc2)c1C(N)=O] | ethyl {4-(aminocarbonyl)-3-[4-({[(2-fluoro-5-methylphenyl)amino]carbonyl}amino)phenyl]isothiazol-5-yl}carbamate | 50 | NT | NT |

NT = not tested

TABLE 2

| Example Number | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 27 | 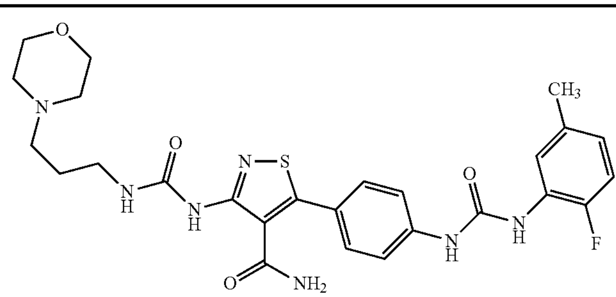 | 5-{4-[3-(2-Fluoro-5-methyl-phenyl)-ureido]-phenyl}-3-[3-(3-morpholin-4-yl-propyl)-ureido]-isothiazole-4-carboxylic acid amide | NT | NT | NT |

TABLE 2-continued

| Example Number | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 28 | 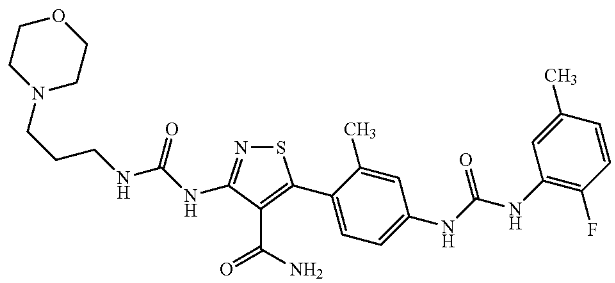 [SMILES: Cc1ccc(F)c(NC(=O)Nc2ccc(-c3snc(NC(=O)NCCCN4CCOCC4)c3C(N)=O)c(C)c2)c1] | 5-{4-[3-(2-Fluoro-5-methyl-phenyl)-ureido]-2-methyl-phenyl}-3-[3-(3-morpholin-4-yl-propyl)-ureido]-isothiazole-4-carboxylic acid amide | NT | NT | NT |
| Example 29 | 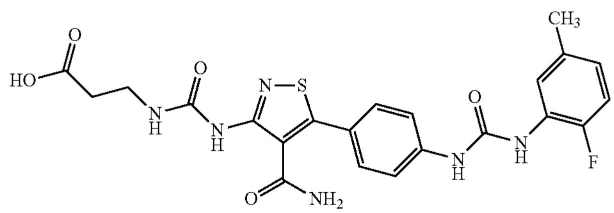 [SMILES: Cc1ccc(F)c(NC(=O)Nc2ccc(-c3snc(NC(=O)NCCC(=O)O)c3C(N)=O)cc2)c1] | 3-[3-(4-Carbamoyl-5-{4-[3-(2-fluoro-5-methyl-phenyl)-ureido]-phenyl}-isothiazol-3-yl)-ureido]-propionic acid | NT | NT | NT |
| Example 30 | 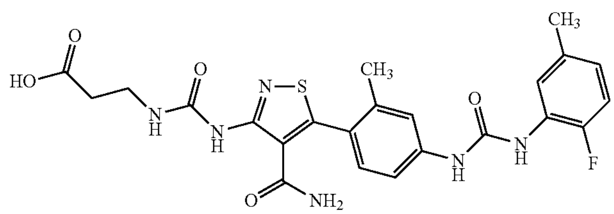 [SMILES: Cc1ccc(F)c(NC(=O)Nc2ccc(-c3snc(NC(=O)NCCC(=O)O)c3C(N)=O)c(C)c2)c1] | 3-[3-(4-Carbamoyl-5-{4-[3-(2-fluoro-5-methyl-phenyl)-ureido]-2-methyl-phenyl}-isothiazol-3-yl)-ureido]-propionic acid | NT | NT | NT |
| Example 31 | 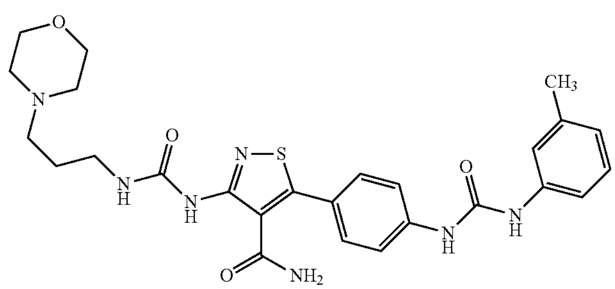 | 3-[3-(3-Morpholin-4-yl-propyl)-ureido]-5-[4-(3-m-tolyl-ureido)-phenyl]-isothiazole-4-carboxylic acid amide | NT | NT | NT |
| Example 32 | 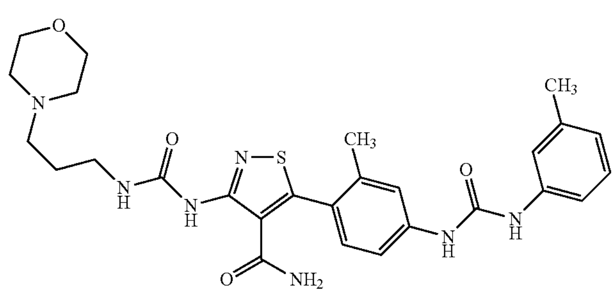 [SMILES: Cc1cccc(NC(=O)Nc2ccc(-c3snc(NC(=O)NCCCN4CCOCC4)c3C(N)=O)c(C)c2)c1] | 5-[2-Methyl-4-(3-m-tolyl-ureido)-phenyl]-3-[3-(3-morpholin-4-yl-propyl)-ureido]-isothiazole-4-carboxylic acid amide | NT | NT | NT |
| Example 33 | 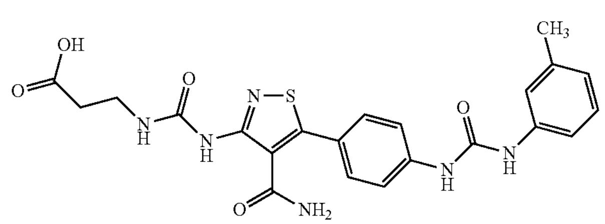 [SMILES: Cc1cccc(NC(=O)Nc2ccc(-c3snc(NC(=O)NCCC(=O)O)c3C(N)=O)cc2)c1] | 3-(3-{4-Carbamoyl-5-[4-(3-m-tolyl-ureido)-phenyl]-isothiazol-3-yl}-ureido)-propionic acid | NT | NT | NT |

TABLE 2-continued

| Example Number | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
| --- | --- | --- | --- | --- | --- |
| Example 34 | 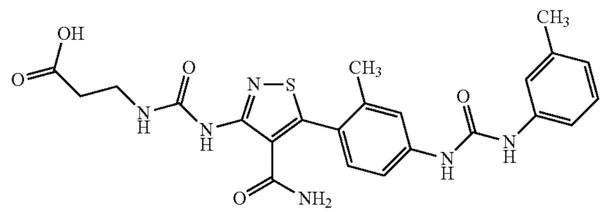 | 3-(3-{4-Carbamoyl-5-[2-methyl-4-{3-m-tolyl-ureido)-phenyl]-isothiazol-3-yl}-ureido)-propionic acid | NT | NT | NT |
| Example 35 | 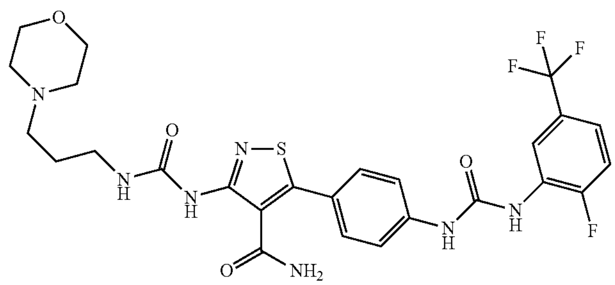 [SMILES: NC(=O)c1c(NC(=O)NCCCN2CCOCC2)nsc1-c1ccc(NC(=O)Nc2cc(C(F)(F)F)ccc2F)cc1] | 5-{4-[3-(2-Fluoro-5-trifluoromethyl-phenyl)-ureido]-phenyl}-3-[3-(3-morpholin-4-yl-propyl)-ureido]-isothiazole-4-carboxylic acid amide | NT | NT | NT |
| Example 36 | 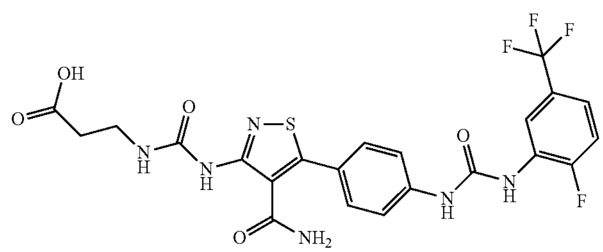 [SMILES: NC(=O)c1c(NC(=O)NCCC(=O)O)nsc1-c1ccc(NC(=O)Nc2cc(C(F)(F)F)ccc2F)cc1] | 3-[3-(4-Carbamoyl-5-{4-[3-(2-fluoro-5-trifluoromethyl-phenyl)-ureido]-phenyl}-isothiazol-3-yl)-ureido]-propionic acid | NT | NT | NT |
| Example 37 | 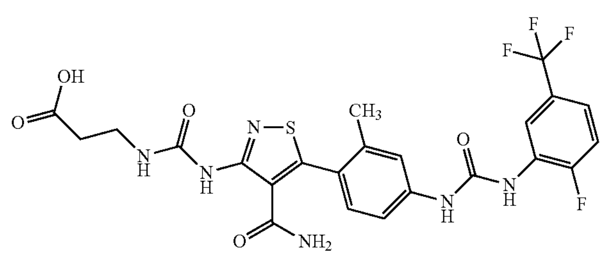 [SMILES: Cc1cc(NC(=O)Nc2cc(C(F)(F)F)ccc2F)ccc1-c1snc(NC(=O)NCCC(=O)O)c1C(N)=O] | 3-[3-(4-Carbamoyl-5-{4-[3-(2-fluoro-5-trifluoromethyl-phenyl)-ureido]-2-methyl-phenyl}-isothiazol-3-yl)-ureido]-propionic acid | NT | NT | NT |
| Example 38 | 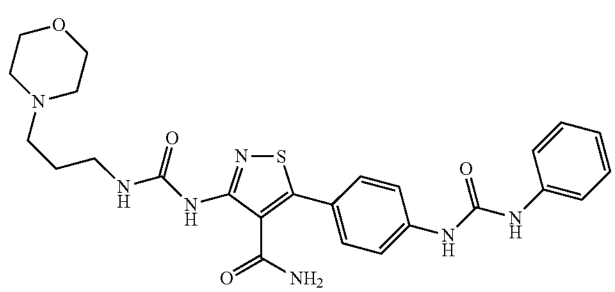 [SMILES: NC(=O)c1c(NC(=O)NCCCN2CCOCC2)nsc1-c1ccc(NC(=O)Nc2ccccc2)cc1] | 3-[3-(3-Morpholin-4-yl-propyl)-ureido]-5-[4-(3-phenyl-ureido)-phenyl]-isothiazole-4-carboxylic acid amide | NT | NT | NT |

TABLE 2-continued

| Example Number | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 39 | 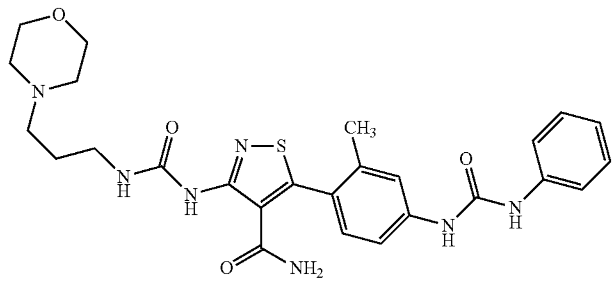 [SMILES: Cc1cc(NC(=O)Nc2ccccc2)ccc1-c1snc(NC(=O)NCCCN2CCOCC2)c1C(N)=O] | 3-[3-(3-Morpholin-4-yl-propyl)-ureido]-5-[4-(3-phenyl-ureido)-phenyl]-isothiazole-4-carboxylic acid amide | NT | NT | NT |
| Example 40 | 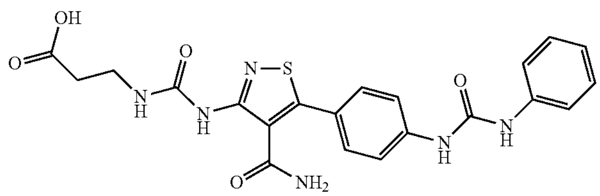 [SMILES: NC(=O)c1c(NC(=O)NCCC(=O)O)nsc1-c1ccc(NC(=O)Nc2ccccc2)cc1] | 3-(3-{4-Carbamoyl-5-[4-(3-phenyl-ureido)-phenyl]-isothiazol-3-yl}-ureido)-propionic acid | NT | NT | NT |
| Example 41 | 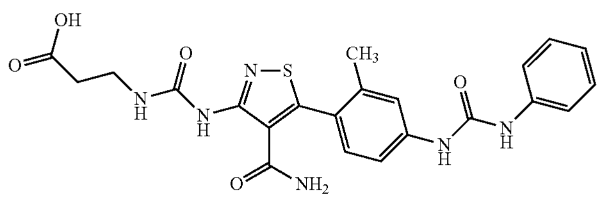 [SMILES: Cc1cc(NC(=O)Nc2ccccc2)ccc1-c1snc(NC(=O)NCCC(=O)O)c1C(N)=O] | 3-(3-{4-Carbamoyl-5-[2-methyl-4-(3-phenyl-ureido)-phenyl]-isothiazol-3-yl}-ureido)-propionic acid | NT | NT | NT |
| Example 42 | 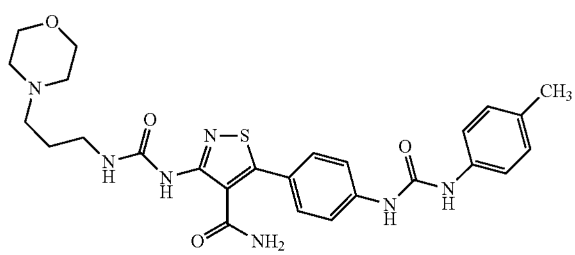 [SMILES: Cc1ccc(NC(=O)Nc2ccc(-c3snc(NC(=O)NCCCN4CCOCC4)c3C(N)=O)cc2)cc1] | 3-[3-(3-Morpholin-4-yl-propyl)-ureido]-5-[4-(3-p-tolyl-ureido)-phenyl]-isothiazole-4-carboxylic acid amide | NT | NT | NT |
| Example 43 | 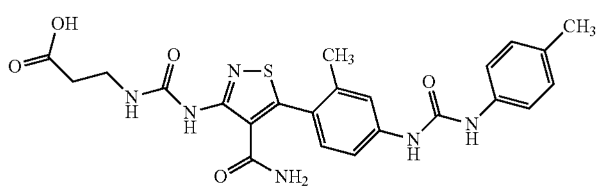 [SMILES: Cc1ccc(NC(=O)Nc2ccc(-c3snc(NC(=O)NCCC(=O)O)c3C(N)=O)c(C)c2)cc1] | 3-(3-{4-Carbamoyl-5-[2-methyl-4-(3-p-tolyl-ureido)-phenyl]-isothiazol-3-yl}-ureido)-propionic acid | NT | NT | NT |
| Example 44 | 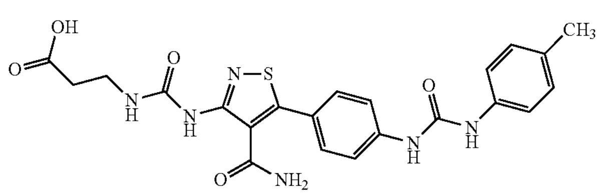 [SMILES: Cc1ccc(NC(=O)Nc2ccc(-c3snc(NC(=O)NCCC(=O)O)c3C(N)=O)cc2)cc1] | 3-(3-{4-Carbamoyl-5-[4-(3-p-tolyl-ureido)-phenyl]-isothiazol-3-yl}-ureido)-propionic acid | NT | NT | NT |

NT = not tested

TABLE 3

| Example | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 45 | 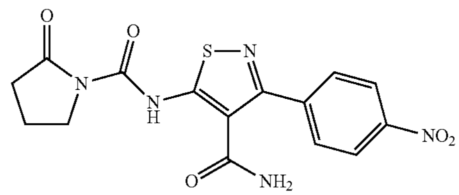 | 3-(4-Nitro-phenyl)-5-[(2-oxo-pyrrolidine-1-carbonyl)-amino]-isothiazole-4-carboxylic acid amide | >10000 | NT | NT |
| Example 46 | 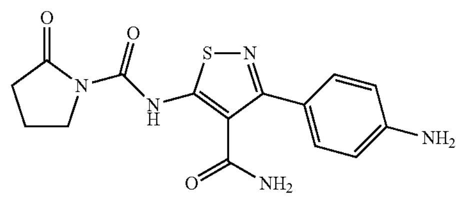 | 3-(4-aminophenyl)-5-{[(2-oxopyrrolidin-1-yl)carbonyl]amino}isothiazole-4-carboxamide | NT | NT | NT |
| Example 47 | 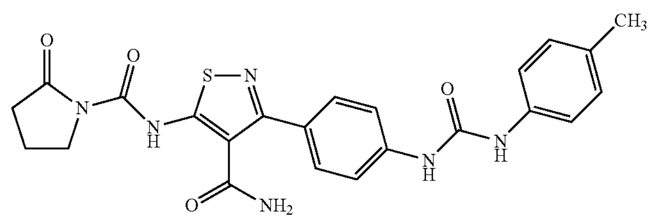 [SMILES: Cc1ccc(NC(=O)Nc2ccc(-c3nsc(NC(=O)N4CCCC4=O)c3C(N)=O)cc2)cc1] | 3-[4-({[(4-methylphenyl)amino]carbonyl}amino)phenyl]-5-{[{2-oxopyrrolidin-1-yl)carbonyl]amino}isothiazole-4-carboxamide | NT | NT | NT |
| Example 48 | 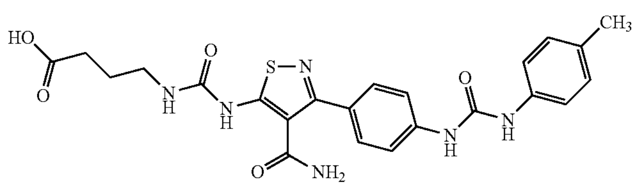 [SMILES: Cc1ccc(NC(=O)Nc2ccc(-c3nsc(NC(=O)NCCCC(=O)O)c3C(N)=O)cc2)cc1] | 4-{[({4-(aminocarbonyl)-3-[4-({[(4-methylphenyl)amino]carbonyl}amino)phenyl]isothiazol-5-yl}amino)carbonyl]amino}butanoic acid | 6 | NT | 10 |
| Example 49 | 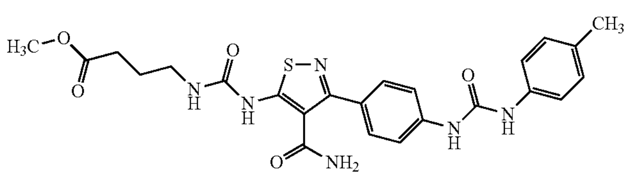 | methyl 4-{[({4-(aminocarbonyl)-3-[4-({[(4-methylphenyl)amino]carbonyl}amino)phenyl]isothiazol-5-yl}amino)carbonyl]amino}butanoate | NT | NT | NT |
| Example 50 | 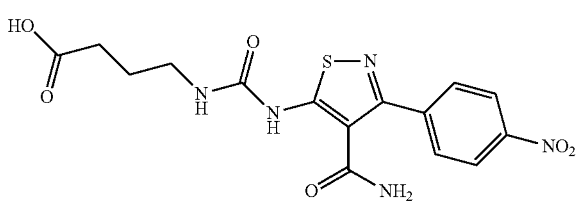 [SMILES: NC(=O)c1c(-c2ccc([N+](=O)[O-])cc2)nsc1NC(=O)NCCCC(=O)O] | 4-[({[4-(aminocarbonyl)-3-(4-nitrophenyl)isothiazol-5-yl]amino}carbonyl)amino]butanoic acid | NT | NT | NT |
| Example 51 | 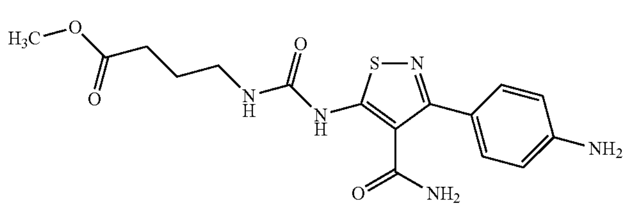 [SMILES: COC(=O)CCCNC(=O)Nc1snc(-c2ccc(N)cc2)c1C(N)=O] | methyl 4-[({[4-(aminocarbonyl)-3-(4-aminophenyl)isothiazol-5-yl]amino}carbonyl)amino]butanoate | NT | NT | NT |

TABLE 3-continued

| Example | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 52 | 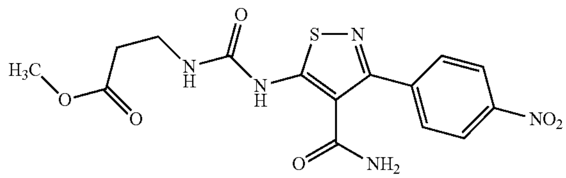 [SMILES: COC(=O)CCNC(=O)Nc1snc(-c2ccc([N+](=O)[O-])cc2)c1C(N)=O] | methyl 3-[({[4-(aminocarbonyl)-3-(4-nitrophenyl)isothiazol-5-yl]amino}carbonyl)amino]propanoate | NT | NT | NT |
| Example 53 | 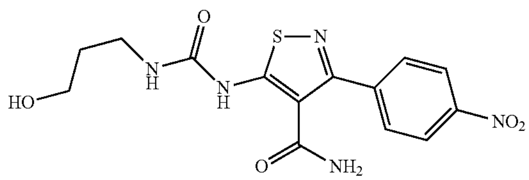 | 5-({[(3-hydroxypropyl)amino]carbonyl}amino)-3-(4-nitrophenyl)isothiazole-4-carboxamide | NT | NT | NT |
| Example 54 | 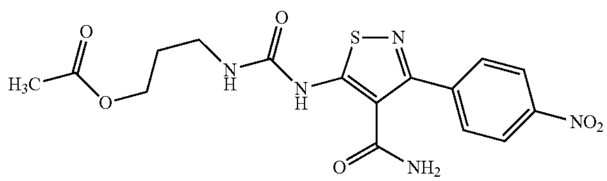 | 3-[({[4-(aminocarbonyl)-3-(4-nitrophenyl)isothiazol-5-yl]amino}carbonyl)amino]propyl acetate | NT | NT | NT |
| Example 55 | 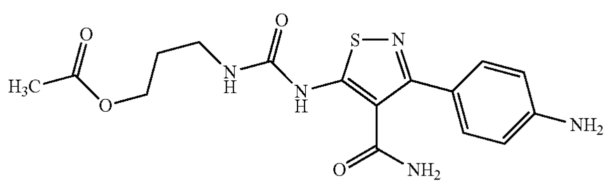 [SMILES: CC(=O)OCCCNC(=O)Nc1snc(-c2ccc([N+](=O)[O-])cc2)c1C(N)=O] | 3-[({[4-(aminocarbonyl)-3-(4-aminophenyl)isothiazol-5-yl]amino}carbonyl)amino]propyl acetate | NT | NT | NT |
| Example 56 | 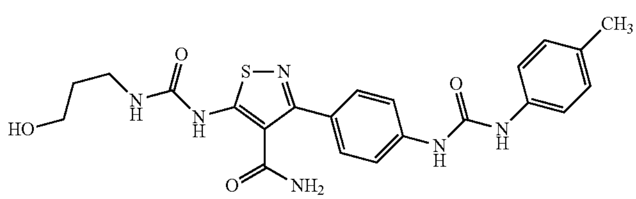 [SMILES: Cc1ccc(NC(=O)Nc2ccc(-c3nsc(NC(=O)NCCCO)c3C(N)=O)cc2)cc1] | 5-({[(3-hydroxypropyl)amino]carbonyl}amino)-3-[4-({[(4-methylphenyl)amino]carbonyl}amino)phenyl]isothiazole-4-carboxamide | 7 | NT | 13 |
| Example 57 | 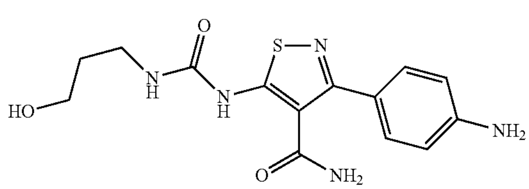 | 3-(4-aminophenyl)-5-({[{3-hydroxypropyl)amino]carbonyl}amino)isothiazole-4-carboxamide | 2520 | NT | NT |
| Example 58 | 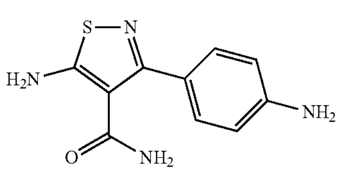 [SMILES: NC(=O)c1c(-c2ccc(N)cc2)nsc1N] | 5-amino-3-(4-aminophenyl)isothiazole-4-carboxamide | >10000 | NT | NT |

TABLE 3-continued

| Example | Structure | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|---|
| Example 59 | 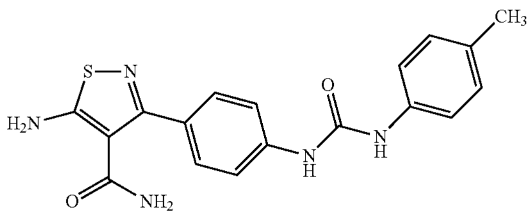 [SMILES: Cc1ccc(NC(=O)Nc2ccc(-c3nsc(N)c3C(N)=O)cc2)cc1] | 5-amino-3-[4-({[(4-methylphenyl)amino]carbonyl}amino)phenyl]isothiazole-4-carboxamide | 176 | NT | 60 |
| Example 60 | 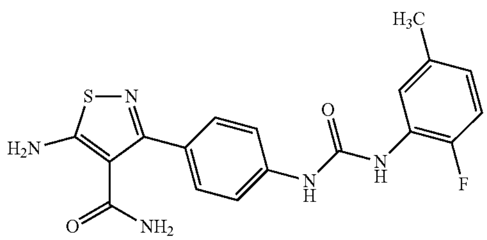 [SMILES: Cc1ccc(F)c(NC(=O)Nc2ccc(-c3nsc(N)c3C(N)=O)cc2)c1] | 5-amino-3-[4-({[(2-fluoro-5-methylphenyl)amino]carbonyl}amino)phenyl]isothiazole-4-carboxamide | 24 | NT | 70 |
| Example 61 | 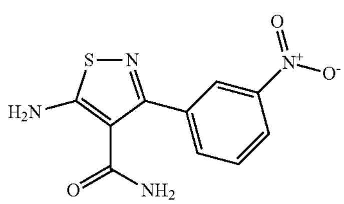 [SMILES: NC(=O)c1c(-c2cccc([N+](=O)[O-])c2)nsc1N] | 5-amino-3-(3-nitrophenyl)isothiazole-4-carboxamide | >10000 | NT | NT |
| Example 62 | 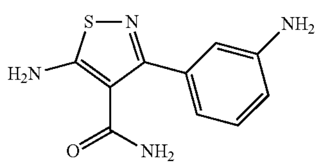 [SMILES: NC(=O)c1c(-c2cccc(N)c2)nsc1N] | 5-amino-3-(3-aminophenyl)isothiazole-4-carboxamide | >10000 | NT | NT |
| Example 63 | 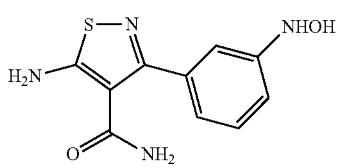 | 5-amino-3-[3-(hydroxyamino)phenyl]isothiazole-4-carboxamide | 1210 | NT | NT |
| Example 64 | 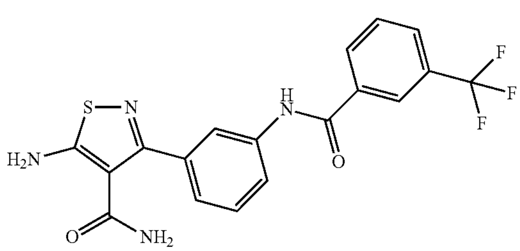 [SMILES: NC(=O)c1c(-c2cccc(NC(=O)c3cccc(C(F)(F)F)c3)c2)nsc1N] | 5-amino-3-(3-{(3-trifluoromethyl)benzoyl]amino}phenyl)isothiazole-4-carboxamide | 1640 | NT | 844 |
| Example 65 | 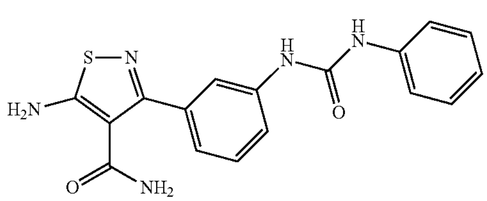 [SMILES: NC(=O)c1c(-c2cccc(NC(=O)Nc3ccccc3)c2)nsc1N] | 5-amino-3-{3-[(anilinocarbonyl)amino]phenyl}isothiazole-4-carboxamide | >10000 | NT | >1000 |

TABLE 3-continued

| Example | Compound Name | VEGFR2 Enzyme Assay (IC$_{50}$ nM) | VEGFR1 Enzyme Assay (IC$_{50}$ nM) | PDGFRβ Enzyme Assay (IC$_{50}$ nM) |
|---|---|---|---|---|
| Example 66 | 3-(4-nitrophenyl)-5-({[(3-pyrrolidin-1-ylpropyl)amino]carbonyl}amino)isothiazole-4-carboxamide | NT | NT | NT |
| Example 67 | 3-(4-aminophenyl)-5-({[(3-pyrrolidin-1-ylpropyl)amino]carbonyl}amino)isothiazole-4-carboxamide | >1000 | NT | NT |
| Example 68 | 3-[4-({[(4-methylphenyl)amino]carbonyl}amino)phenyl]-5-({[(3-pyrrolidin-1-ylpropyl)amino]carbonyl}amino)isothiazole-4-carboxamide | 10 | NT | 12 |
| Example 69 | 3-amino-5-[4-({[(2-fluoro-5-methylphenyl)amino]carbonyl}amino)phenyl]isothiazole-4-carboxamide | 12 | NT | 48 |
| Example 70 | 5-[4-({[(2-fluoro-5-methylphenyl)amino]carbonyl}amino)phenyl]-3-[(3-morpholin-4-ylpropyl)amino]isothiazole-4-carboxamide | 27 | NT | 70 |
| Example 71 | 3-[(2,4-dimethoxybenzyl)amino]-5-[4-({[(2-fluoro-5-methylphenyl)amino]carbonyl}amino)phenyl]isothiazole-4-carboxamide | 98 | NT | |

NT = not tested

What is claimed is:

1. A compound of Formula I:

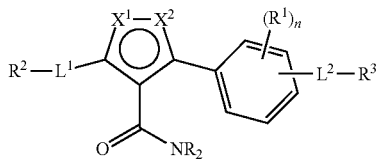

Formula I or a pharmaceutically acceptable salt thereof, wherein:
$X^1$ is N and $X^2$ is S;
$L^1$ is selected from the group consisting of —N(R)—, —N(R)—C(=O)—N(R)—, —O—C(=O)—N(R)—, —N(R)—C(=O)— and —C(=O)—N(R)—;
$L^2$ is selected from the group consisting of a covalent bond, —N(R)—, —N(R)—C(=O), —C(=O)—N(R)— and —N(R)—C(=O)—N(R)—;
each R independently is H or $C_{1-6}$ alkyl;
each $R^1$ independently is selected from the group consisting of $C_{1-6}$ alkyl, $C_{1-6}$ haloalkyl, halogen, and OR; or wherein two adjacent $R^1$ groups taken together with the carbon atoms to which they are attached form a six-membered aryl or a five- or six-membered heteroaryl;
n is 0, 1, or 2;
$R^2$ is selected from the group consisting of: a) H; b) $C_{1-6}$ alkyl that is unsubstituted or substituted with one or two substituents selected from the group consisting of heterocyclyl, —C(=O)OR, hydroxy, and $C_{1-6}$ alkoxy; and c)

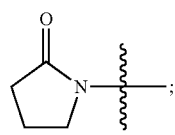

and
$R^3$ is selected from the group consisting of H, hydroxy, —$NO_2$, aryl, and heteroaryl, wherein said aryl or heteroaryl is unsubstituted or substituted with one to three substituents selected from the group consisting of halo, $C_{1-6}$ haloalkyl, and $C_{1-6}$ alkyl.

2. The compound of claim 1, wherein $L^1$ is selected from the group consisting of —N(H)—, —N(H)—C(=O)—, —N(H)—C(=O)—N(H)—, —O—C(=O)—N(H)—, —N(R)—C(=O)—, and —C(=O)—N(R)—.

3. The compound of claim 1, wherein $L^2$ is selected from the group consisting of a covalent bond, —N(H)—, —N(H)—C(=O)—, —C(=O)—N(R)—, and —N(H)—C(=O)—N(H)—.

4. The compound of claim 1, wherein n is 0 or 1.

5. The compound of claim 1, wherein $R^2$ is selected from the group consisting of H,

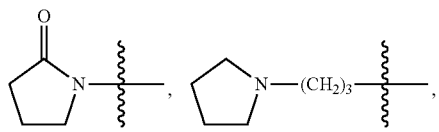

2,4-dimethoxybenzyl, morpholinyl-$(CH_2)_3$—, HO—C(=O)—$(CH_2)_2$—, HO—C(=O)—$(CH_2)_3$—, $CH_3$O—C(=O)—$(CH_2)_2$—, $CH_3$O—C(=O)—$(CH_2)_3$—, HO—$(CH_2)_3$—, $CH_3$O—$(CH_2)_3$—, and ethyl.

6. The compound of claim 1, wherein $R^3$ is selected from the group consisting of H, —$NO_2$, hydroxy, and aryl that is unsubstituted or substituted with one to two substituents selected from the group consisting of methyl, fluoro, and trifluoromethyl.

7. The compound of claim 1, wherein the compound of Formula I is represented by Formula IA:

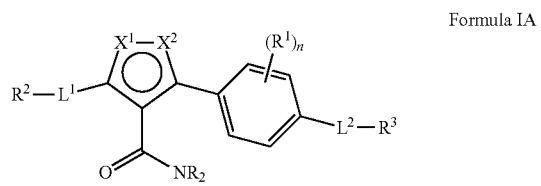

Formula IA wherein $X^1$, $X^2$, n, R, $R^1$, $R^2$, $R^3$, $L^1$ and $L^2$ are as set forth for Formula I.

8. The compound of claim 1, wherein:
$L^1$ is selected from the group consisting of —N(H)—, —N(H)—C(=O)—N(H)— and —O—C(=O)—N(H)—;
$L^2$ is selected from the group consisting of a covalent bond, —N(H)—, —N(H)—C(=O)— and —N(H)—C(=O)—N(H)—;
$R^1$ is methyl;
$R^2$ is selected from the group consisting of H, morpholinyl-$(CH_2)_3$—, HO—C(=O)—$(CH_2)_2$—, $CH_3$O—$(CH_2)_3$—, and ethyl; and
$R^3$ is selected from the group consisting of H, —$NO_2$, and aryl that is unsubstituted or substituted with one to two substituents selected from the group consisting of methyl, fluoro, and trifluoromethyl.

9. A compound selected from the group consisting of:
5-{4-[3-(2-Fluoro-5-methyl-phenyl)-ureido]-phenyl}-3-[3-(3-morpholin-4-yl-propyl)-ureido]-isothiazole-4-carboxylic acid amide;
5-{4-[3-(2-Fluoro-5-methyl-phenyl)-ureido]-2-methyl-phenyl}-3-[3-(3-morpholin-4-yl-propyl)-ureido]-isothiazole-4-carboxylic acid amide;
3-[3-(4-Carbamoyl-5-{4-[3-(2-fluoro-5-methyl-phenyl)-ureido]-phenyl}-isothiazol-3-yl)-ureido]-propionic acid;
3-[3-(4-Carbamoyl-5-{4-[3-(2-fluoro-5-methyl-phenyl)-ureido]-2-methyl-phenyl}-isothiazol-3-yl)-ureido]-propionic acid;
3-[3-(3-Morpholin-4-yl-propyl)-ureido]-5-[4-(3-m-tolyl-ureido)-phenyl]-isothiazole-4-carboxylic acid amide;
5-[2-Methyl-4-(3-m-tolyl-ureido)-phenyl]-3-[3-(3-morpholin-4-yl-propyl)-ureido]-isothiazole-4-carboxylic acid amide;
3-(3-{4-Carbamoyl-5-[4-(3-m-tolyl-ureido)-phenyl]-isothiazol-3-yl}-ureido)-propionic acid;
3-(3-{4-Carbamoyl-5-[2-methyl-4-(3-m-tolyl-ureido)-phenyl]-isothiazol-3-yl}-ureido)-propionic acid;
5-{4-[3-(2-Fluoro-5-trifluoromethyl-phenyl)-ureido]-phenyl}-3-[3-(3-morpholin-4-yl-propyl)-ureido]-isothiazole-4-carboxylic acid amide;
5-{4-[3-(2-Fluoro-5-trifluoromethyl-phenyl)-ureido]-2-methyl-phenyl}-3-[3-(3-morpholin-4-yl-propyl)-ureido]-isothiazole-4-carboxylic acid amide;

3-[3-(4-Carbamoyl-5-{4-[3-(2-fluoro-5-trifluoromethyl-phenyl)-ureido]-phenyl}-isothiazol-3-yl)-ureido]-propionic acid;
3-[3-(4-Carbamoyl-5-{4-[3-(2-fluoro-5-trifluoromethyl-phenyl)-ureido]-2-methyl-phenyl}-isothiazol-3-yl)-ureido]-propionic acid;
3-[3-(3-Morpholin-4-yl-propyl)-ureido]-5-[4-(3-phenyl-ureido)-phenyl]-isothiazole-4-carboxylic acid amide;
3-(3-{4-Carbamoyl-5-[4-(3-phenyl-ureido)-phenyl]-isothiazol-3-yl}-ureido)-propionic acid;
3-(3-{4-Carbamoyl-5-[2-methyl-4-(3-phenyl-ureido)-phenyl]-isothiazol-3-yl}-ureido)-propionic acid;
3-[3-(3-Morpholin-4-yl-propyl)-ureido]-5-[4-(3-p-tolyl-ureido)-phenyl]-isothiazole-4-carboxylic acid amide;
5-[2-Methyl-4-(3-p-tolyl-ureido)-phenyl]-3-[3-(3-morpholin-4-yl-propyl)-ureido]-isothiazole-4-carboxylic acid amide;
3-(3-{4-Carbamoyl-5-[2-methyl-4-(3-p-tolyl-ureido)-phenyl]-isothiazol-3-yl}-ureido)-propionic acid;
3-(3-{4-Carbamoyl-5-[4-(3-p-tolyl-ureido)-phenyl]-isothiazol-3-yl}-ureido)-propionic acid;
3-amino-5-[4-({[(2-fluoro-5-methylphenyl)amino]carbonyl}amino)phenyl]isothiazole-4-carboxamide;
5-[4-({[(2-fluoro-5-methylphenyl)amino]carbonyl}amino)phenyl]-3-[(3-morpholin-4-ylpropyl)amino]isothiazole-4-carboxamide; and
3-[(2,4-dimethoxybenzyl)amino]-5-[4-({[(2-fluoro-5-methylphenyl)amino]carbonyl}amino)phenyl]isothiazole-4-carboxamide; or a pharmaceutically acceptable salt thereof.

10. A compound selected from the group consisting of:
5-({[(3-morpholin-4-ylpropyl)amino]carbonyl}amino)-3-(4-nitrophenyl)isothiazole-4-carboxamide;
3-(4-aminophenyl)-5-({[(3-methoxypropyl)amino]carbonyl}amino)isothiazole-4-carboxamide;
5-({[(3-methoxypropyl)amino]carbonyl}amino)-3-(4-nitrophenyl)isothiazole-4-carboxamide;
3-[4-({[(2-fluoro-5-methylphenyl)amino]carbonyl}amino)phenyl]-5-({[(3-methoxypropyl)amino]carbonyl}amino)isothiazole-4-carboxamide;
ethyl {4-(aminocarbonyl)-3-[4-({[(2-fluoro-5-methylphenyl)amino]carbonyl}amino)phenyl]isothiazol-5-yl}carbamate;
3-[4-({[(2-fluoro-5-methylphenyl)amino]carbonyl}amino)phenyl]-5-({[(3-morpholin-4-ylpropyl)amino]carbonyl}amino)isothiazole-4-carboxamide;
3-{4-[3-(2-Fluoro-5-methyl-phenyl)-ureido]-2-methyl-phenyl}-5-[3-(3-morpholin-4-yl-propyl)-ureido]-isothiazole-4-carboxylic acid amide;
3-[3-(4-Carbamoyl-3-{4-[3-(2-fluoro-5-methyl-phenyl)-ureido]-phenyl}-isothiazol-5-yl)-ureido]-propionic acid;
3-[3-(4-Carbamoyl-3-{4-[3-(2-fluoro-5-methyl-phenyl)-ureido]-2-methyl-phenyl}-isothiazol-5-yl)-ureido]-propionic acid;
3-[4-({[(3-methylphenyl)amino]carbonyl}amino)phenyl]-5-({[(3-morpholin-4-ylpropyl)amino]carbonyl}amino)isothiazole-4-carboxamide;
3-[2-Methyl-4-(3-m-tolyl-ureido)-phenyl]-5-[3-(3-morpholin-4-yl-propyl)-ureido]-isothiazole-4-carboxylic acid amide;
3-(3-{4-Carbamoyl-3-[4-(3-m-tolyl-ureido)-phenyl]-isothiazol-5-yl}-ureido)-propionic acid;
3-(3-{4-Carbamoyl-3-[2-methyl-4-(3-m-tolyl-ureido)-phenyl]-isothiazol-5-yl}-ureido)-propionic acid;
3-{4-[({[2-fluoro-5-(trifluoromethyl)phenyl]amino}carbonyl)amino]phenyl}-5-({[(3-morpholin-4-ylpropyl)amino]carbonyl}amino)isothiazole-4-carboxamide;
3-{4-[3-(2-Fluoro-5-trifluoromethyl-phenyl)-ureido]-2-methyl-phenyl}-5-[3-(3-morpholin-4-yl-propyl)-ureido]-isothiazole-4-carboxylic acid amide;
3-[3-(4-Carbamoyl-3-{4-[3-(2-fluoro-5-trifluoromethyl-phenyl)-ureido]-phenyl}-isothiazol-5-ylureido]-propionic acid;
3-[3-(4-Carbamoyl-3-{4-[3-(2-fluoro-5-trifluoromethyl-phenyl)-ureido]-2-methyl-phenyl}-isothiazol-5-ylureido]-propionic acid;
3-{4-[(anilinocarbonyl)amino]phenyl}-5-({[(3-morpholin-4-ylpropyl)amino]carbonyl}amino)isothiazole-4-carboxamide;
3-[2-Methyl-4-(3-phenyl-ureido)-phenyl]-5-[3-(3-morpholin-4-yl-propyl)-ureido]-isothiazole-4-carboxylic acid amide;
3-(3-{4-Carbamoyl-3-[4-(3-phenyl-ureido)-phenyl]-isothiazol-5-yl}-ureido)-propionic acid;
3-(3-{4-Carbamoyl-3-[2-methyl-4-(3-phenyl-ureido)-phenyl]-isothiazol-5-yl}-ureido)-propionic acid;
3-(4-aminophenyl)-5-({[(3-morpholin-4-ylpropyl)amino]carbonyl}amino)isothiazole-4-carboxamide;
3-[4-({[(4-methylphenyl)amino]carbonyl}amino)phenyl]-5-({[(3-morpholin-4-ylpropyl)amino]carbonyl}amino)isothiazole-4-carboxamide;
3-[2-Methyl-4-(3-p-tolyl-ureido)-phenyl]-5-[3-(3-morpholin-4-yl-propyl)-ureido]-isothiazole-4-carboxylic acid amide;
3-(3-{4-Carbamoyl-3-[2-methyl-4-(3-p-tolyl-ureido)-phenyl]-isothiazol-5-yl}-ureido)-propionic acid;
3-(3-{4-Carbamoyl-3-[4-(3-p-tolyl-ureido)-phenyl]-isothiazol-5-yl}-ureido)-propionic acid;
5-({[(3-morpholin-4-ylpropyl)amino]carbonyl}amino)-3-(4-{[3-(trifluoromethyl)benzoyl]amino}phenyl)isothiazole-4-carboxamide;
3-(4-Nitro-phenyl)-5-[(2-oxo-pyrrolidine-1-carbonyl)-amino]-isothiazole-4-carboxylic acid amide;
3-(4-aminophenyl)-5-{[(2-oxopyrrolidin-1-yl)carbonyl]amino}isothiazole-4-carboxamide;
3-[4-({[(4-methylphenyl)amino]carbonyl}amino)phenyl]-5-{[(2-oxopyrrolidin-1-yl)carbonyl]amino}isothiazole-4-carboxamide;
4-{[({4-(aminocarbonyl)-3-[4-({[(4-methylphenyl)amino]carbonyl}amino)phenyl]isothiazol-5-yl}amino)carbonyl]amino}butanoic acid;
methyl 4-{([{4-(aminocarbonyl)-3-[4-({[(4-methylphenyl)amino]carbonyl}amino)phenyl]isothiazol-5-yl}amino)carbonyl]amino}butanoate;
4-[({[4-(aminocarbonyl)-3-(4-nitrophenyl)isothiazol-5-yl]amino}carbonyl)amino]butanoic acid;
methyl 4-[({[4-(aminocarbonyl)-3-(4-aminophenyl)isothiazol-5-yl]amino}carbonyl)amino]butanoate;
methyl 3-[({[4-(aminocarbonyl)-3-(4-nitrophenyl)isothiazol-5-yl]amino}carbonyl)amino]propanoate;
5-({[(3-hydroxypropyl)amino]carbonyl}amino)-3-(4-nitrophenyl)isothiazole-4-carboxamide;
3-[({[4-(aminocarbonyl)-3-(4-nitrophenyl)isothiazol-5-yl]amino}carbonyl)amino]propyl acetate;
3-[({[4-(aminocarbonyl)-3-(4-aminophenyl)isothiazol-5-yl]amino}carbonyl)amino]propyl acetate;
5-({[(3-hydroxypropyl)amino]carbonyl}amino)-3-[4-({[(4-methylphenyl)amino]carbonyl}amino)phenyl]isothiazole-4-carboxamide;

3-(4-aminophenyl)-5-({[(3-hydroxypropyl)amino]carbonyl}amino)isothiazole-4-carboxamide;
5-amino-3-(4-aminophenyl)isothiazole-4-carboxamide;
5-amino-3-[4-({[(4-methylphenyl)amino]carbonyl}amino)phenyl]isothiazole-4-carboxamide;
5-amino-3-[4-({[(2-fluoro-5-methylphenyl)amino]carbonyl}amino)phenyl]isothiazole-4-carboxamide;
5-amino-3-(3-nitrophenyl)isothiazole-4-carboxamide;
5-amino-3-(3-aminophenyl)isothiazole-4-carboxamide;
5-amino-3-[3-(hydroxyamino)phenyl]isothiazole-4-carboxamide;
5-amino-3-(3-{[3-(trifluoromethyl)benzoyl]amino}phenyl)isothiazole-4-carboxamide;
5-amino-3-{3-[(anilinocarbonyl)amino]phenyl}isothiazole-4-carboxamide;
3-(4-nitrophenyl)-5-({[(3-pyrrolidin-1-ylpropyl)amino]carbonyl}amino)isothiazole-4-carboxamide;
3-(4-aminophenyl)-5-({[(3-pyrrolidin-1-ylpropyl)amino]carbonyl}amino)isothiazole-4-carboxamide;
3-[4-({[(4-methylphenyl)amino]carbonyl}amino)phenyl]-5-({[(3-pyrrolidin-1-ylpropyl)amino]carbonyl}amino)isothiazole-4-carboxamide;
3-amino-5-[4-({[(2-fluoro-5-methylphenyl)amino]carbonyl}amino)phenyl]isothiazole-4-carboxamide;
5-[4-({[(2-fluoro-5-methylphenyl)amino]carbonyl}amino)phenyl]-3-[(3-morpholin-4-ylpropyl)amino]isothiazole-4-carboxamide; and
3-[(2,4-dimethoxybenzyl)amino]-5-[4-({[(2-fluoro-5-methylphenyl)amino]carbonyl}amino)phenyl]isothiazole-4-carboxamide; or a pharmaceutically acceptable salt thereof.

11. A pharmaceutical composition comprising at least one compound of claim 1, or a pharmaceutically acceptable salt thereof, and a pharmaceutically acceptable carrier.

12. A method of treating a blood vessel proliferative disorder selected from the group consisting of diabetic retinopathy, age-related macular degeneration, retinopathy of prematurity, pterigium, arthritis and restenosis, the method comprising the step of administering to a subject in need thereof, a therapeutically effective amount of at least one compound of claim 1, or a pharmaceutically acceptable salt thereof.

13. A pharmaceutical composition comprising at least one compound of claim 9, or a pharmaceutically acceptable salt thereof, and a pharmaceutically acceptable carrier.

14. A pharmaceutical composition comprising at least one compound of claim 10, or a pharmaceutically acceptable salt thereof, and a pharmaceutically acceptable carrier.

15. A method of treating a blood vessel proliferative disorder selected from the group consisting of diabetic retinopathy, age-related macular degeneration, retinopathy of prematurity, pterigium, arthritis and restenosis, the method comprising the step of administering to a subject in need thereof, a therapeutically effective amount of at least one compound of claim 9, or a pharmaceutically acceptable salt thereof.

16. A method of treating a blood vessel proliferative disorder selected from the group consisting of diabetic retinopathy, age-related macular degeneration, retinopathy of prematurity, pterigium, arthritis and restenosis, the method comprising the step of administering to a subject in need thereof, a therapeutically effective amount of at least one compound of claim 10, or a pharmaceutically acceptable salt thereof.

* * * * *

UNITED STATES PATENT AND TRADEMARK OFFICE
CERTIFICATE OF CORRECTION

PATENT NO. : 8,969,583 B2  
APPLICATION NO. : 13/728502  
DATED : March 3, 2015  
INVENTOR(S) : Thomas C. Malone et al.

It is certified that error appears in the above-identified patent and that said Letters Patent is hereby corrected as shown below:

On the Title Page

Item (54), and in the Specification, in column 1, line 2, in "Title", delete "CARBOXIMIDE" and insert -- CARBOXAMIDE --, therefor.

Item (75), in column 1, in "Inventor", line 2, delete "Eugene Hull," and insert -- Eugene Hull III, --, therefor.

On the Page 2, item (56), in column 1, under "Other Publications", line 10, delete "Phaim." and insert -- Pharm. --, therefor.

In the Specification

In column 2, line 23, delete "Opthalmologica" and insert -- Ophthalmologica --, therefor.

In column 3, line 6, delete "pterigium," and insert -- pterygium, --, therefor.

In column 4, line 24, delete "L'" and insert -- L1 --, therefor.

In column 4, line 28, delete "L'" and insert -- L1 --, therefor.

In column 9, line 53, delete "(PDGFRb)" and insert -- (PDGFRβ) --, therefor.

In column 9, line 66, delete "retinopathy," and insert -- retinopathy --, therefor.

In column 9, line 67, delete "pterigium," and insert -- pterygium, --, therefor.

In column 17, line 26, delete "quarternized" and insert -- quaternized --, therefor.

In column 18, line 40, delete "1974." and insert -- 1974 --, therefor.

In column 27, line 13, delete "4H)" and insert -- 4H). --, therefor.

In column 27, line 48, delete "the" and insert -- The --, therefor.

In column 29, line 35, delete "cm-1" and insert -- cm-1. --, therefor.

In column 36, line 58, delete "disolved." and insert -- dissolved. --, therefor.

In column 37, line 5, delete "mortor" and insert -- mortar --, therefor.

Signed and Sealed this  
Ninth Day of June, 2015

Michelle K. Lee  
*Director of the United States Patent and Trademark Office*

CERTIFICATE OF CORRECTION (continued)
U.S. Pat. No. 8,969,583 B2

In column 37, line 5, delete "pestal" and insert -- pestle --, therefor.

In column 41, line 2, delete "titlee" and insert -- title --, therefor.

In column 43, line 10, delete "troom" and insert -- room --, therefor.

In column 44, line 18, delete "throught" and insert -- through --, therefor.

In column 44, line 46, delete "pripionic" and insert -- -propionic --, therefor.

In column 49, line 24, delete "siimilar" and insert -- similar --, therefor.

In column 52, line 7, delete "over night." and insert -- overnight. --, therefor.

In column 59, line 19, delete "PDGFR-b" and insert -- PDGFR-β --, therefor.

In the Claims

In column 90, line 9, in claim 10, delete "ylyureido]" and insert -- yl)-ureido] --, therefor.

In column 90, line 13-14, in claim 10, delete "ylyureido]" and insert -- yl)-ureido] --, therefor.

In column 90, line 50, in claim 10, delete "4-{([" and insert -- 4-{[( --, therefor.

In column 92, line 4, in claim 12, delete "pterigium," and insert -- pterygium, --, therefor.

In column 92, line 19, in claim 15, delete "pterigium," and insert -- pterygium, --, therefor.

In column 92, line 27, in claim 16, delete "pterigium," and insert -- pterygium, --, therefor.